(12) United States Patent
Maione

(10) Patent No.: US 8,940,704 B2
(45) Date of Patent: Jan. 27, 2015

(54) ADVANTAGEOUS SALTS OF μ-OPIATE RECEPTOR PEPTIDES

(71) Applicant: Cytogel Pharma, LLC, Darien, CT (US)

(72) Inventor: Theodore E Maione, Green Island, NY (US)

(73) Assignee: Cytogel Pharma, LLC, Darien, CT (US)

( * ) Notice: Subject to any disclaimer, the term of this patent is extended or adjusted under 35 U.S.C. 154(b) by 0 days.

(21) Appl. No.: 14/056,496

(22) Filed: Oct. 17, 2013

(65) Prior Publication Data
US 2014/0142050 A1  May 22, 2014

Related U.S. Application Data

(63) Continuation of application No. 12/744,859, filed as application No. PCT/US2008/086838 on Dec. 15, 2008, now abandoned.

(60) Provisional application No. 61/007,617, filed on Dec. 13, 2007.

(51) Int. Cl.
*A61K 38/00* (2006.01)
*C07K 5/10* (2006.01)
*C07K 5/107* (2006.01)

(52) U.S. Cl.
CPC .................. *C07K 5/10* (2013.01); *C07K 5/1016* (2013.01); *A61K 38/00* (2013.01)
USPC ......................................... 514/21.9; 530/330

(58) Field of Classification Search
None
See application file for complete search history.

(56) References Cited

U.S. PATENT DOCUMENTS

| | | | |
|---|---|---|---|
| 5,885,958 | A | 3/1999 | Zadina et al. |
| 6,303,578 | B1 | 10/2001 | Zadina et al. |
| 6,514,710 | B1 | 2/2003 | Jones et al. |
| 2003/0068672 | A1 | 4/2003 | Yu |
| 2003/0139446 | A1 | 7/2003 | Chen et al. |
| 2004/0266805 | A1 | 12/2004 | Jessop et al. |

FOREIGN PATENT DOCUMENTS

| | | |
|---|---|---|
| JP | 10-330398 | 12/1998 |
| WO | WO 98/42732 | 10/1998 |
| WO | WO 02/102833 A1 | 12/2002 |

OTHER PUBLICATIONS

Berge, Stephan, "Pharmaceutical Salts," *Journal of Pharmaceutical Sciences*, Jan. 1977, vol. 66, No. 1, p. 1-19.
Cardillo, Giuliana et al., "Endomorphin-1 Analogues Containing β-Proline Are μ-Opioid Receptor Agonists and Display Enhanced Enzymatic Hydrolysis Resistance," *Journal of Medicinal Chemistry*, 2002, vol. 45, p. 2571-2578.
Cardillo, Giuliana et al., "Stability against enzymatic hydrolysis of endomorphin-1 analogues containing β-proline," *Organic & Bimolecular Chemistry*, 2003, vol. 1, p. 1498-1502.
Cornish, J. et al., "Trifluoroacetate, a contaminant in purified proteins inhibits proliferation of osteoblasts and chondrocytes," *The American Physiological Society—Endocrinology and Metabolism*, 1999, vol. 277, p. E779-E783.
Janecka, Anna et al., "Synthesis and antinociceptive activity of cyclic endomorphin-2 and morphiceptin analogs," *Biochemical Pharmacology*, 2005, vol. 71, p. 188-195.
Janecka, Anna et al., "Enzymatic degradation studies of endomorphin-2 and its analogs containing N-methylated amino acids," *Peptides*, 2006, vol. 27, p. 131-135.
McPherson, Alexander, "A comparison of salts for the crystallization of macromolecules," *Protein Science*, 2001, vol. 10, p. 418-422.
Neumeyer, John et al., "New Opioid Designed Multiple Ligand from Dmt-Tic and Morphinan Pharmacophores," *Journal of Medicinal Chemistry*, 2006, vol. 49, p. 5640-5643.

*Primary Examiner* — John Ulm
(74) *Attorney, Agent, or Firm* — Saliwanchik, Lloyd & Eisenschenk

(57) ABSTRACT

The subject invention provides advantageous new salts of mu-opiate receptor peptides. These salts have been found to have excellent properties in terms of their crystal structure, stability, solubility, lack of impurities and/or the ability to be produced, with these advantageous properties, in amounts sufficient for the production of therapeutic compositions.

7 Claims, 46 Drawing Sheets

ADVANTAGEOUS SALTS OF μ-OPIATE RECEPTOR PEPTIDES

CROSS-REFERENCE TO A RELATED APPLICATION

The subject application is a continuation Application of copending application Ser. No. 12/744,859, filed on Jul. 22, 2010; which is a National Stage Application of International Application No. PCT/US2008/086838, filed on Dec. 15, 2008; which claims the benefit of U.S. Provisional Application Ser. No. 61/007,617, filed Dec. 13, 2007, all of which are incorporated herein by reference in their entirety.

The Sequence Listing for this application is labeled "September2010_ST25.txt", which was created on Sep. 30, 2010, and is 8 KB. The entire content is incorporated herein by reference in its entirety.

BACKGROUND OF INVENTION

1. Field of the Invention

This invention relates to salts of peptides that bind with high affinity and selectivity to the mu (morphine) opiate receptor; pharmaceutical preparations containing an effective amount of the peptide salts; and methods for providing analgesia, relief from gastrointestinal disorders such as diarrhea, and therapy for drug dependence containing an effective amount of the peptide salts.

2. Description of the Related Art

Many peptides have been found that exhibit opiate-like activity by binding to opiate receptors. Three different types of opiate receptors have been found: delta (δ), kappa (κ) and mu (μ). The major putative function for opiates is their role in alleviating pain. Other areas where opiates are well-suited for use in treatment are conditions relating to gastrointestinal disorders, schizophrenia, obesity, blood pressure, convulsions, and seizures. Although the δ and κ receptors may also mediate analgesia, activation of μ receptors is the primary and most effective means of inducing analgesia, and is the primary mechanism by which morphine acts.

Because morphine and other compounds with clinical usefulness act primarily at the receptor, pharmaceutical compositions having peptides with high affinity and selectivity for this site are of considerable importance. It would be desirable to produce these peptide compositions in a simple, efficient, and economical manner.

BRIEF SUMMARY

The subject invention provides advantageous new salts of mu-opiate receptor peptides. These salts have been found to have excellent properties in terms of their crystal structure, stability, solubility, lack of impurities and/or the ability to be produced, with these advantageous properties, in amounts sufficient for the production of therapeutic compositions.

Specifically exemplified herein are aspartate, maleate, lactate and hydrochloride salts of mu-opiate receptor peptides. In a particularly preferred embodiment, the subject invention provides hydrochloride salts of endomorphin peptides.

The peptides that can be used according to the subject invention have the general formula Tyr-$X_1$-$X_2$-$X_3$ wherein $X_1$ is Pro, D-Lys or D-Orn; $X_2$ is Trp, Phe or N-alkyl-Phe wherein alkyl contains 1 to about 6 carbon atoms; and $X_3$ is Phe, Phe-$NH_2$, D-Phe, D-Phe-$NH_2$ or p-Y-Phe wherein Y is $NO_2$, F, Cl or Br.

In a specific advantageous embodiment, the subject invention provides the hydrochloride salt of a cyclic endomorphin-1 peptide (designated herein as CYT-1010).

The subject invention further provides pharmaceutical compositions comprising these advantageous salts.

The subject invention further provides therapeutic methods that utilize the salts and compositions described herein.

The subject invention further provides methods for preparing the salts of the subject invention.

BRIEF DESCRIPTION OF SEQUENCES

Figure 1:
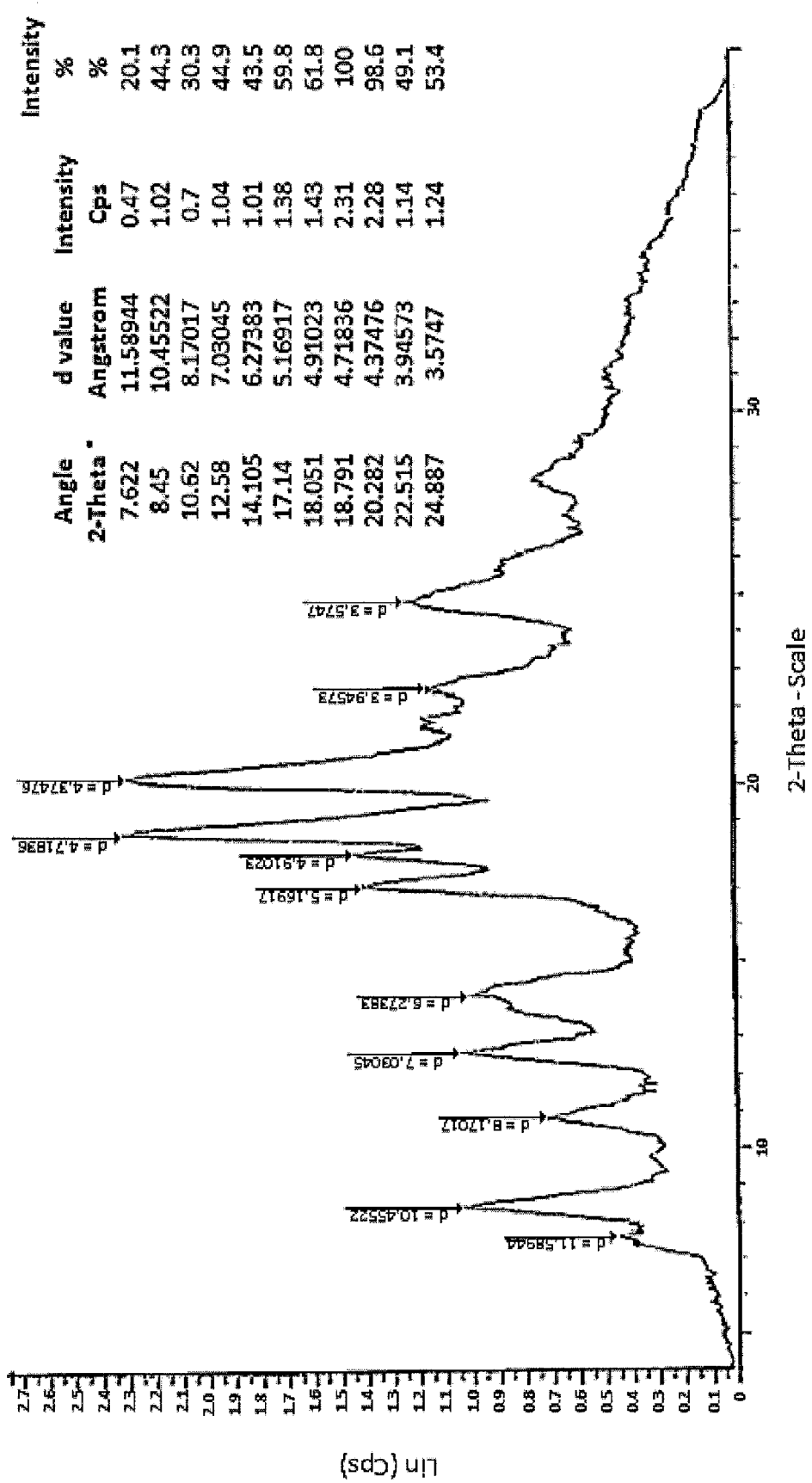
FIG. 1 shows x-ray diffractogram of CYT-1010 free base lot V05060N1.

SEQ ID NO:1 is a peptide useful according to the subject invention.
SEQ ID NO:2 is a peptide useful according to the subject invention.
SEQ ID NO:3 is a peptide useful according to the subject invention.
SEQ ID NO:4 is a peptide useful according to the subject invention.
SEQ ID NO:5 is a peptide useful according to the subject invention.
SEQ ID NO:6 is a peptide useful according to the subject invention.
SEQ ID NO:7 is a peptide useful according to the subject invention.
SEQ ID NO:8 is a peptide useful according to the subject invention.
SEQ ID NO:9 is a peptide useful according to the subject invention.
SEQ ID NO:10 is a peptide useful according to the subject invention.
SEQ ID NO:11 is a peptide useful according to the subject invention.
SEQ ID NO:12 is a peptide useful according to the subject invention.
SEQ ID NOS:13-26 are additional peptides useful according to the subject invention.

DETAILED DISCLOSURE

The subject invention provides advantageous salts of peptides that bind to the mu (morphine) opiate receptor with high affinity, selectivity and potency.

Advantageously, the salts of the subject invention have excellent properties in terms of their crystallinity, morphology, thermal properties, stoichiometry, hydroscopicity, aqueous solubility and/or chemical stability.

This invention also provides pharmaceutical preparations containing an effective amount of one or more of the peptide salts. The subject invention further provides methods for providing analgesia, relief from gastrointestinal disorders such as diarrhea, anti-inflammatory treatments, and therapy for drug dependence wherein the methods involve administering, to a patient in need of such treatment, a composition containing an effective amount of one or more of the peptide salts of the subject invention.

Initially, 16 salts of a cyclic endomorphin-1 peptide analog were selected for evaluation. These included fifteen monosalts and one hemisalt. Characterization of these salts on a 50 mg scale allowed the identification of four particularly advantageous salts: the aspartate, hydrochloride, maleate, and lactate salts.

The hydrochloride salt exhibited good crystallinity. The stoichiometry of the hydrochloride salt based on ion chromatography was close to theoretical. The monosalt appears to form a stable monohydrate at above 5% RH. Chemical stability appears excellent as well. Accordingly, in a particularly preferred embodiment, the subject invention provides the hydrochloride salt of endomorphin-1 (and analogs thereof) as well as pharmaceutical compositions that contain this salt.

Peptides

The peptides that can be used according to the subject invention have the general formula Tyr-$X_1$-$X_2$-$X_3$ wherein $X_1$ is Pro, D-Lys or D-Orn; $X_2$ is Trp, Phe or N-alkyl-Phe wherein alkyl contains 1 to about 6 carbon atoms; and $X_3$ is Phe, Phe-$NH_2$, D-Phe, D-Phe-$NH_2$ or p-Y-Phe wherein Y is $NO_2$, F, Cl or Br. Some preferred peptides of the invention are:

```
                                           (SEQ ID NO: 1)
H-Tyr-Pro-Trp-Phe-NH2

(SEQ ID NO: 2)
H-Tyr-Pro-Phe-Phe-NH2

(SEQ ID NO: 3)
H-Tyr-Pro-Trp-Phe-OH (SEQ ID NO: 4)
H-Tyr-Pro-Phe-Phe-OH (SEQ ID NO: 5)
H-Tyr-Pro-Trp-D-Phe-NH2

(SEQ ID NO: 6)
H-Tyr-Pro-Phe-D-Phe-NH2

(SEQ ID NO: 7)
H-Tyr-Pro-Trp-pNO2-Phe-NH2

(SEQ ID NO: 8)
H-Tyr-Pro-Phe-pNO2-Phe-NH2

(SEQ ID NO: 9)
H-Tyr-Pro-N-Me-Phe-Phe-NH2

(SEQ ID NO: 10)
H-Tyr-Pro-N-Et-Phe-Phe-NH2
```

```
                                             (SEQ ID NO: 11)
H-Tyr-Pro-N-Me-Phe-D-Phe-NH2

(SEQ ID NO: 12)
H-Tyr-Pro-N-Et-Phe-D-Phe-NH2

(SEQ ID NO: 13)
H-Tyr-c-[D-Lys-Trp-Phe]

(SEQ ID NO: 14)
H-Tyr-c-[D-Lys-Phe-Phe]

(SEQ ID NO: 15)
H-Tyr-c-[D-Orn-Trp-Phe]

(SEQ ID NO: 16)
H-Tyr-c-[D-Orn-Phe-Phe]

(SEQ ID NO: 17)
H-Tyr-c-[D-Lys-Trp-pNO2-Phe]

(SEQ ID NO: 18)
H-Tyr-c-[D-Lys-Phe-pNO2-Phe]

(SEQ ID NO: 19)
H-Tyr-c-[D-Orn-Trp-pNO2-Phe]

(SEQ ID NO: 20)
H-Tyr-c-[D-Orn-Phe-pNO2-Phe]

(SEQ ID NO: 21)
H-Tyr-c-[D-Lys-N-Me-Phe-Phe]

(SEQ ID NO: 22)
H-Tyr-c-[D-Orn-N-Me-Phe-Phe]

(SEQ ID NO: 23)
H-Tyr-c-[D-Lys-N-Et-Phe-Phe]

(SEQ ID NO: 24)
H-Tyr-c-[D-Orn-N-Et-Phe-Phe]

(SEQ ID NO: 25)
H-Tyr-c-[D-Lys-N-Me-Phe-D-Phe]

(SEQ ID NO: 26)
H-Tyr-c-[D-Lys-N-Et-Phe-D-Phe]
```

The last fourteen peptides listed are cyclic peptides whose linear primary amino acid sequences are given in SEQ ID NO:13 through SEQ ID NO:26. In this context, the applicants incorporate herein by reference, in its entirety, U.S. Pat. No. 6,303,578.

The peptide of SEQ ID NO:1 is highly selective and very potent for the .mu.opiate receptor, with over 4000-fold weaker binding to delta receptors and over 15,000-fold weaker binding to kappa receptors, reducing the chances of side-effects.

The peptides of this invention may be prepared by conventional solution-phase (Bodansky, M., *Peptide Chemistry: A Practical Textbook*, 2$^{nd}$ Edition, Springer-Verlag, New York (1993) or solid phase (Stewart, J. M.; Young, J. D. *Solid Phase Peptide Synthesis*, 2$^{nd}$ edition, Pierce Chemical Company, 1984) methods with the use of proper protecting groups and coupling agents. A suitable deprotection method may then be employed to remove specified or all of the protecting groups, including splitting off the resin if solid phase synthesis is applied.

Cyclization of the linear peptides can be performed by, for example, substitution of an appropriate diamino carboxylic acid for Pro in position 2 in the peptides through ring closure of the 2-position side chain amino and the C-terminal carboxylic functional groups. The cyclization reactions can be performed with the diphenylphosphoryl azide method (Schmidt, R., Neuhert, K., *Int. J. Pept. Protein Res.* 37:502-507, 1991).

Peptides synthesized with solid phase synthesis can be split off the resin with liquid hydrogen fluoride (HF) in the presence of the proper antioxidant and scavenger.

The amount of the reactants utilized in the reactions, as well as the conditions required to facilitate the reactions and encourage efficient completion may vary widely depending on variations in reaction conditions and the nature of the reactants.

The desired products may be isolated from the reaction mixture by crystallization, electrophoresis, extraction, chromatography, or other means. However, a preferred method of isolation is HPLC. All of the crude peptides can be purified with preparative HPLC, and the purity of the peptides may be checked with analytical HPLC. Purities greater than 95% of the synthesized compounds using HPLC have been obtained.

In a preferred embodiment specifically exemplified herein, the peptide is that which is shown as SEQ ID NO:13 (cyclic endomorphin-1 peptide) and has the following structure:

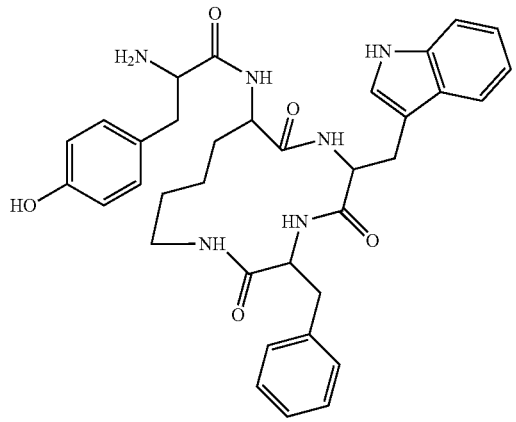 [SMILES: NC(Cc1ccc(O)cc1)C(=O)NC1CCCCNC(=O)C(Cc2ccccc2)NC(=O)C(Cc2c[nH]c3ccccc23)NC1=O]

Cyt 1010
$C_{35}H_{40}N_6O_5$
Mol. Wt: 624.73
C, 67.29; H, 6.45; N, 13.45; O, 12.81

Pharmaceutical Compositions

The present invention also provides pharmaceutical preparations that contain a pharmaceutically effective amount of the peptide salts of this invention and a pharmaceutically acceptable carrier or adjuvant. The carrier may be an organic or inorganic carrier that is suitable for external, enteral or parenteral applications.

The peptide salts of the present invention may be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems (Prokai-Tatrai, K.; Prokai, L; Bodor, N., *J. Med. Chem.* 39:4775-4782, 1991), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form, and in addition auxiliary, stabilizing, thickening and coloring agents and perfumes may be used.

Therapeutic Methods

The present invention also provides methods for providing analgesia, relief from gastrointestinal disorders such as diarrhea, and therapy for drug dependence in patients, such as mammals, including humans, which comprises administering to the patient an effective amount of the peptides, or salts thereof, of this invention. The diarrhea may be caused by a number of sources, such as infectious disease, cholera, or an effect or side-effect of various drugs or therapies, including those used for cancer therapy. For applying the peptide salts of the present invention to human, it is preferable to administer them by parenteral or enteral administration.

The peptide salts of the subject invention can also be used to provide anti-inflammatory treatments. In this context the applicants incorporate herein by reference, in its entirety, U.S. 2004/0266805.

The dosage of effective amount of the peptides varies from and also depends upon the age and condition of each individual patient to be treated. However, suitable unit dosages may be between about 0.01 to about 100 mg. For example, a unit dose may be from between about 0.2 mg to about 50 mg. Such a unit dose may be administered more than once a day, e.g. two or three times a day.

Experimental Methods

Morphology. A Zeiss Universal microscope configured with a polarized visible light source was used to evaluate the optical properties of the samples. Specimens were typically mounted on a microscope slide. Magnification was typically 125×. Observations of particle/crystal size and shape were recorded. The presence of birefringence was also noted.

Stoichiometry—$^1$H-NMR. Samples were prepared by dissolving 3-7 mg in dimethylsulfoxide (DMSO)-$d_6$ with 0.05% (v/v) tetramethylsilane (TMS). Spectra were collected at ambient temperature on a Varian Gemini 300 MHz FT-NMR spectrometer.

Stoichiometry—Ion Chromatography. Standards solutions were prepared generally in the 5 to 50 μg/mL range. The samples were dissolved and analyzed with a Dionex DX-600 ion chromatograph configured with a AminiPac PA 10 column for aspartic acid analysis and AS4A-SC/AG4A-SC column for maleic, hydrochloric and lactic acids and a conductivity detector.

Solubility. The solubility of the selected primary screen salts was determined at ambient temperature in aqueous buffer pH 7 by a visual technique. The solubility of the scaled-up salts was visually determined in aqueous pH 4.7 and 10 buffers both by the visual technique and HPLC analysis alongside with the stability samples using the same chromatographic condition (see section HPLC analysis).

Thermal Properties by Differential Scanning calorimetry (DSC). DSC data were collected on a TA Instruments 2910 DSC. In general, samples in the mass range of 1 to 10 mg were crimped in aluminum sample pans and scanned from 25° C. to past the melt at 10° C./minute using a nitrogen purse at 50 mL/min.

Thermal Properties by Thermogravimetric Analysis (TGA). TGA data were collected on a TA Instruments 2950 TGA. In general, samples in the mass range of 5 to 15 mg were placed in an open, pre-tared platinum sample pan and scanned from 25 to about 300° C. at 10° C./minute using a nitrogen purge.

Optical by Hot Stage Microscopy (HSM). A Zeiss Universal microscope configured with a polarized visible light source and a Mettler hot stage accessory was used to analyze CYT-1010 free base. A sample was mounted on a microscope slide with a drop of immersion oil and a cover glass. Magnification was 400×. Sample was heated from 25° C. to about 300° C. at 3 or 10° C./minute. Observations of phase change, recrystallization, evolution of bubbles, etc. were recorded.

Crystallinity by X-Ray Powder Diffraction (XRD). Diffraction patterns were collected using a Bruker D8 Discovery diffractometer configured with an XYZ stage, laser videomicroscope for positioning, and HiStar area detector. Collection times were 120 seconds at room temperature. A Cu Kα radiation 1.5406 Å tube was operated at 40 kV and 40 mA. The X-ray optics consist of a Gobel mirror coupled with a pinhole collimator of 0.5 mm. Theta-theta continuous scans were employed with a sample-detector distance of d 15 cm, which gives an effective 2θ range of 4-40°. Samples were mounted in low background quartz plates (9 mm diameter, 0.2 mm deep cavity).

Infrared Spectroscopy (FTIR). Infrared spectra were obtained with a Nicolet 510 M-O Fourier transform infrared spectrometer, equipped with a Harrick Splitpera™ attenuated total reflectance device. Spectra were acquired from 4000-400 $cm^{-1}$ with a resolution of 4 $cm^{-1}$, and 128 scans were collected for each analysis.

Solution Stability. The four final salt candidates were dissolved (in duplicate) in acetonitrile: water: (90:10) with 0.1% TFA at a concentration of 0.3 mg (free base basis) per mL of solvent. The scintillation vials were sealed. One vial of each salt solution was placed in a 40™C over for 2 weeks. Another vial of each salt solution was stored at 25° C. for 2 week. These solutions (and "time zero" solutions) were analyzed for CYT-1010 by HPLC.

Solid State Stability. Power samples of the four final salt candidates were transferred (in duplicate) to scintillation vials and sealed. One vial of each salt was placed in a 60° C. over for 2 week. Another vial of each salt was stored at 25° C. for 2 week. These samples (and "time zero" solutions) were analyzed for CYT-1010 by HPLC.

Photo Stability. Samples of the four final salt candidates were transferred (in duplicate) to crystallizing dishes and sealed with Saran® wrap. One dish of each salt was also covered with aluminum foil (as the dark controls). Another dish of each salt was not covered with aluminum foil (as the photoexposed samples). The samples were exposed to ICH compliant option 2 UV sources to examine their stability with respect to light at approximately 25° C. Dark controls and time zero samples were also analyzed for comparison. Samples were analyzed for CYT-1010 by HPLC.

Oxidation Stability. Samples of the four final salt candidates were exposed to a pure oxygen atmosphere for 2 weeks to examiner their stability with respect to oxidation at 25° C. Samples were analyzed for CYT-1010 by total area normalization for impurity profile by HPLC.

HPLC Analysis. Salt candidates were analyzed by total area normalization (TAN). The samples were dissolved in acetonitrile:water (90:10) with 0.1% TFA at a free base concentration of 0.3 mg/mL.

HPLC Conditions

HPLC column: YMC-Pack ODS-A 150 mm, 4.6 mm, 5 micron

Guard Column (optional) None

Column Temp: 25±1° C.

Sample Temp: ambient

Autosampler Flush: 1:1 Water:CAN

Flow Rate: 1.5 mL/min

Injection Volume: 7 μL

UV Detection: 215 nm

Run Time: 32 minutes

Analysis Time: 32 minutes

Mobil Phase: A—0.1% TFA in water

B—0.1% TFA in CAN

Gradient Puym Program*:

| Step Time (minutes) | Elapsed Time (minutes) | % A (Aqueous) | % B (organic) | Curve |
|---|---|---|---|---|
| 0.5 | 0.0 | 90 | 10 | 0 |
| 15.0 | 15.5 | 5 | 95 | 1 |
| 5.0 | 20.5 | 5 | 95 | 0 |
| 6.0 | 26.5 | 90 | 10 | 1 |
| 6.0 | 32.5 | 90 | 10 | 0 |

Dynamic Vapor Sorption (DVS) (Performed by Surface Measurement Systems Ltd., Allentown, Pa.). Samples were run in an automated dynamic vapor sorption analyzer from 0 to 95% relative humidity and back to 0% relative humidity at 25° C. in 5% RH steps. Samples were predried (to constant mass) under a dry nitrogen stream before analysis. Weight change as a function of humidity and time was recorded to construct a moisture isotherm and kinetic plot of water sorption and desorption. Sample masses were generally in the range of 1-5 mg.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Initial Evaluation

Fifteen acids were selected for detailed evaluation. The acids used during the study are shown in Table 1.

TABLE 1

Acetic
Aspartic (L)
Citric
Fumaric
Gluconic (D)
Hippuric
Hydrochloric
Lactic
Malic
Maleic
Mucic
Phosphoric
Sulfuric
Succinic
Tartaric (L)

Salts were initially prepared on an approximately 50 mg scale. The free base was suspended in methanol. All acids, except aspartic and mucic were dissolved in water. Equal molar portions of the free base and acid solutions were mixed to form the monosalts. Molar portions of the free base and half-molar acid solutions were mixed to form the hemisalt. Aspartic and mucic acid were added as dry powders as they were water-insoluble. Free base suspensions after additions of hydrochloric, sulfuric, maleic, phosphoric, tartaric, and citric acids became clear and were then evaporated while stirring on a stirplate at ambient temperature. The remaining cloudy salt preparations were left stirring capped for approximately two days to allow the reactions to occur, then evaporated the same way while stirring on a stirplate at ambient temperature. Salts were vacuum dried at 40° C.

Fifteen salts of the free base were prepared and evaluated for thermal properties and crystallinity. The different salt forms are shown in Table 2.

TABLE 2

Salt Forms Evaluated

| | | | |
|---|---|---|---|
| Acetate | Hippurate | Mucate | Tartrate (L) |
| Aspartate (L) | Hydrochloride | Phosphate | Gluconate (D) |
| Citrate | Lactate | Sulfate | Maleate |
| Fumarate | Malate (L) | Hemi-sulfate | Succinate |

Example 2

Characterization of Free Base

Figure 2:
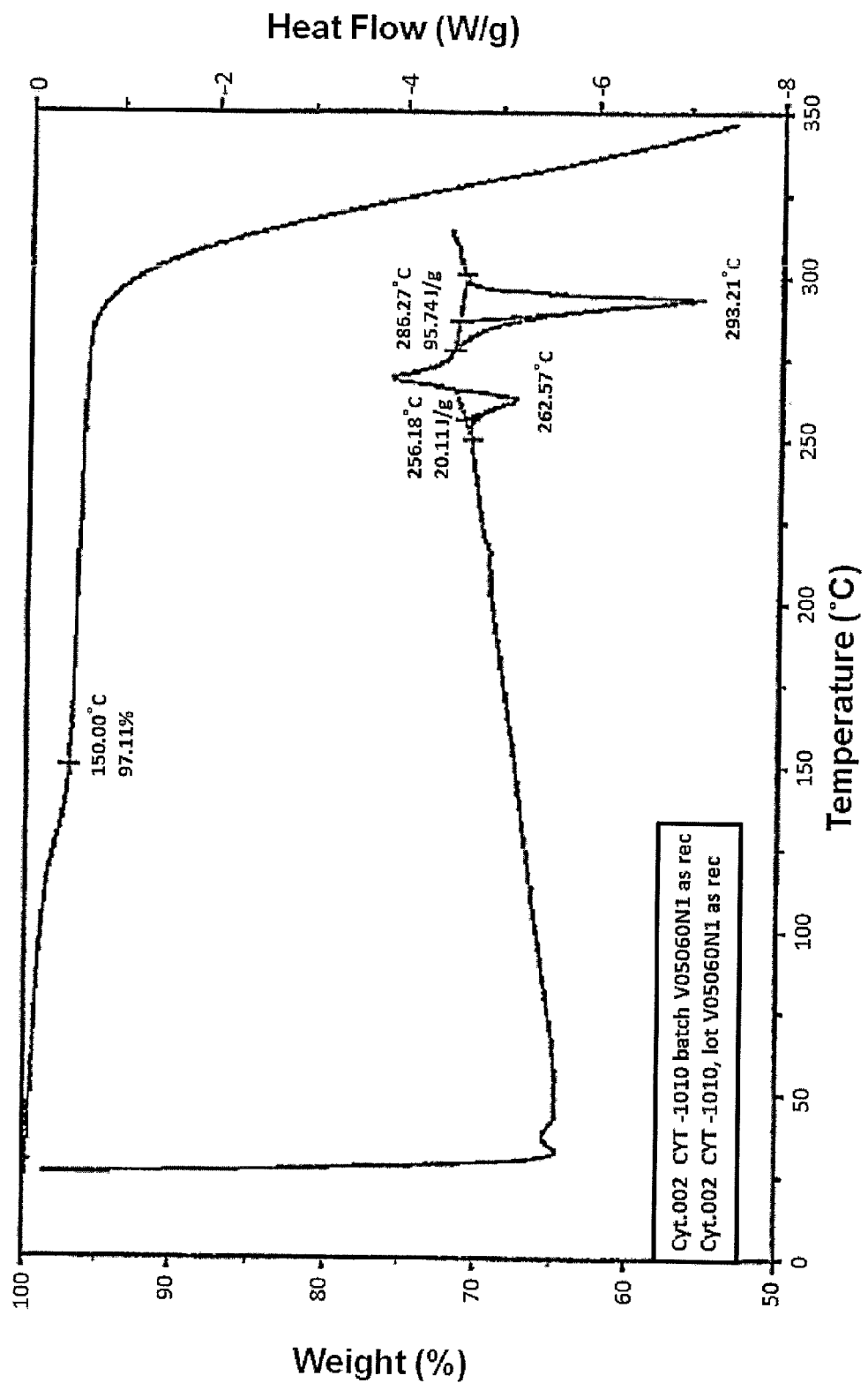
FIG. 2 shows DSC/TGA overlay of CYT-1010 free base lot V05060N1.

XRD analysis indicated that the free base was crystalline as shown in FIG. 1. An overlay of DSC and TGA thermograms can be seen in FIG. 2. The DSC thermogram exhibited multiple thermal events: a small endotherm with an onset temperature of 256.2° C. and an entalphy value of $\Delta H=20$ J/g immediately followed by a small exotherm. The second endothermic peak was a sharp peak with an onset temperature of 286.3° C. and an enthalpy value of 95.7 J/g. TGA thermogram exhibited the weight loss due to volatiles of 2.9 wt % (25° C.-150° C.).

Hot stage microscopy analysis indicated that the particles of the free base were irregularly shaped, platy and did not appear birefringent. The melting of the sample was completed by approximately 288° C. No other thermal events were evident.

Figure 3:
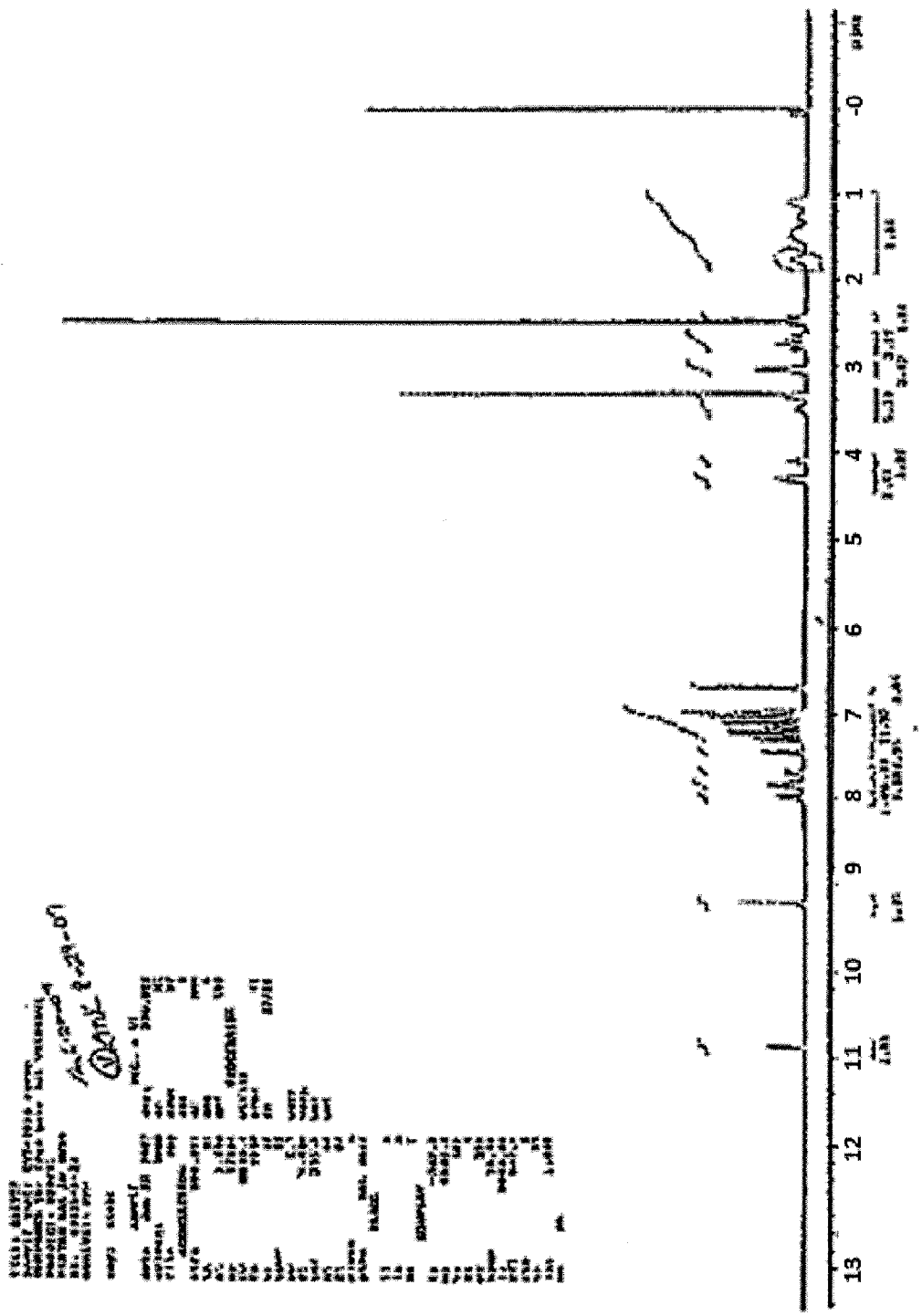
FIG. 3 shows H-NMR spectra of CYT-1010 free base lot V05060N1.
Figure 4:
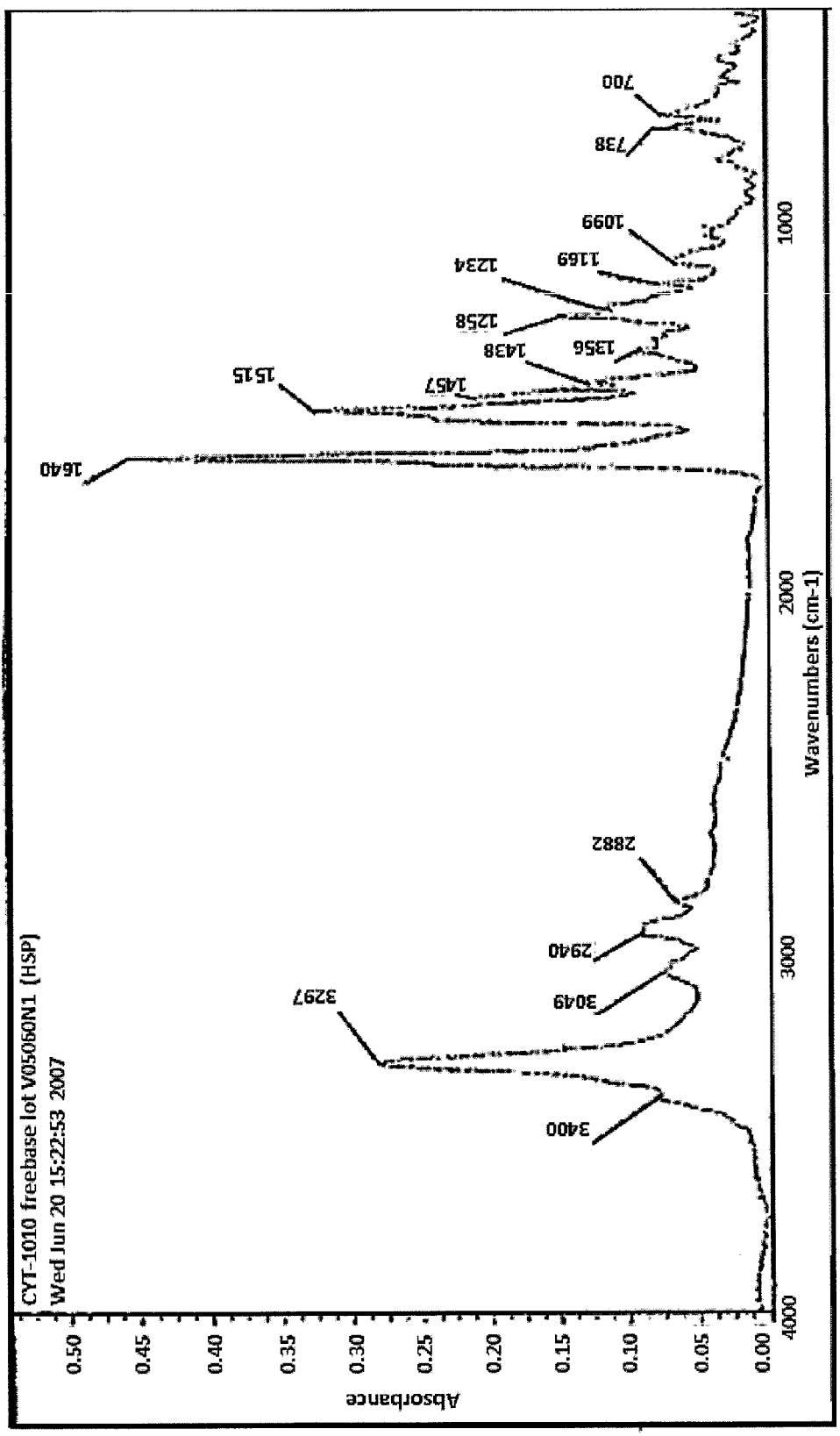
FIG. 4 shows FTIR spectrum of CYT-1010 free base lost V05060N1.

H-MHR and FTIR spectra of the free base are shown in FIG. 3 and FIG. 4, respectively.

Figure 5:
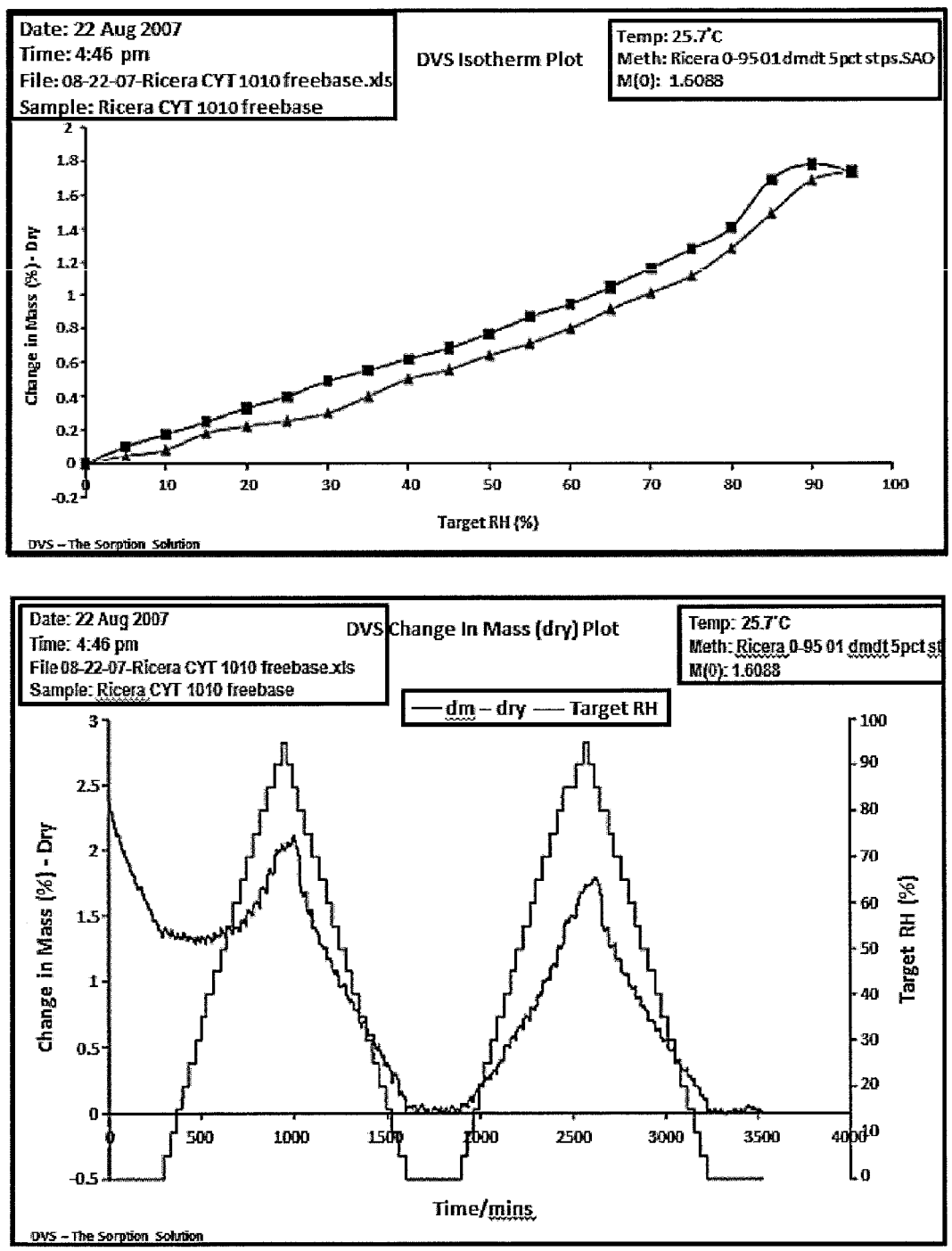
FIG. 5 shows DVS moisture isotherm of CYT-1010 free base.

DVS analysis of the free base indicated non-stoichiometric water uptake of up to 1.7 wt % by 90% RE (FIG. 5).

The stability data of the free base did not exhibit significant changes in HPLC-TAN values upon exposure to heat, light, or oxygen (Tables 6-9).

Example 3

Characterization of Primary Salts

Fifteen monosalts and one hemisalt were prepared and analyzed by powder X-ray diffraction. The thermal behavior of the primary salts was studied using DSC and TGA analysis. The analytical results are summarized in Table 3. As can be seen from the table, some salts were crystalline, others were low-ordered or amorphous. The crystallinity of some salts was improved by slurrying them in water for approximately a week. The thermal behavior of some salts was complex with the multiple thermal events observed on heating. Endotherms due to dehydration and/or desolvation for some of the salts were also evident.

TABLE 3

Crystallinity and Thermal Data of Selected Salts

| Salt | | Crystallinity by XRD | DSC results | TGA results (weight loss) |
|---|---|---|---|---|
| HCl | Mono | Low-ordered, was ripened by stirring in water, crystallintiy improved. | Small endotherm at 230° C. with ΔH = 10 J/g, melt with decomposition at 283° C. | Weight loss 3% by 150° C. |
| Sulfate | Hemi | Amorphous, was ripened by stirring in water, remained amorphous. | | |
| Sulfate | Mono | crystalline | Broad endotherm at ~100° C., melt with decomposition at 283° C. | Weight loss 5% by 150° C. and continued until melt |
| Aspartate (L) | Mono | Crystalline | Endotherm onset: 270° C., ΔH = 241 J/g (melt + decomposition). | 1.4% (25-150° C.). Stable weight up to 225° C. |
| Maleate | Mono | Low-ordered, was ripened by stirring in water, crystallinity improved. | Endotherm onset: 237° C., ΔH = 95 J/g | Weight loss 2.3% by 150° C., and dramatic wt. loss after 150° C. |
| Phosphate | Mono | Crystalline | Broad endotherm at ~200° C. with ΔH = 40 J/g, melt with decomposition at 308° | Weight loss 2.2% by 150° C., and dramatic wt. loss after 175° C. |
| Tartrate (L) | Mono | Crystalline | Broad endotherm at 86° C., small endotherm 139° C., with with decomposition at 252° C. | 2.0% (25-150° C.) |
| Fumarate | Mono | Crystalline | Endotherm onset: 263° C., ΔH = 111 J/g, | 5.3% (25-175° C.) |
| Mucate | Mono | Crystalline | A broad endotherm at ~75-100° C., a double endotherm at 207° C. | 2.7% (25-150° C.) |
| Citrate | Mono | Amorphous, was ripened by stirring in water, remained amorphous. | | |
| Malate (L) | Mono | Crystalline | Endotherm onset: 260.3° C., ΔH = 157 J/g, | 1.0% (25-150° C.), losing weight loss after 150° C. and up to the melt |
| Hippurate | Mono | Low-ordered, was ripened by stirring in water, crystallinity improved, but XRD pattern matched free base starting material, salt did not form. | | |
| Gluconate (D) | Mono | XRD pattern matched free base starting material, salt did not form. | | |
| Lactate (L) | Mono | Crystalline | Endotherm onset: 234° C., ΔH = 116 J/g, | 3.0% (25-150° C.) |
| Succinate | Mono | Low-ordered, was ripened by stirring in water, crystallinity improved. | A broad endotherm at ~75° C., a double endotherm at 248° C. | 2.5% (25-150° C.) |
| Acetate | Mono | Two samples generated: XRD of one sample matched free base, other sample was low-ordered. | | |

Solubility. The solubility of selected salts from the primary screen was determined. Solubility measurements were made at ambient temperature in an aqueous pH 7.0 buffer. The results of the solubility measurements are shown in Table 4. Even at a concentration of 0.05 mg/ml, the solutions were still cloudy for all salts indicating the solubility of all salts was <0.05 mg/mL. Solutions of the lactate, malate and aspartate salts appeared less hazy/cloudy than others, suggesting their solubility may be slightly higher than the other forms.

TABLE 4

Visual Solubility of Primary Salts in Aqueous pH 7.0 Buffer

| Salt | Visual Solubility (mg/ml) |
|---|---|
| Aspartate (L) | <0.05 |
| Tartrate (L) | <0.05 |
| Maleate | <0.05 |
| Malate | <0.05 |
| Phosphate | <0.05 |

TABLE 4-continued

Visual Solubility of Primary Salts in Aqueous pH 7.0 Buffer

| Salt | Visual Solubility (mg/ml) |
|---|---|
| Lactate (L) | <0.05 |
| Succinate | <0.05 |
| Hydrochloride | <0.05 |

The evaluation of the primary salts are summarized in Table 5. This evaluation allowed the selection of four salts for further evaluation: aspartate, hydrochloride, lactate and maleate.

TABLE 5

Summary of Salt Forms of the Primary Salt Screen

| Salt Form | Comments |
|---|---|
| Aspartate (L) | Single melting endotherm, small amount of volatiles, appears slightly more soluble than most other salts forms. |
| Maleate | Slightly more soluble than most other salt forms, TGA indicated thermal instability after 150° C. |
| Lactate (L) | Was not as soluble as some others, sample had 3% volatiles, single melting endotherm. |
| Hydrochloride | Crystallinity was improved by ripening, 3% volatiles, multiple events in DSC. |
| Tartrate (L) | XRD pattern was very similar to maleate, was slightly more soluble, but small additional endotherm in DSC trace could indicate polymorphic behavior. |
| Malate | XRD pattern was very similar to tartrate, was slightly more soluble, single endotherm, small amount of volatiles, but loss of weight after 150° C. |
| Succinate | Salt did not crystallize well, had to be ripened by slurring, one of the less soluble salts, sample had 2.5% volatiles, a double endotherm in DSC. |
| Sulfate | Sample had 5% volatiles. |
| Fumarate | TGA weight loss 5.3%. |
| Mucate | Not a promising salt based on thermal behavior. |
| Phosphate | One of the less soluble, multiple endotherms, weight loss profile is not good. |

Salt Screen Scale-Up. Based on the results of the primary salt screen, four monosalts were selected for a scale-up to the 400 mg scale: aspartate, hydrochloride, lactate and maleate. The same preparative procedure was used for the scale-up as was for the primary salt evaluation.

The characteristics of the four most promising salt forms are described below.

Aspartate

Figure 6:
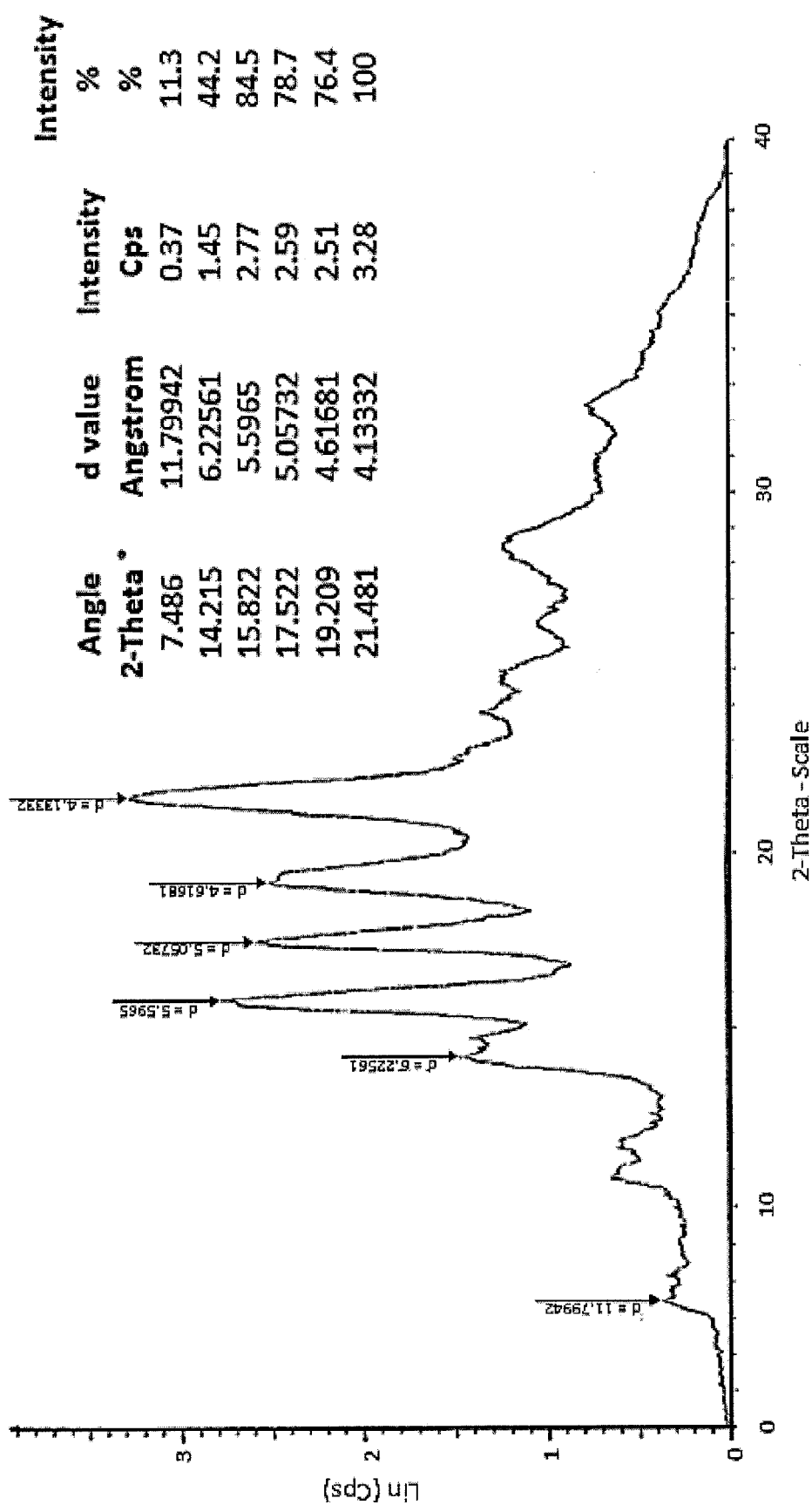
FIG. 6 shows x-ray diffractogram of the primary screen aspartate salt.
Figure 7:
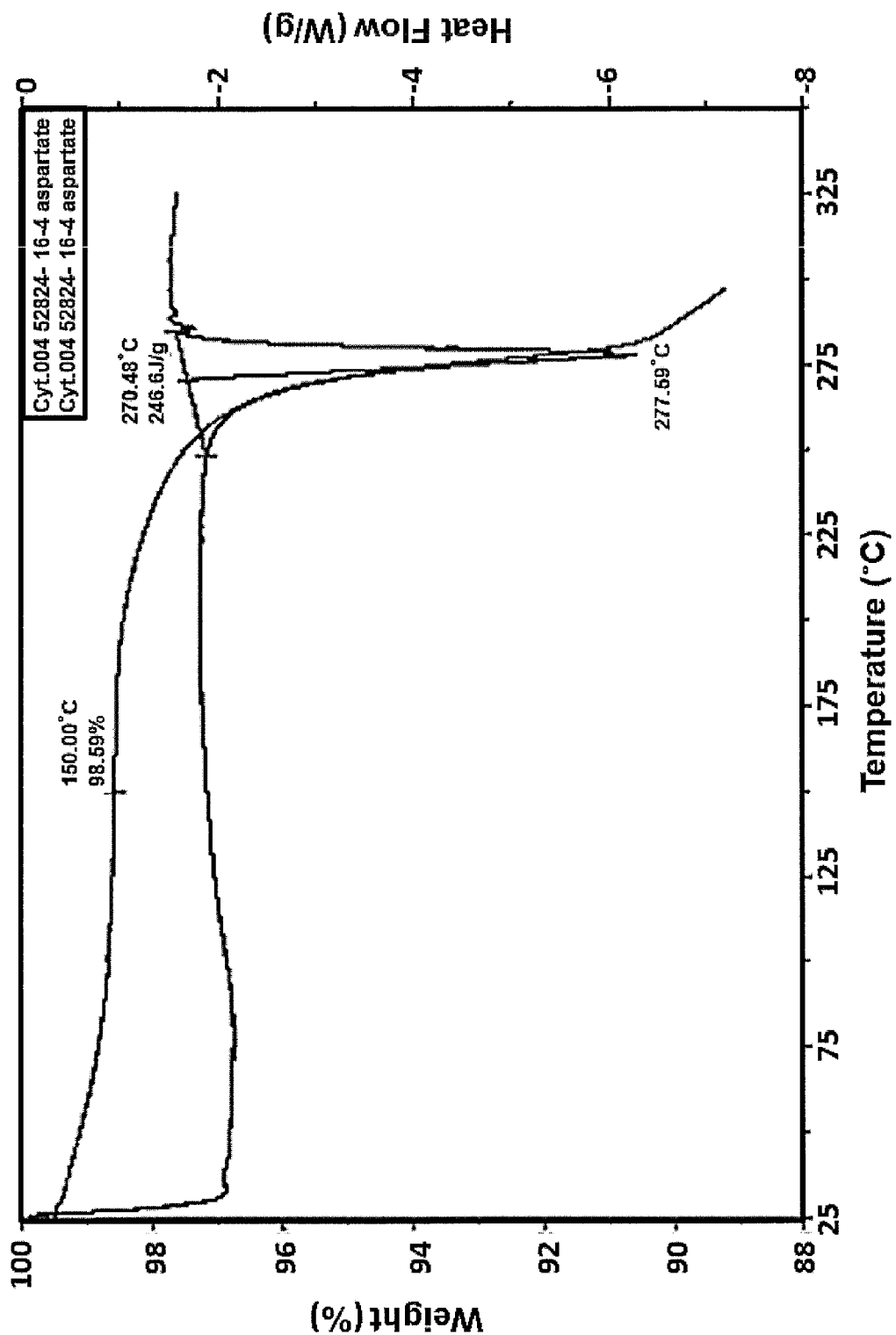
FIG. 7 shows DSC/TGA overlay of the primary screen aspartate salt.

The material was a white crystalline solid. The X-ray diffraction pattern of the batch is shown in FIG. 6. The DSC thermogram exhibited a melting endotherm with an extrapolated onset temperature of approximately 270° C. It appears to melt with decomposition. The total volatiles by TGA in a temperature range 25-150° C. were 1.4 wt %. A DSC/TGA overlay plot is shown in FIG. 7.

Hydrochloride

Figure 8:
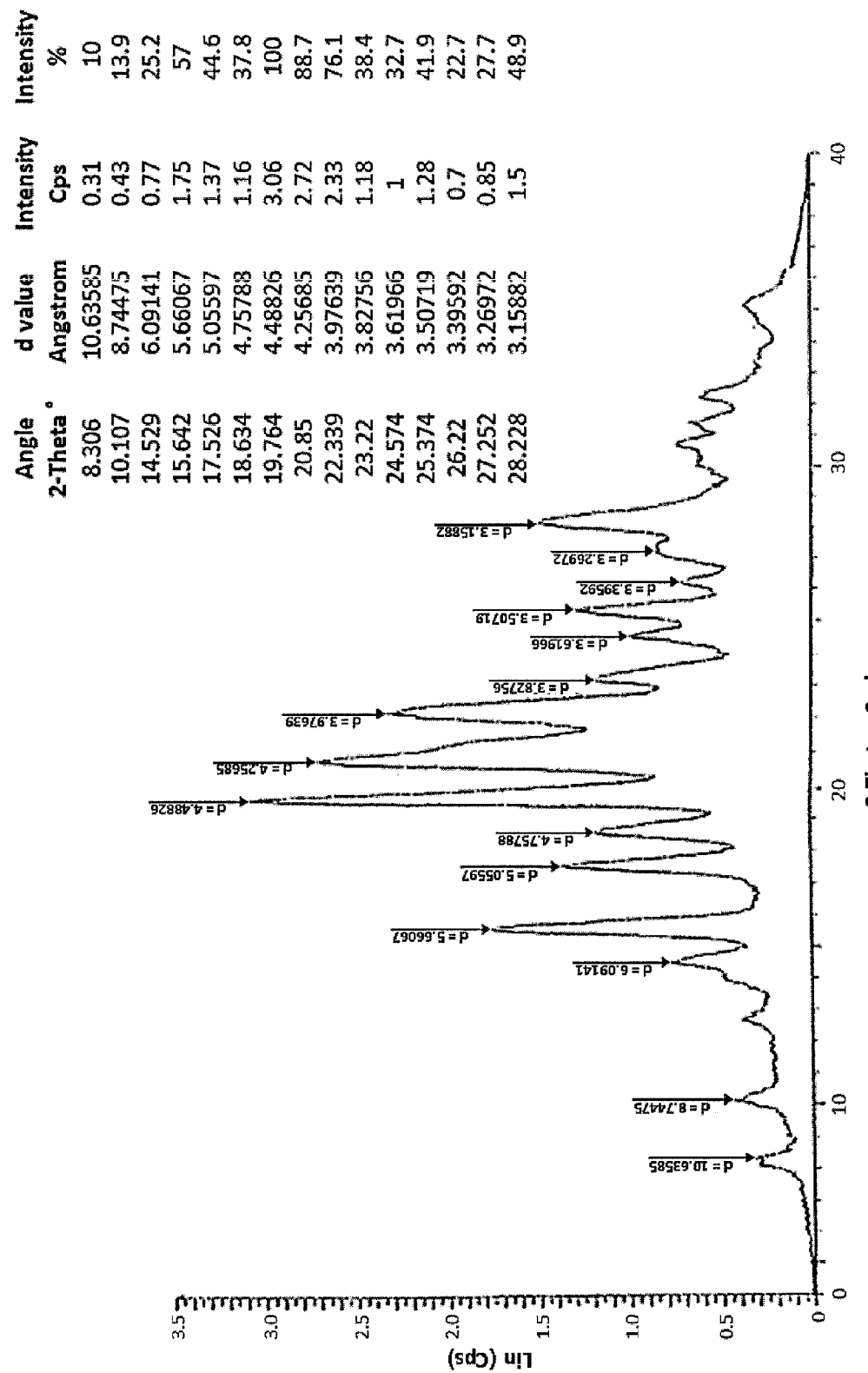
FIG. 8 shows x-ray diffractogram of the primary screen hydrochloride salt.
Figure 9:
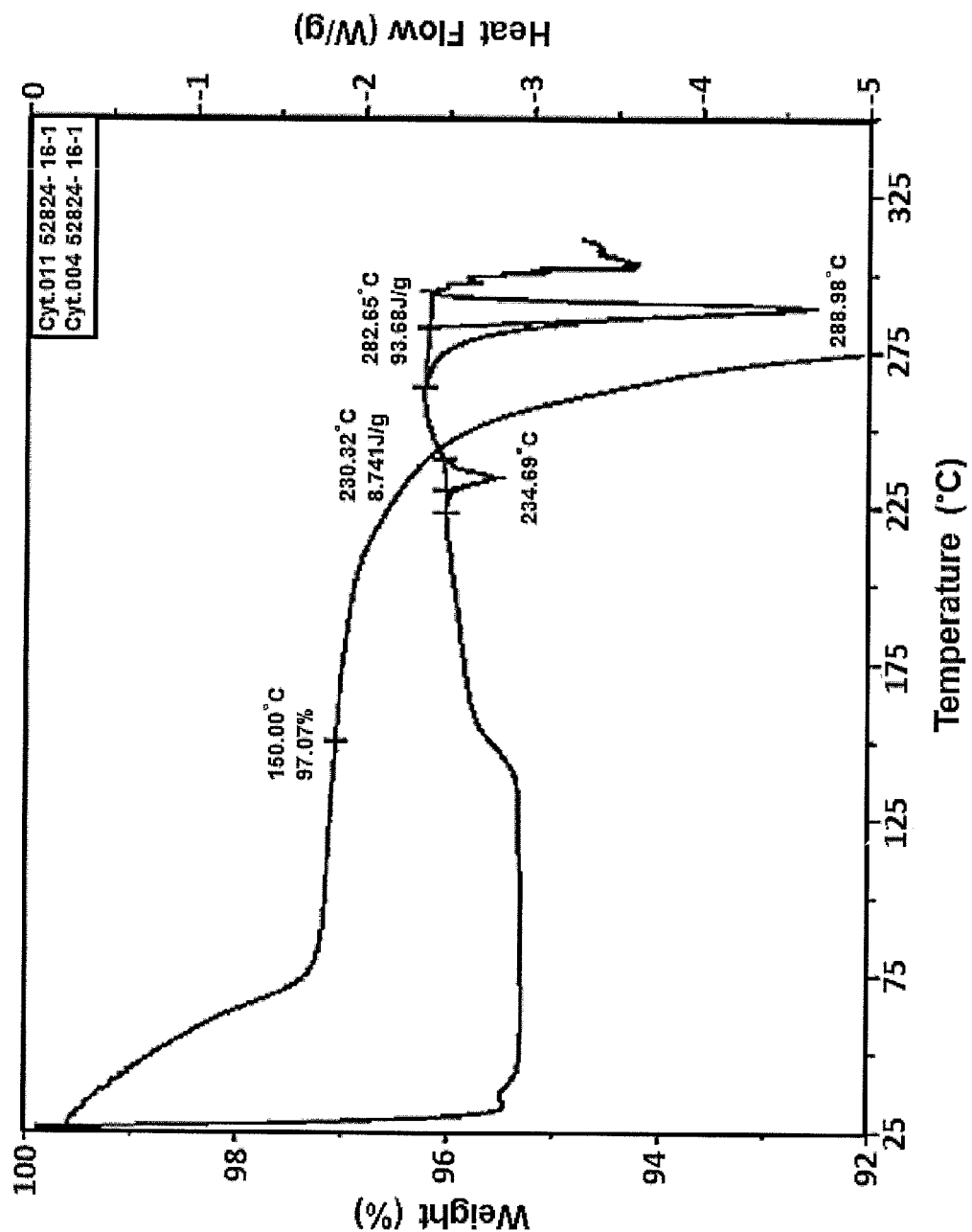
FIG. 9 shows DSC/TGA overlay of the primary screen hydrochloride salt.

The hydrochloride salt isolated was a white crystalline solid. The X-ray diffraction pattern of the batch is shown in FIG. 8. The material exhibited a small (8 J/g) endotherm with an onset temperature of 230° C. and the main endotherm with an onset of 282.7° C. (the DSC/TGA overlay is shown in FIG. 9). The weight loss observed using TGA at 150° C. was 2.9 wt %.

Lactate

Figure 10:
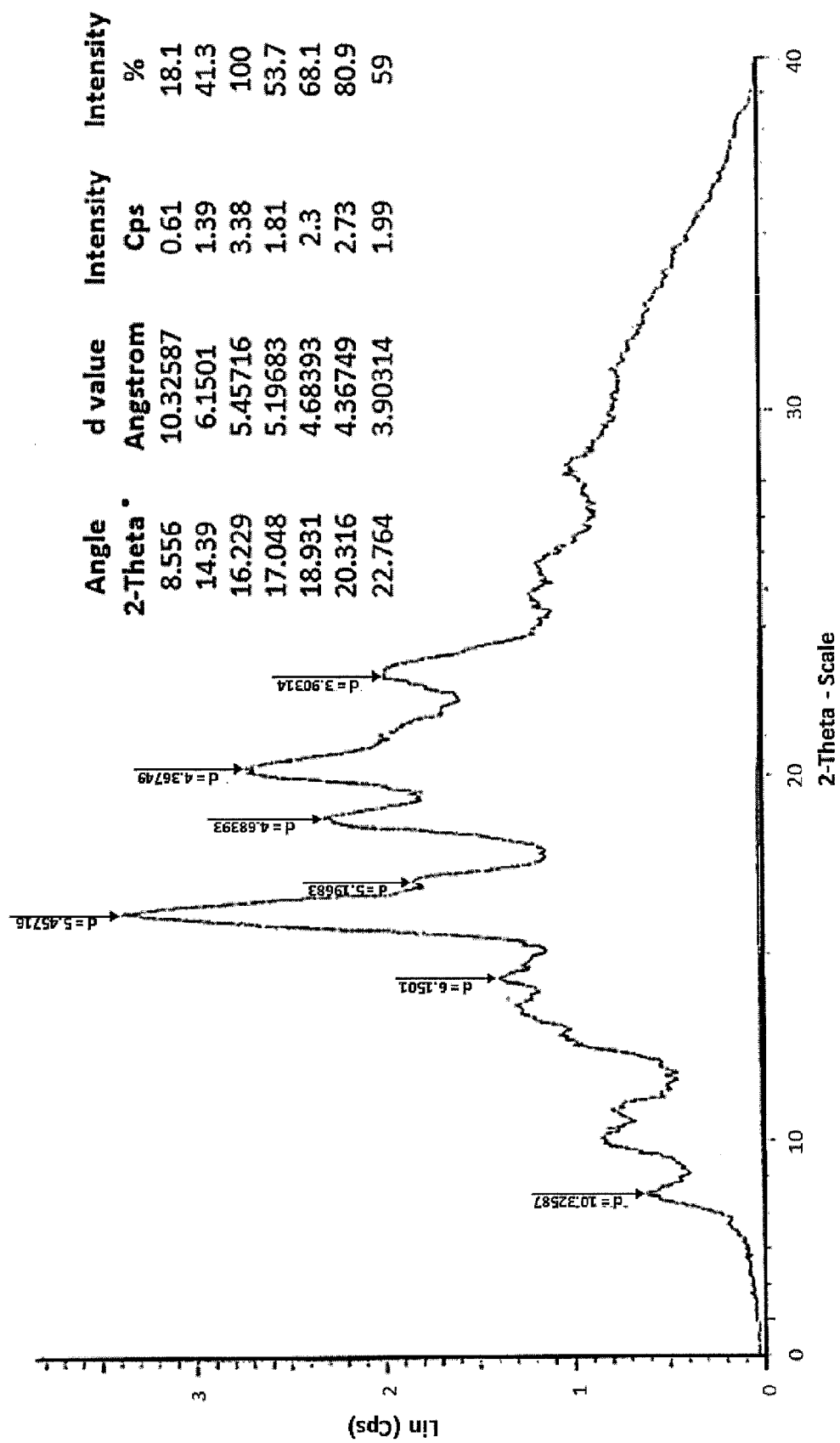
FIG. 10 shows x-ray diffractogram of the primary screen lactate salt.
Figure 11:
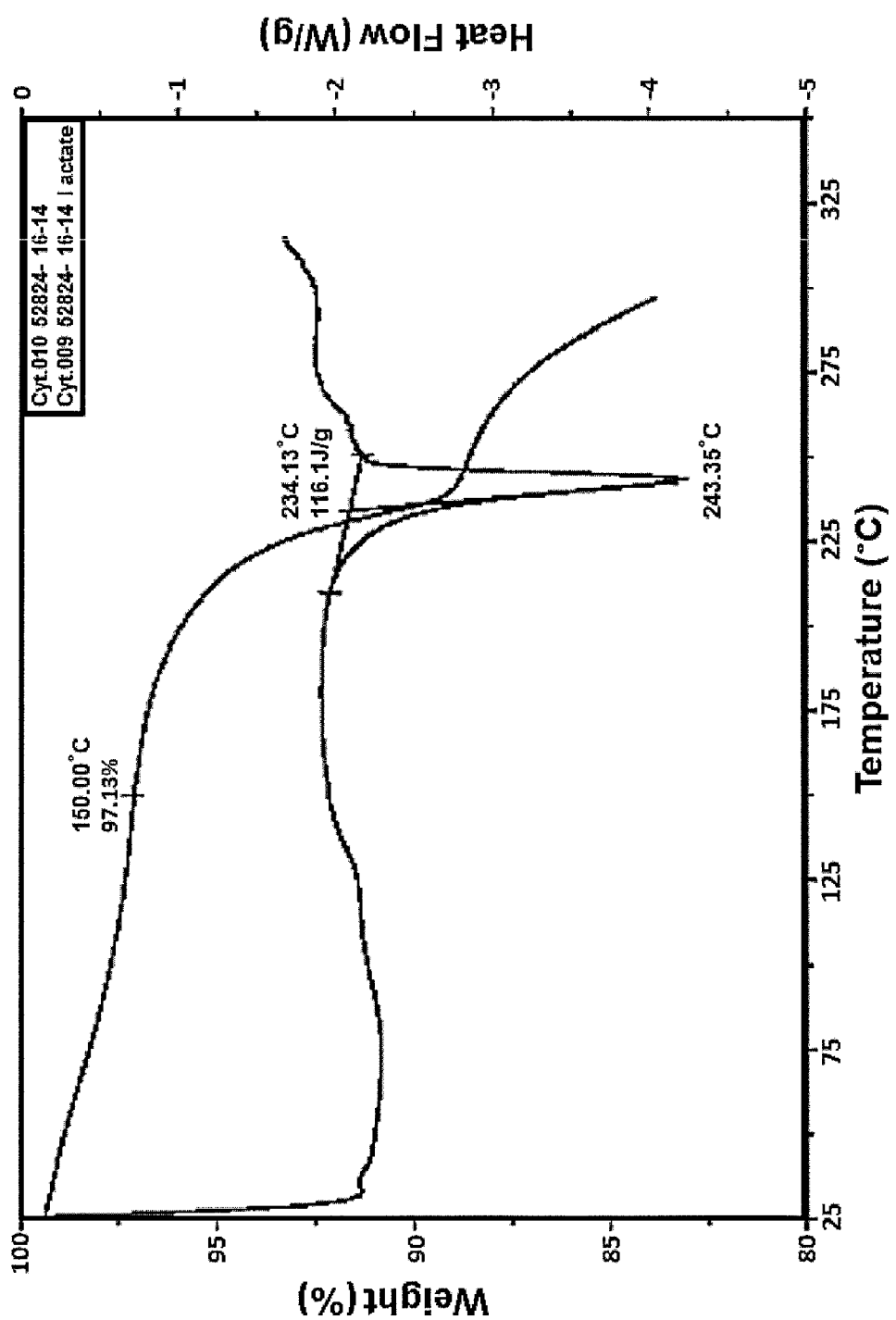
FIG. 11 shows DSC/TGA overlay of the primary screen lactate salt.

The XRD pattern of the lactate salt is shown in FIG. 10, it was less crystalline than the aspartate or hydrochloride. It was a white solid. The DSC thermogram revealed a single melting endotherm with an onset temperature of 234° C. and an entalphy value of 116 J/g. The sample lost approximately 2.9 wt % at 150° C. by TGA as shown in FIG. 11.

Maleate

Figure 12:
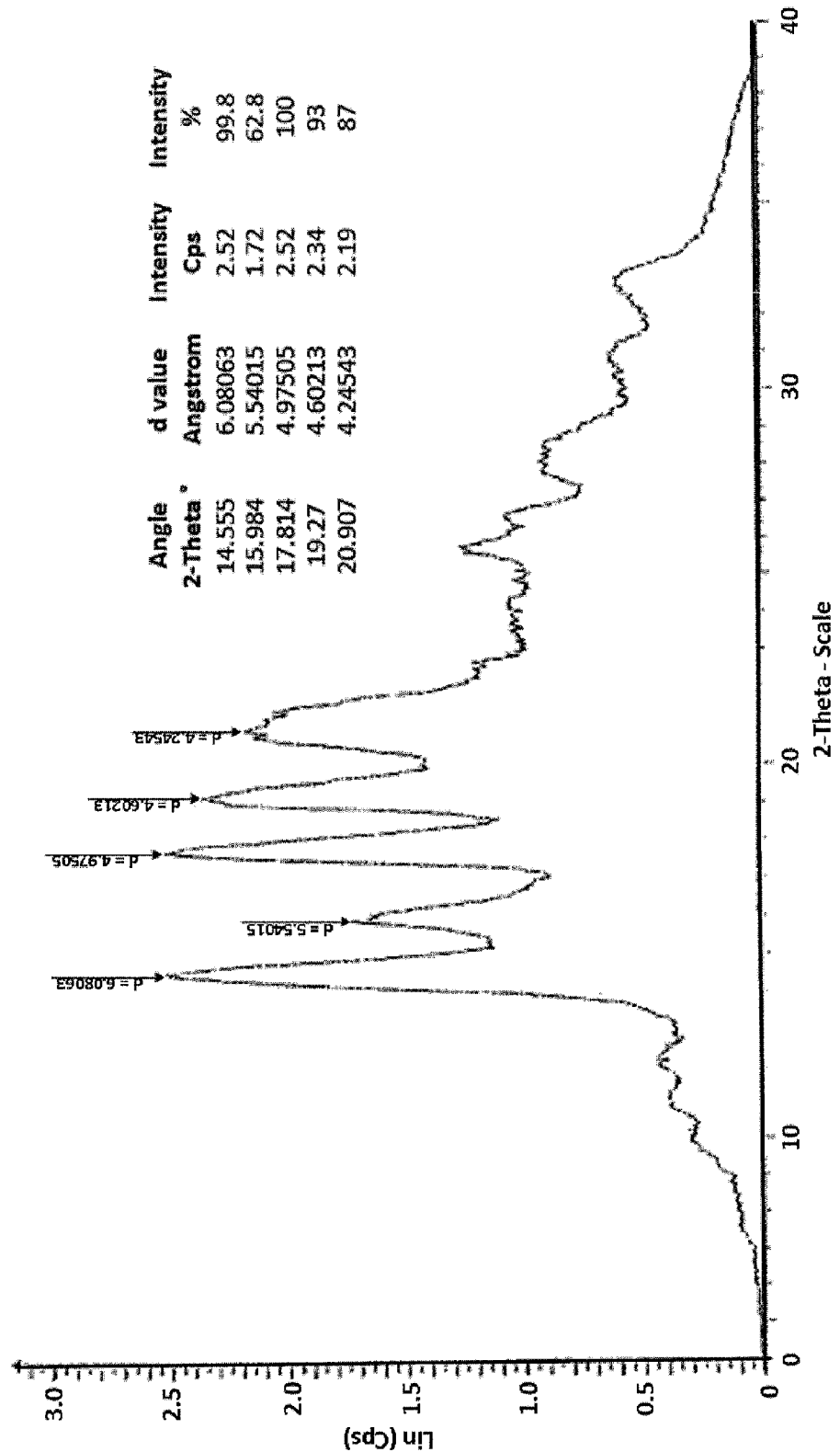
FIG. 12 shows x-ray diffractogram of the primary screen maleate salt.
Figure 13:
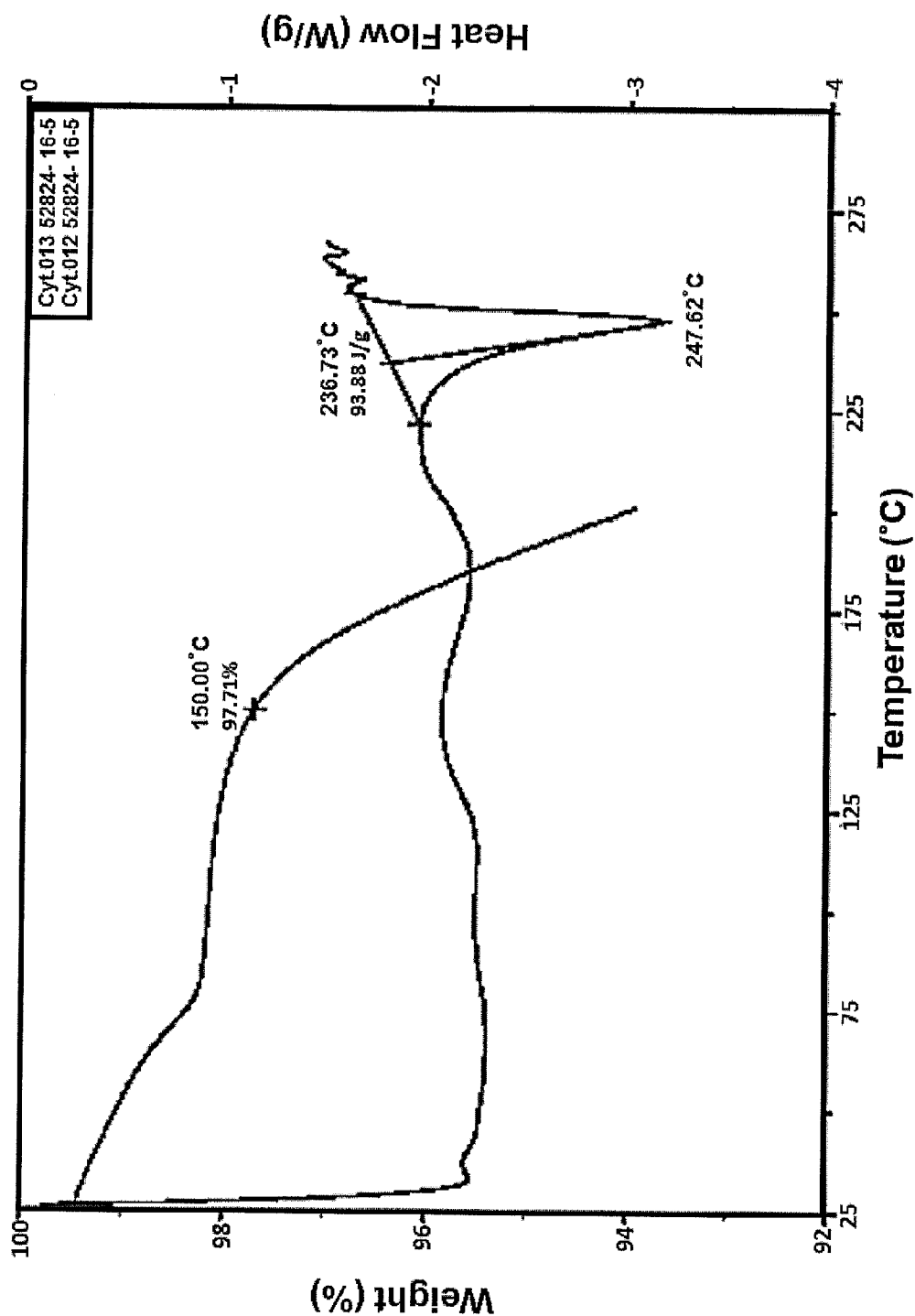
FIG. 13 shows DSC/TGA overlay of the primary screen maleate salt.

The malate was a slightly off-white crystalline solid, the XRD pattern is shown in FIG. 12. The DSC thermogram had an endotherm with an onset temperature of 236.7° C. and a heat of fusion 93.9 J/g. The TGA thermogram indicated a weight loss of 150° C. of 2.3 wt % but the sample started to loose mass at approximately 150° C. The DSC/TGA thermogram overlay plot is shown in FIG. 13.

Example 4

Characterization of Scaled-Up Salts

After the initial evaluation, additional amounts of four salts (aspartate, hydrochloride, lactate, and maleate) were prepared for further evaluation. These salts were scaled up to approximately 400 mg to facilitate additional testing and determine if the characteristics of the solids were reproducible. The results of the scaled-up analyses are summarized below.

Aspartate. The material produced in the scale-up batch was analyzed by XRD, DSC, TGA, H-NMR, and FTIR.

Figure 14:
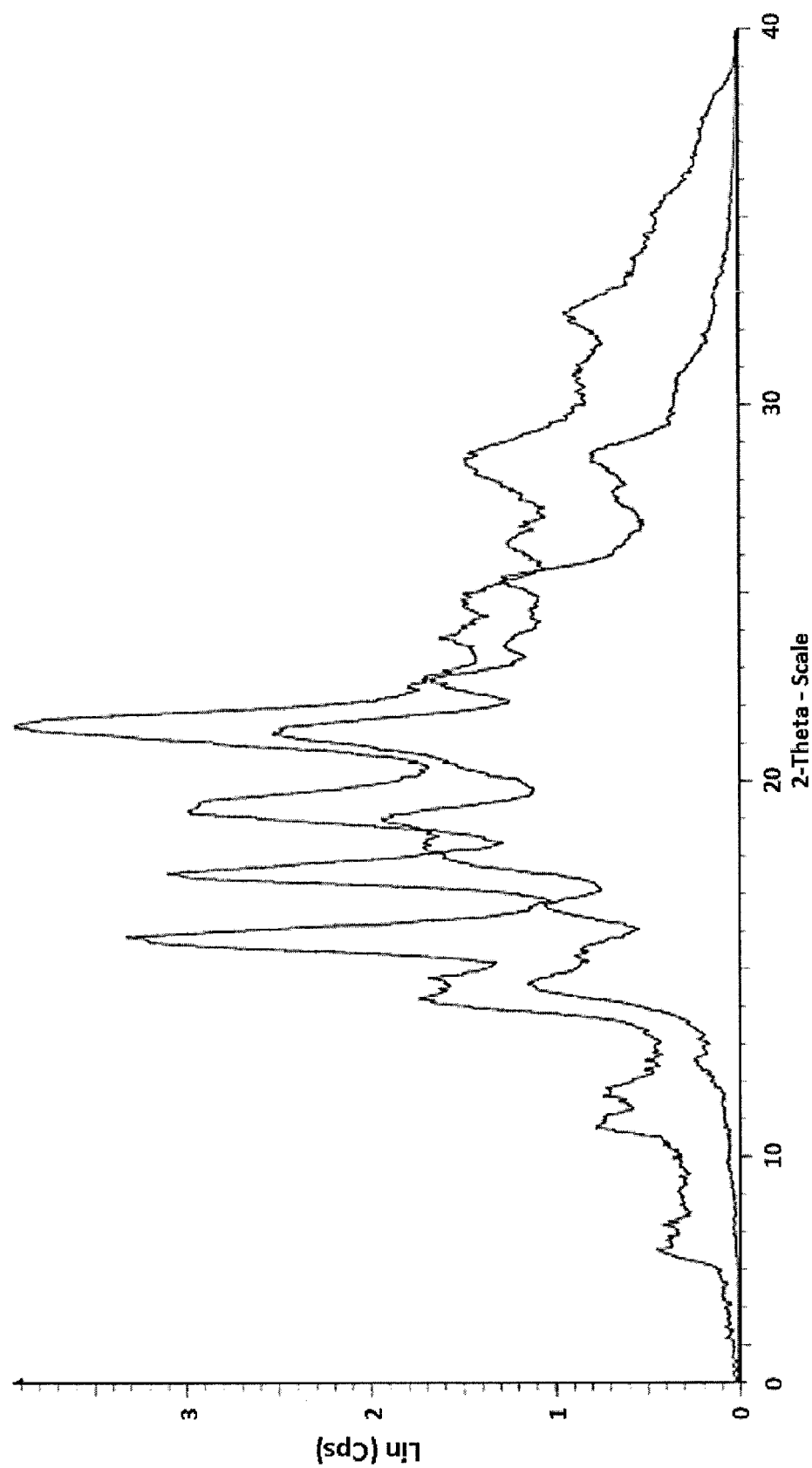
FIG. 14 shows x-ray diffractograms of the aspartate salt: primary screen sample (blue trace), scaled-up sample (black trace).
Figure 15:
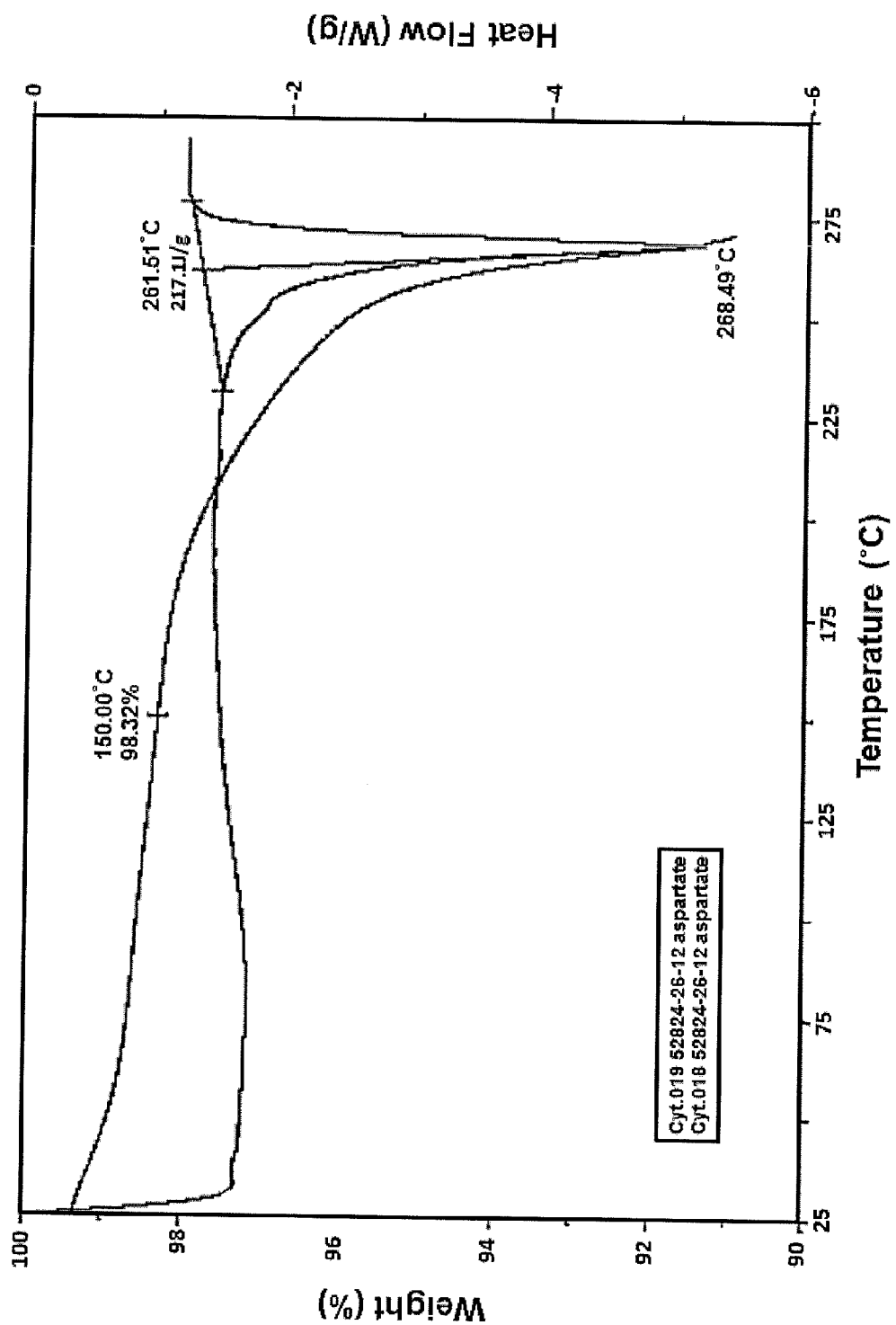
FIG. 15 shows DSC/TGA thermograms of the scaled-up sample aspartate salt.
Figure 16:
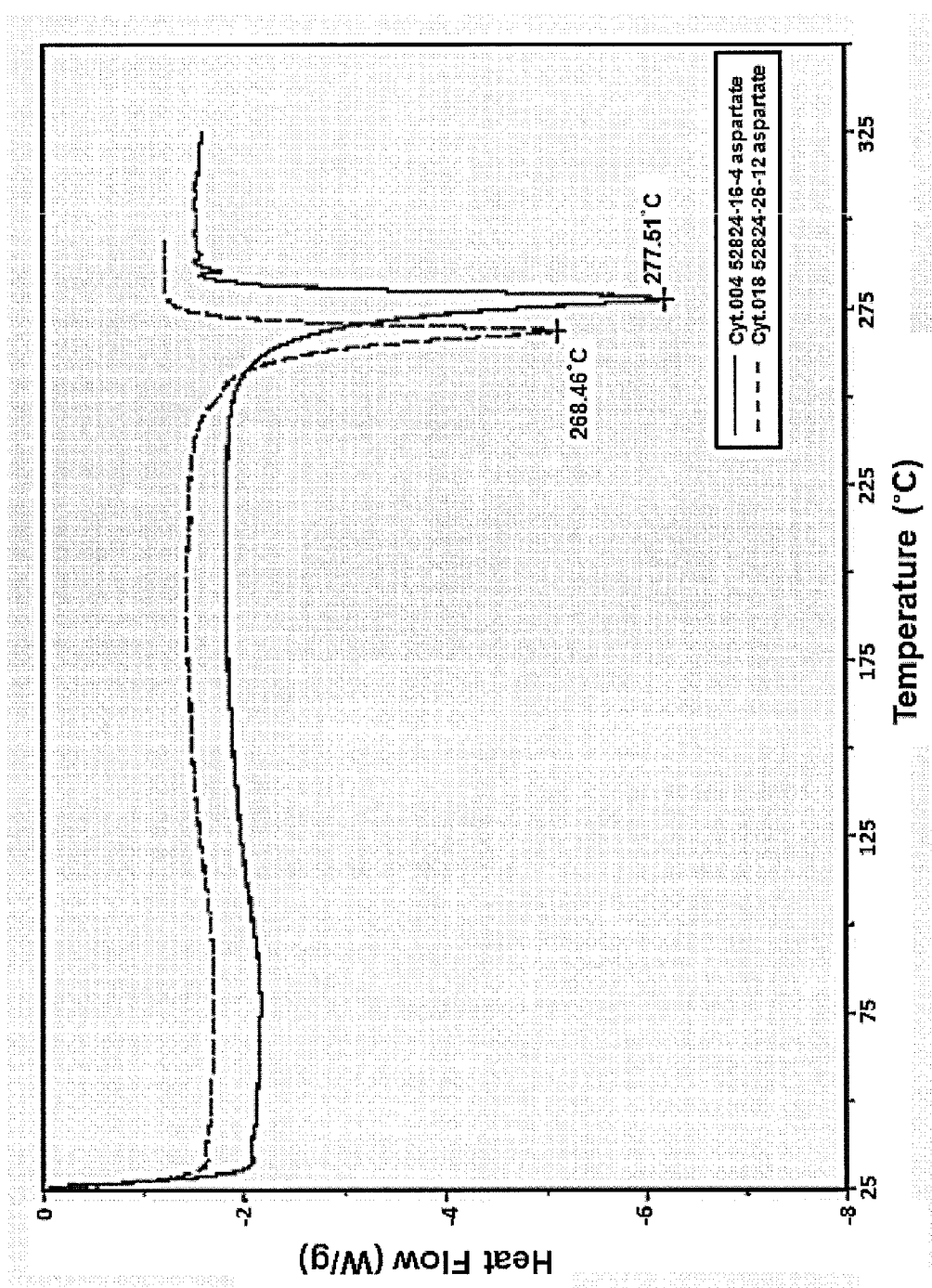
FIG. 16 shows DSC overlay of the primary screen sample (upper trace) and the scaled-up sample (lower trace) of the aspartate salt.

XRD overlay of the scaled-up aspartate salt (black trace) with a small scale batch (blue) is shown in FIG. 14. The DSC/TGA data for the scaled-up aspartate is shown in FIG. 15. FIG. 16 shows the DSC overlay plot of the small scale sample with the scaled-up sample. The scaled-up sample appears to be less crystalline than the small scale sample despite the fact that the additional ripening in water was done to improve crystallinity. The DSC thermogram shows a single melt with an earlier melting onset than the small scale sample, provably due to the lower crystallinity. The sample had 1.7 wt % volatiles.

The aspartic acid content determined by ion chromatography was approximately 13.5 wt %, somewhat lower than the theoretical value for monosalt (17.6 wt %). This may have contributed to the lower crystallinity of the sample.

Figure 17:
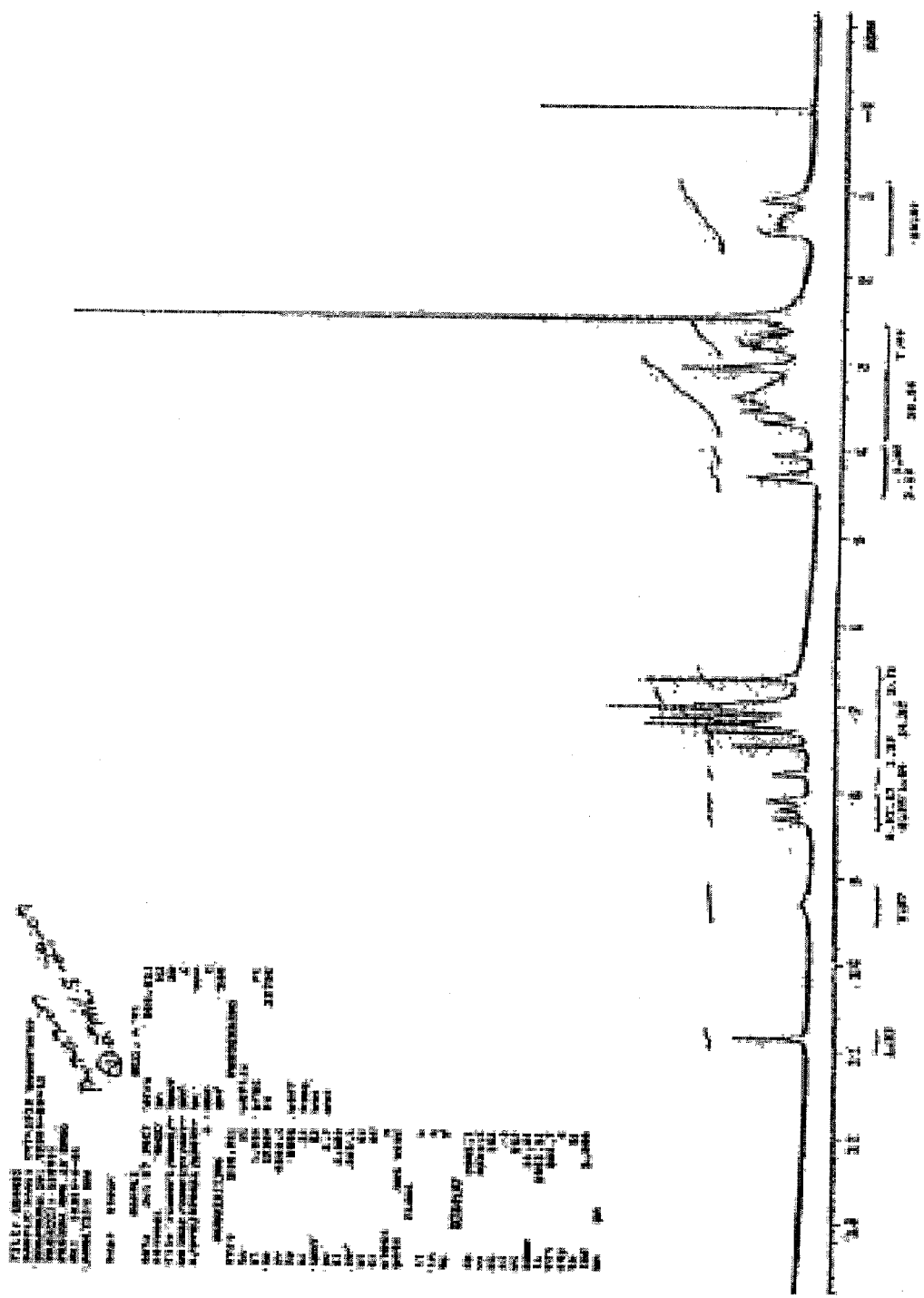
FIG. 17 shows H-NMR spectra of the scaled-up sample aspartate salt.

The proton FT-NRM spectrum of the aspartate was collected and is shown in FIG. 17. The aspirate aliphatic peaks were over lapped by the CYT-1010 aliphatic peaks, so that molar ratio could not be determined by NMR.

Figure 18:
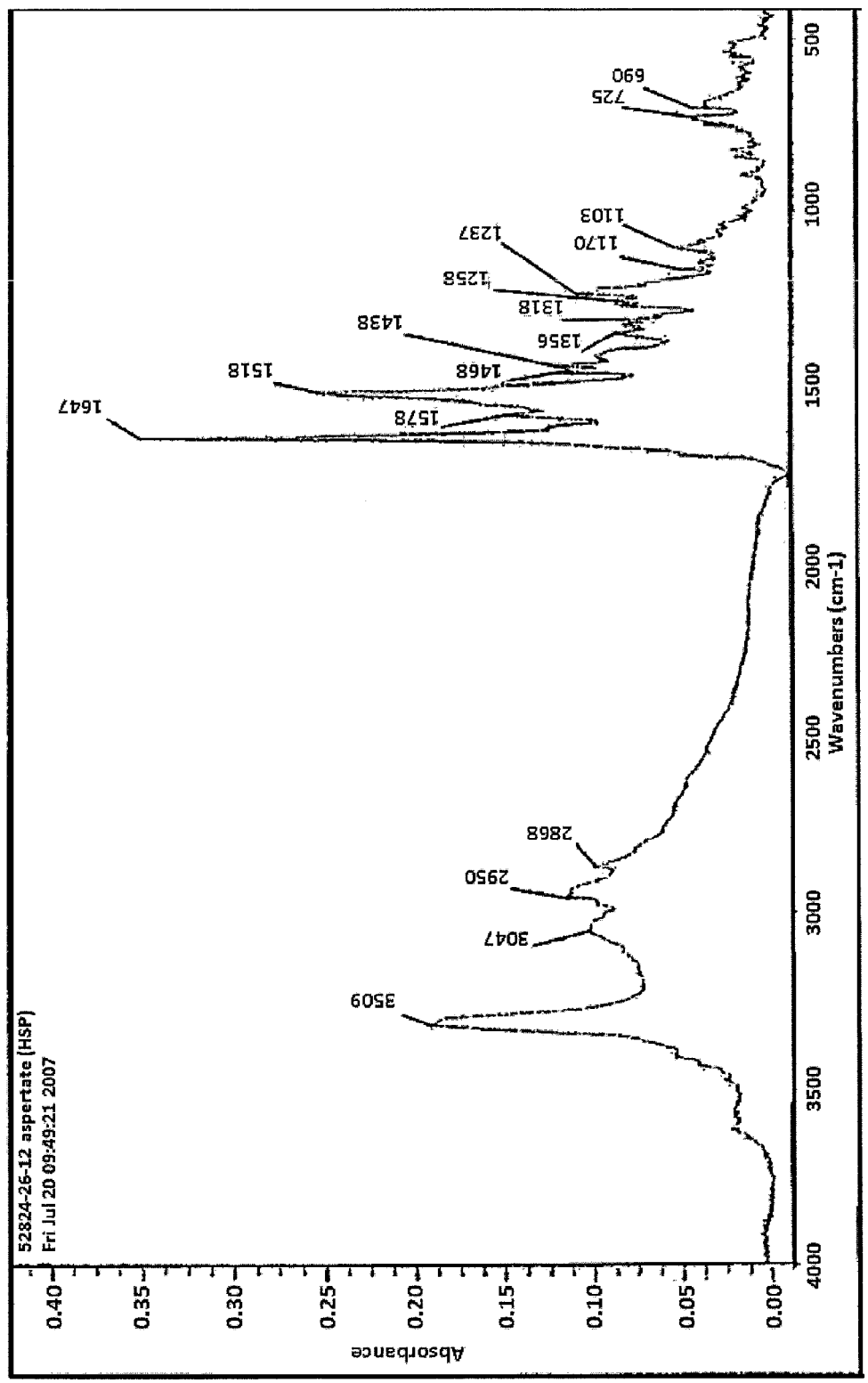
FIG. 18 shows FTIR spectrum of the scaled-up aspartate.

The FTIR spectrum of the scaled-up aspartate is shown in FIG. 18.

Figure 19:
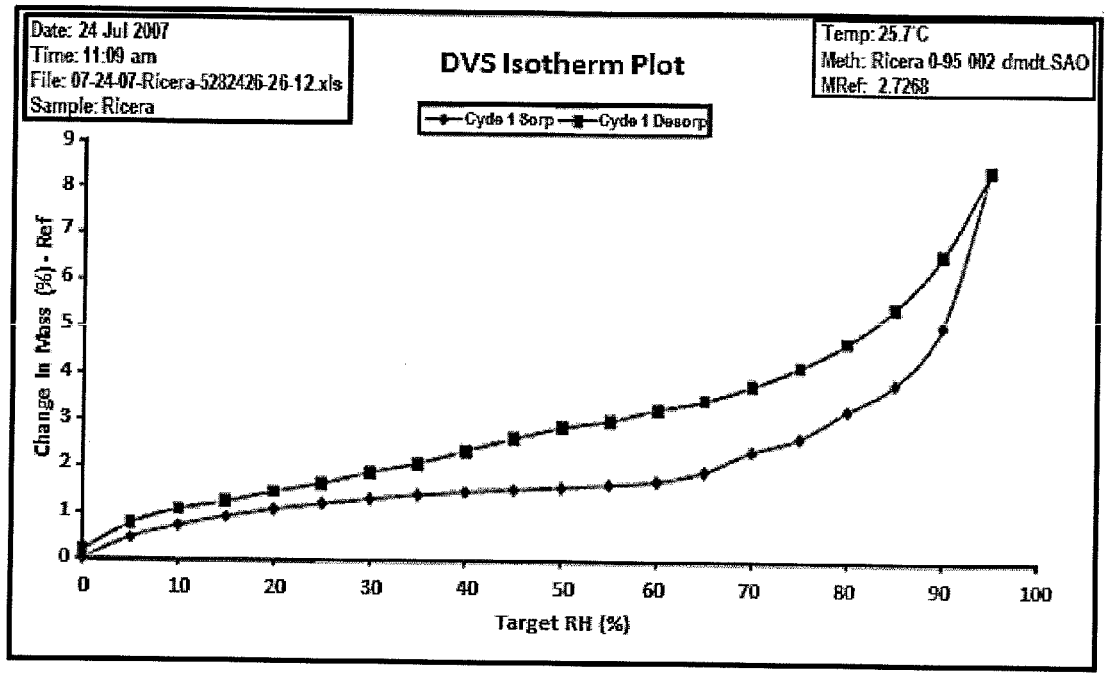
FIG. 19 shows DVS moisture isotherm of the scaled-up aspartate.
Figure 19:
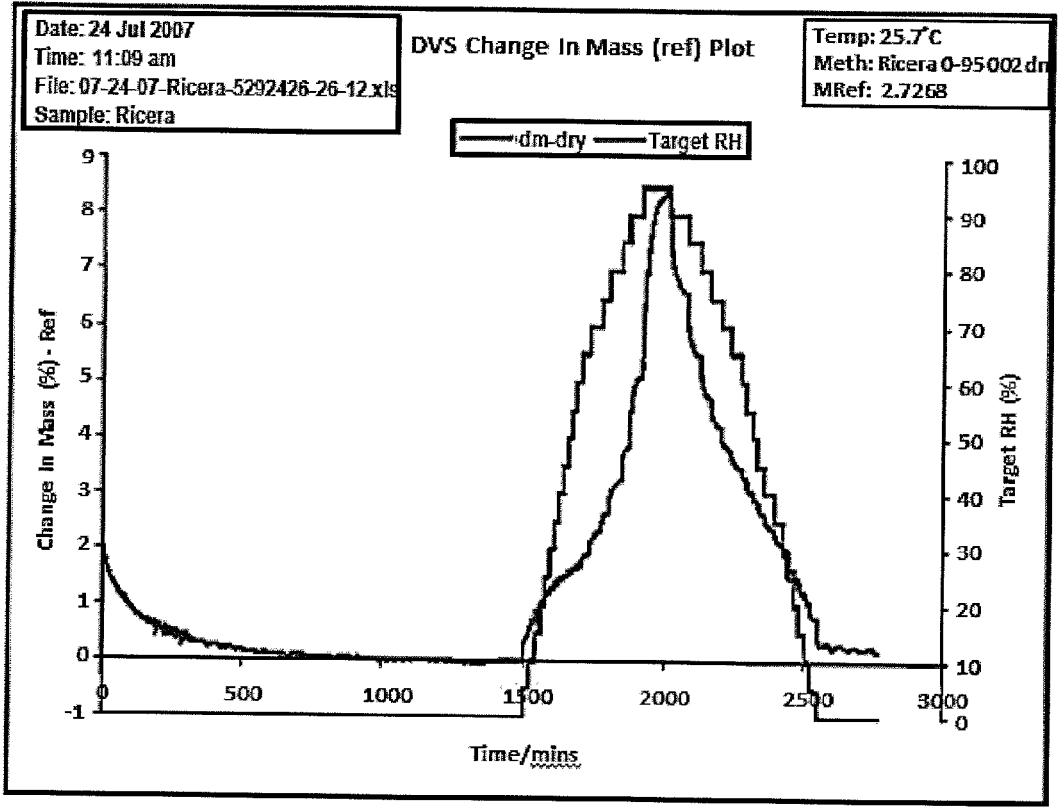

DVS analysis of the scaled-up aspartate salt was performed. The aspartate salt may form a hemihydrate then monohydrate at higher humidity. The moisture sorption isotherm and kinetic data plot are shown in FIG. 19. The shape of the isotherm plot makes it difficult to be certain whether hydrates form.

The aqueous solubility results at pH 4, pH 7, pH 10 are shown in Table 10.

Hydrochloride

Figure 20:
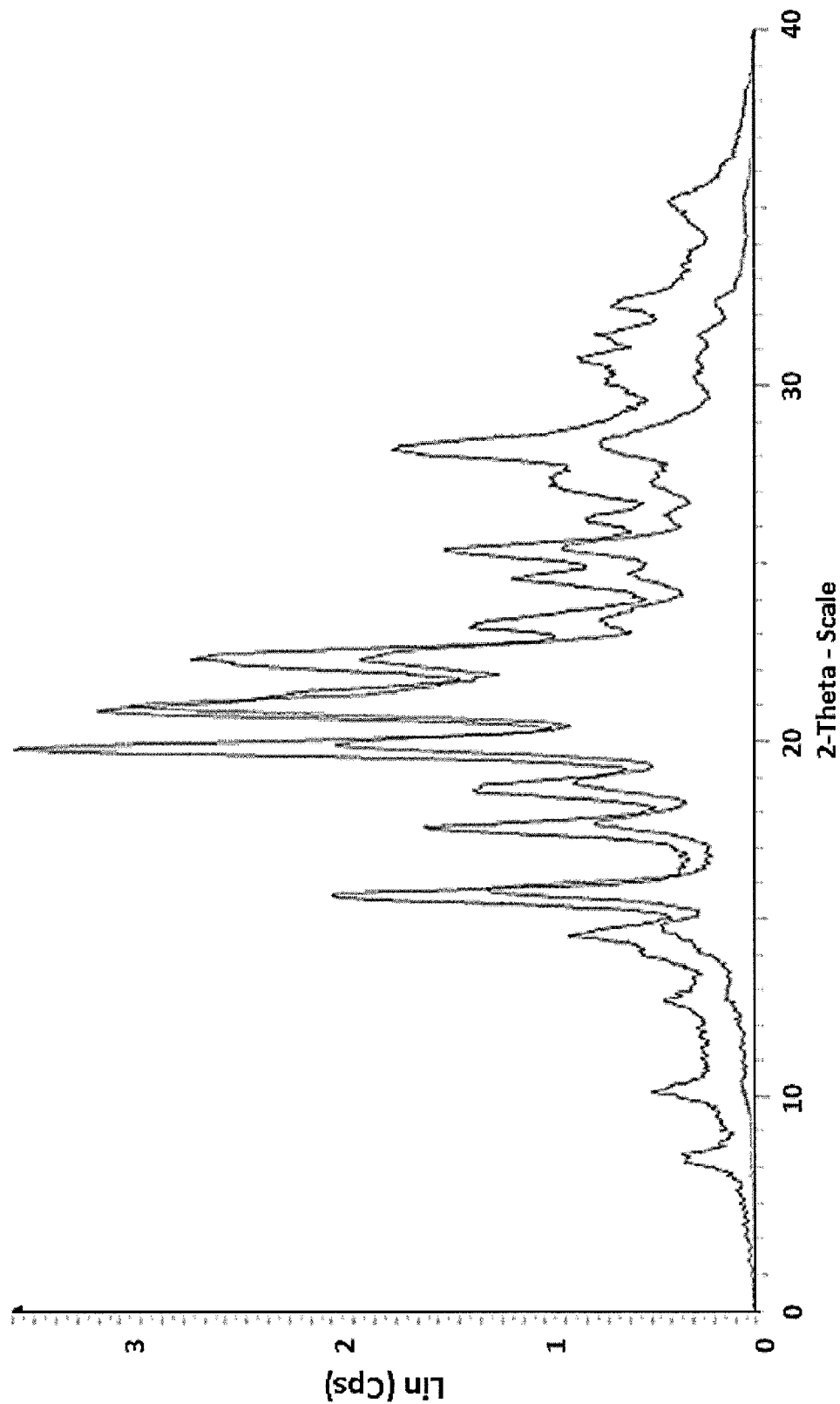
FIG. 20 shows x-ray diffractograms of the hydrochloride: primary screen sample (black trace), scaled-up sample (red trace).
Figure 21:
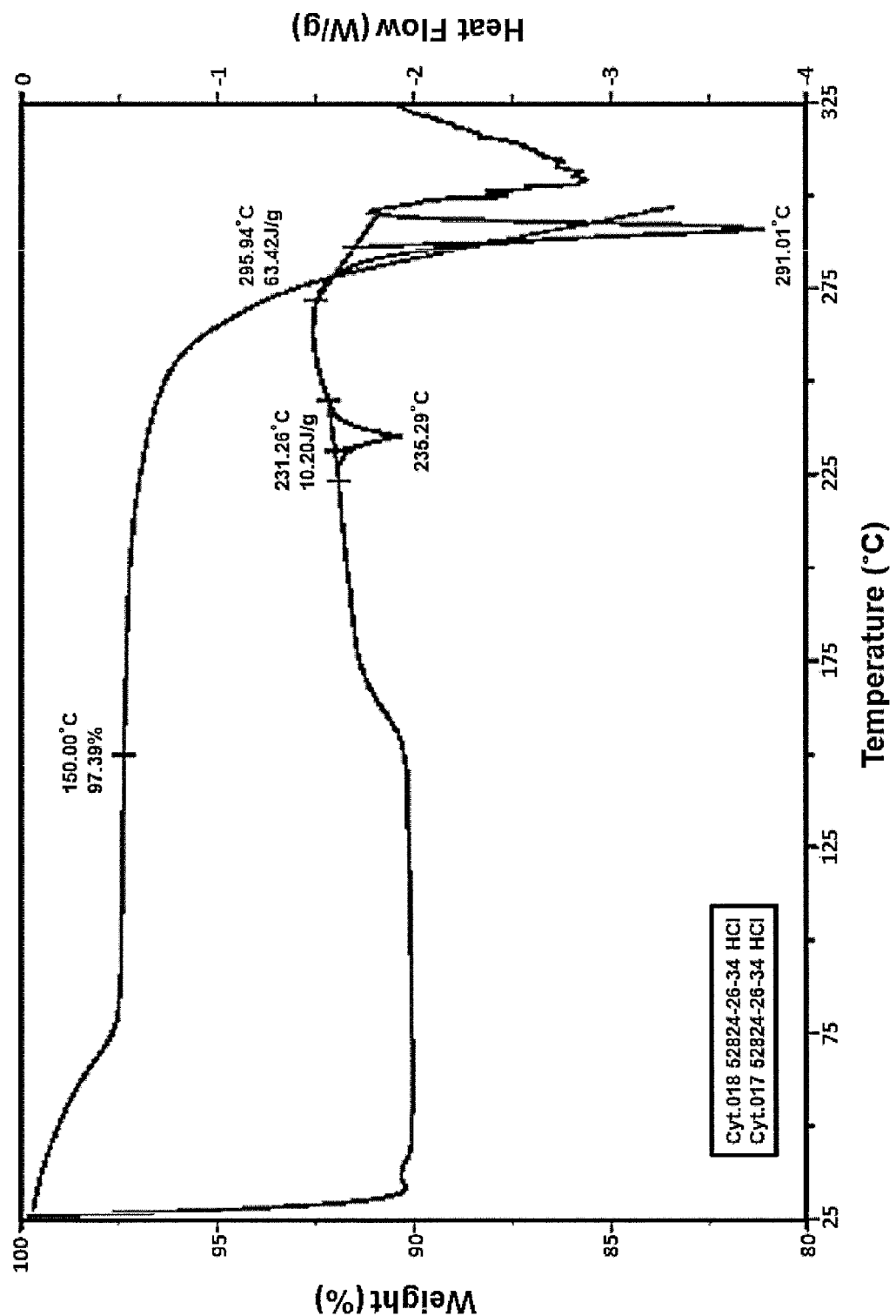
FIG. 21 shows DSC/TGA overlay of the scaled-up hydrochloride salt.
Figure 22:
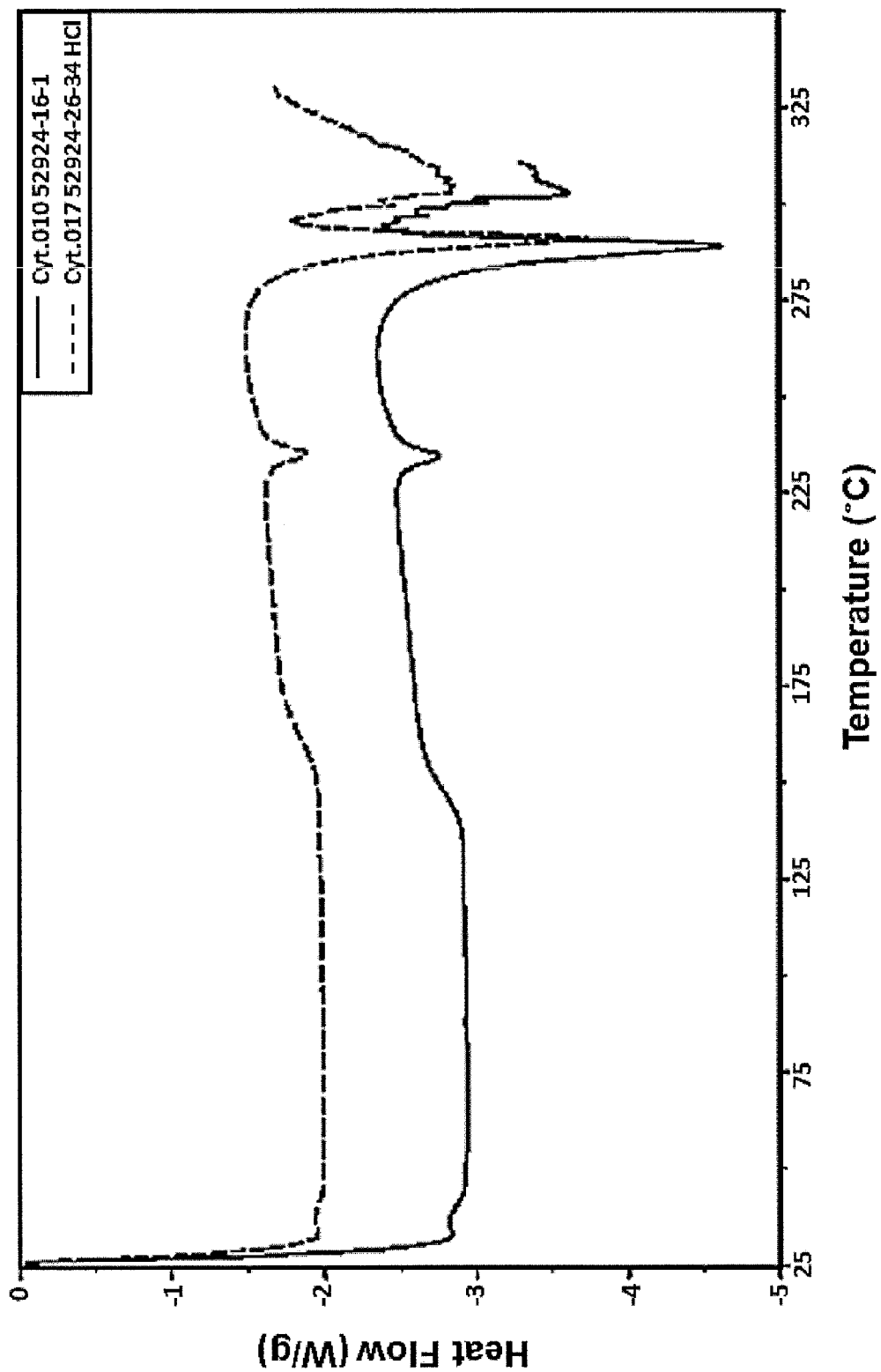
FIG. 22 shows DSC overlay of the primary screen sample (lower trace) and the scaled-up sample (upper trace) of the hydrochloride salt.

The scaled-up sample of the hydrochloride salt displayed the same XRD pattern as in the initial evaluation (see XRD plots overlay for the two samples in FIG. 20). The thermal behavior of both batches was also similar. The DSC/TGA thermograms of the scaled-up sample is in FIG. 21 and a comparison of DSC thermograms of the primary and scaled-up samples is in FIG. 22. The material exhibited a small (10.2 J/g) endotherm with an onset temperature of 231.3° C. and the main endotherm with an onset of 285.9° C. The sample had lost 2.6 wt % volatiles at 150° C.

Hot stage microscopy of the hydrochloride revealed no changes in particle morphology up to the melt, which was observed at approximately 280° C. The evolution of bubbles was evident at 108° C. and again at 230° C.

Figure 23:
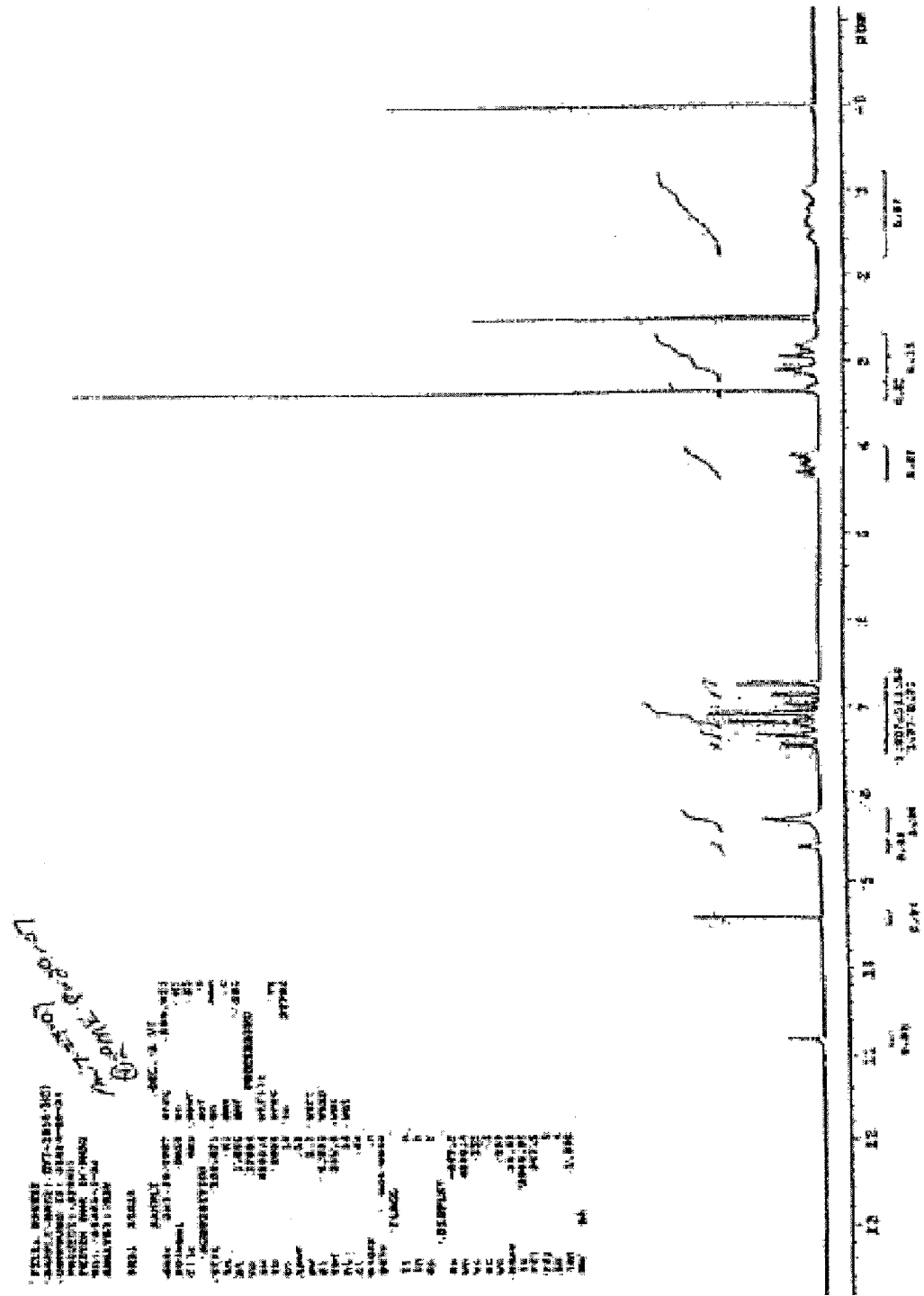
FIG. 23 shows H-NMR spectra of the scaled-up sample hydrochloride.
Figure 24:
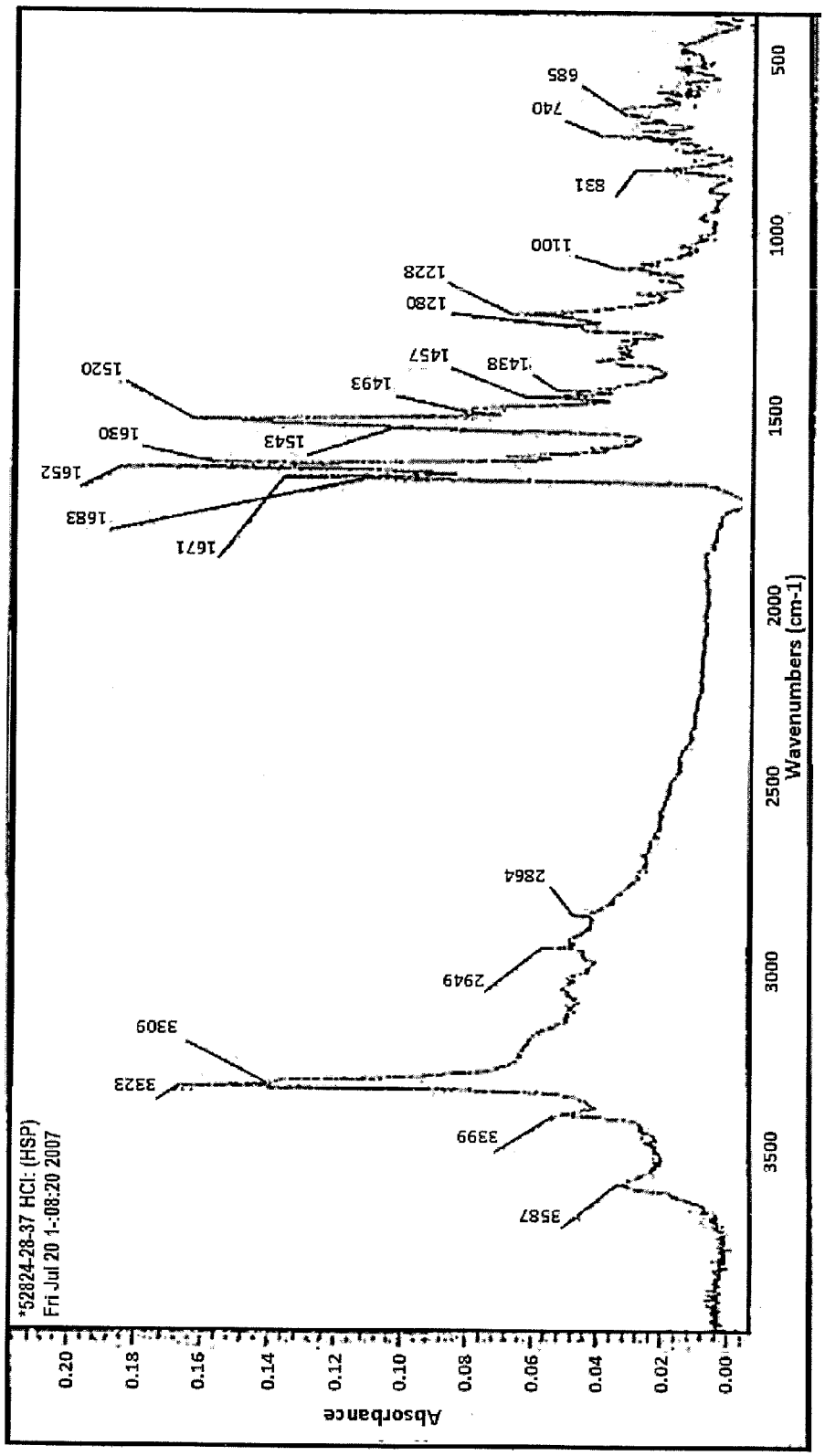
FIG. 24 shows FTIR spectrum of the scaled-up hydrochloride.

The promoton NMR spectrum (FIG. 23) suggests that the stoichiometry of the salt is approximately 1:1. The FTIR spectrum of the scaled-up hydrochloride salt is shown in FIG. 24.

IC was used to evaluate the chloride content of the scaled-up salt. The IC indicated the chloride content was 5.2 wt % (theoretical 5.5 wt %).

Figure 25:
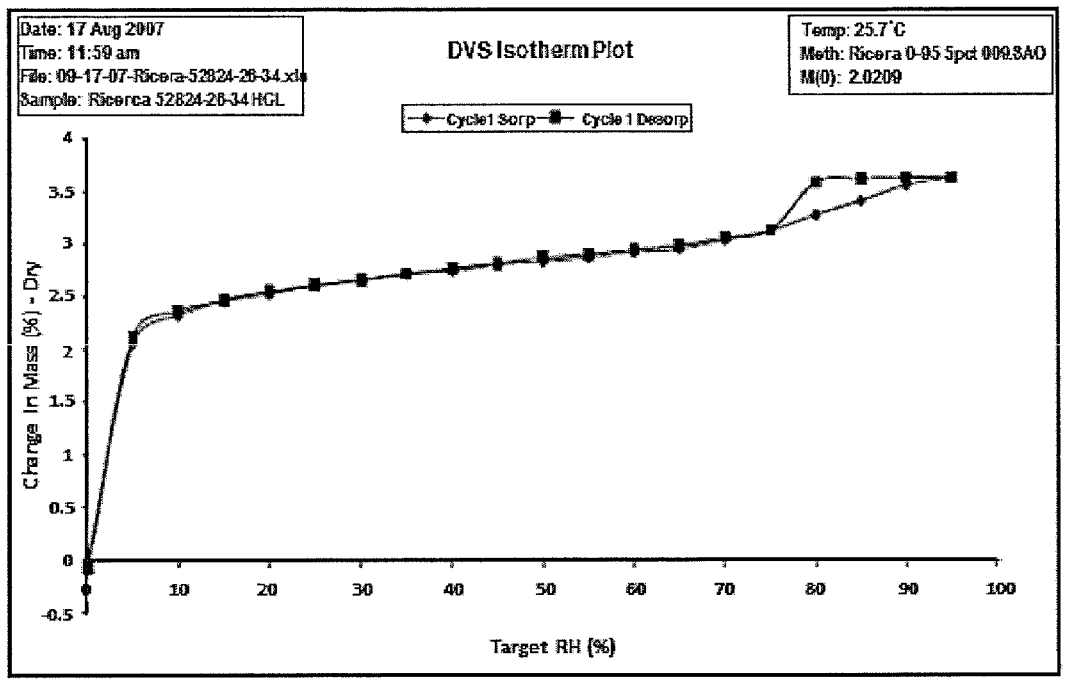
FIG. 25 shows DVS moisture isotherm of the scaled-up hydrochloride salt.
Figure 25:
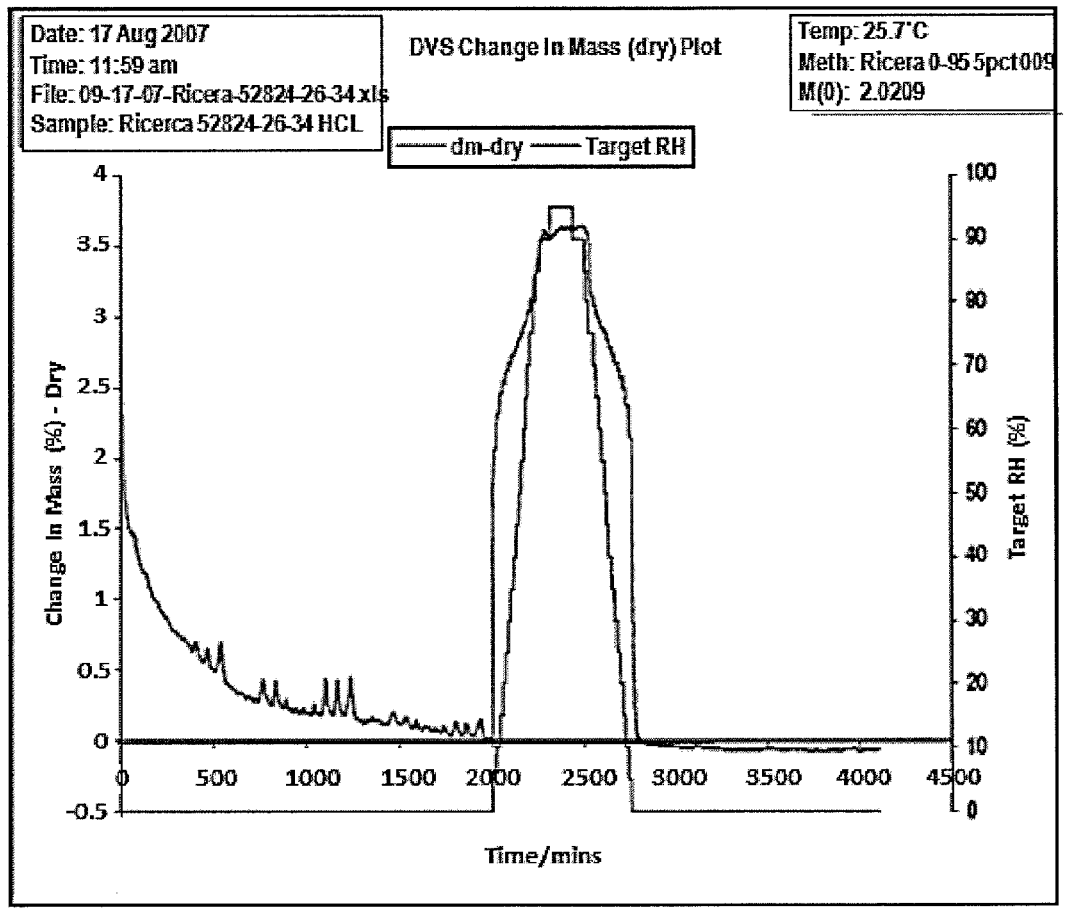

The DVS analysis suggested a reversible hydrate formation at 5% RH (FIG. 25). Given the approximately 2.5 wt % water uptake, this would imply a monohydrate forms (theoretical 2.7 wt % water).

Figure 26:
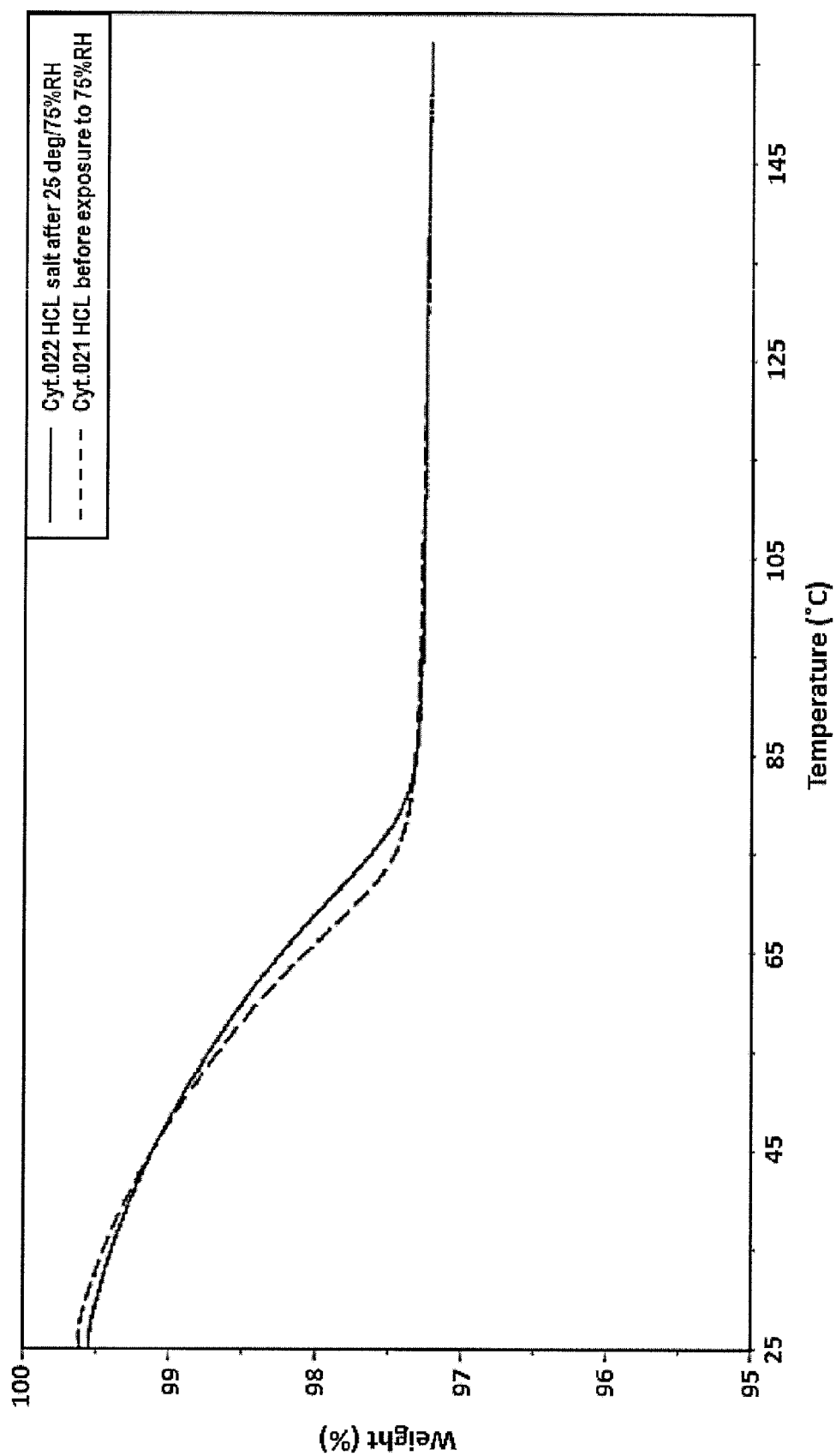
FIG. 26 shows TGA thermograms comparison of CYT-1010 HCl before and after 25° C./75% RH exposure.

A sample of HCl was stored at 25° C. and 75% RH for one week and then reweighed, no weight gain was observed. The exposed sample was analyzed by TGA to check the thermal profile after the exposure of the sample to humidity. It did not show any additional weight loss due to moisture. A comparison of TGA thermograms before and after the humidity exposure is shown in FIG. 26.

Figure 27:
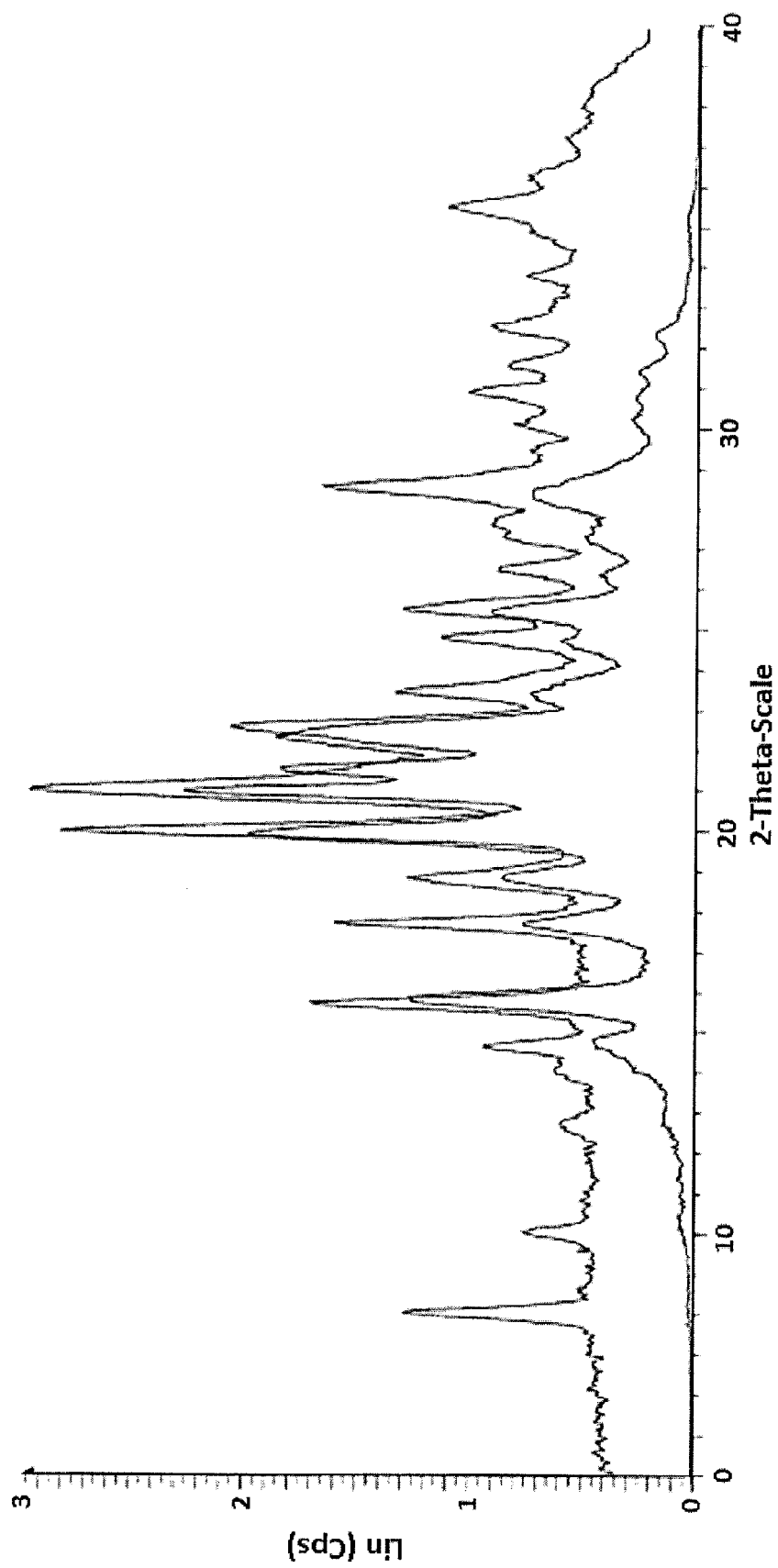
FIG. 27 shows x-ray diffractograms of CYT-1010 HCl (black) and water slurry sample (blue trace).

A slurry of the hydrochloride salt in water was carried out by stirring an excess of the HCl salt in water on a stirplate for approximately one week. Slurry was filtered and the wet cake analyzed by XRD to check for any structural changes. XRD patterns of samples before and after the slurry were essentially the same (FIG. 27), suggesting that the XRD pattern probably represents the monohydrate form of the material.

The stability data of the hydrochloride salt is described below.

The aqueous solubility results at pH 4, pH 7, and pH 10 are shown in Table 10.

Lactate

Figure 28:
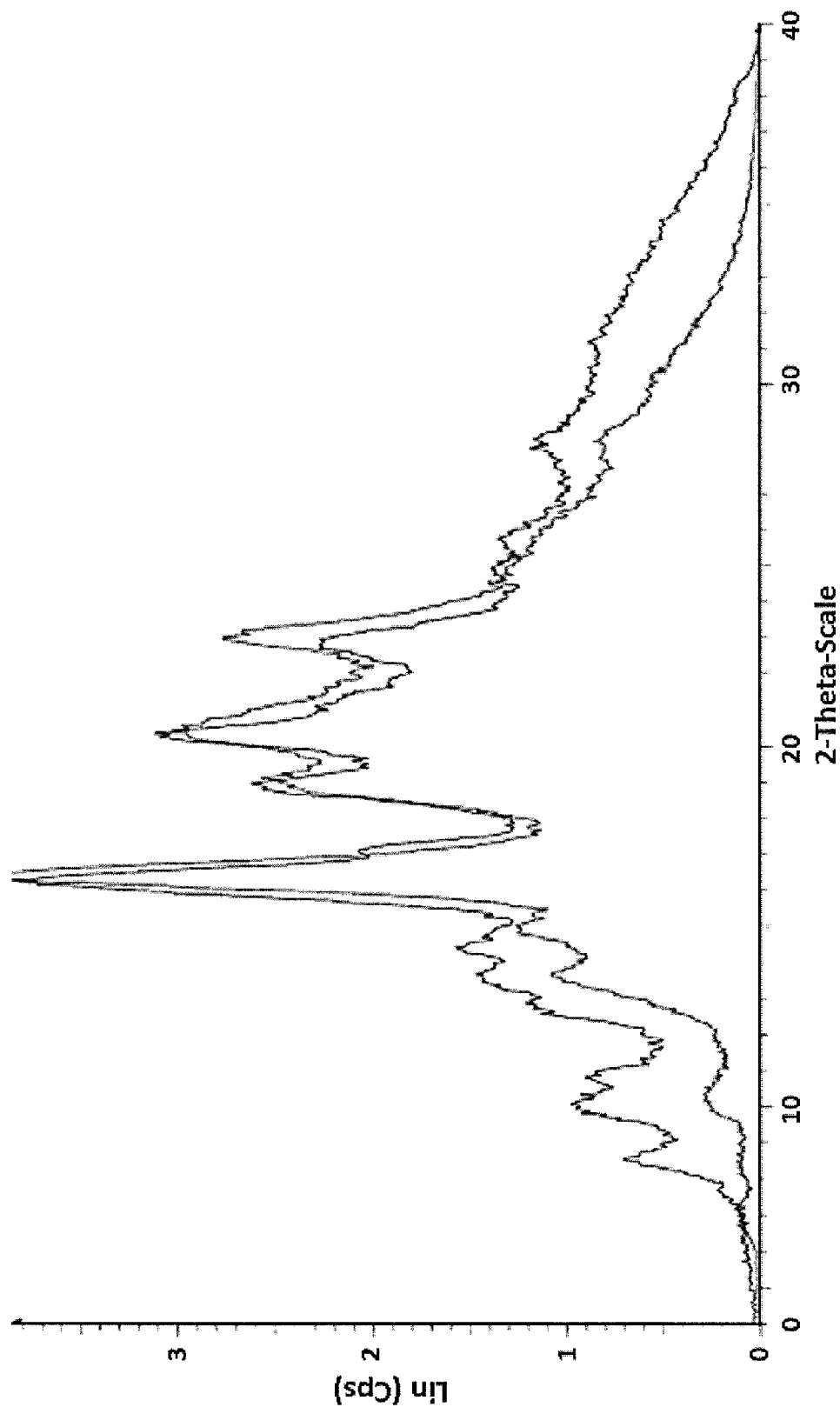
FIG. 28 shows x-ray diffractograms of the lactate: primary screen sample (black trace), scaled-up sample (red trace).
Figure 29:
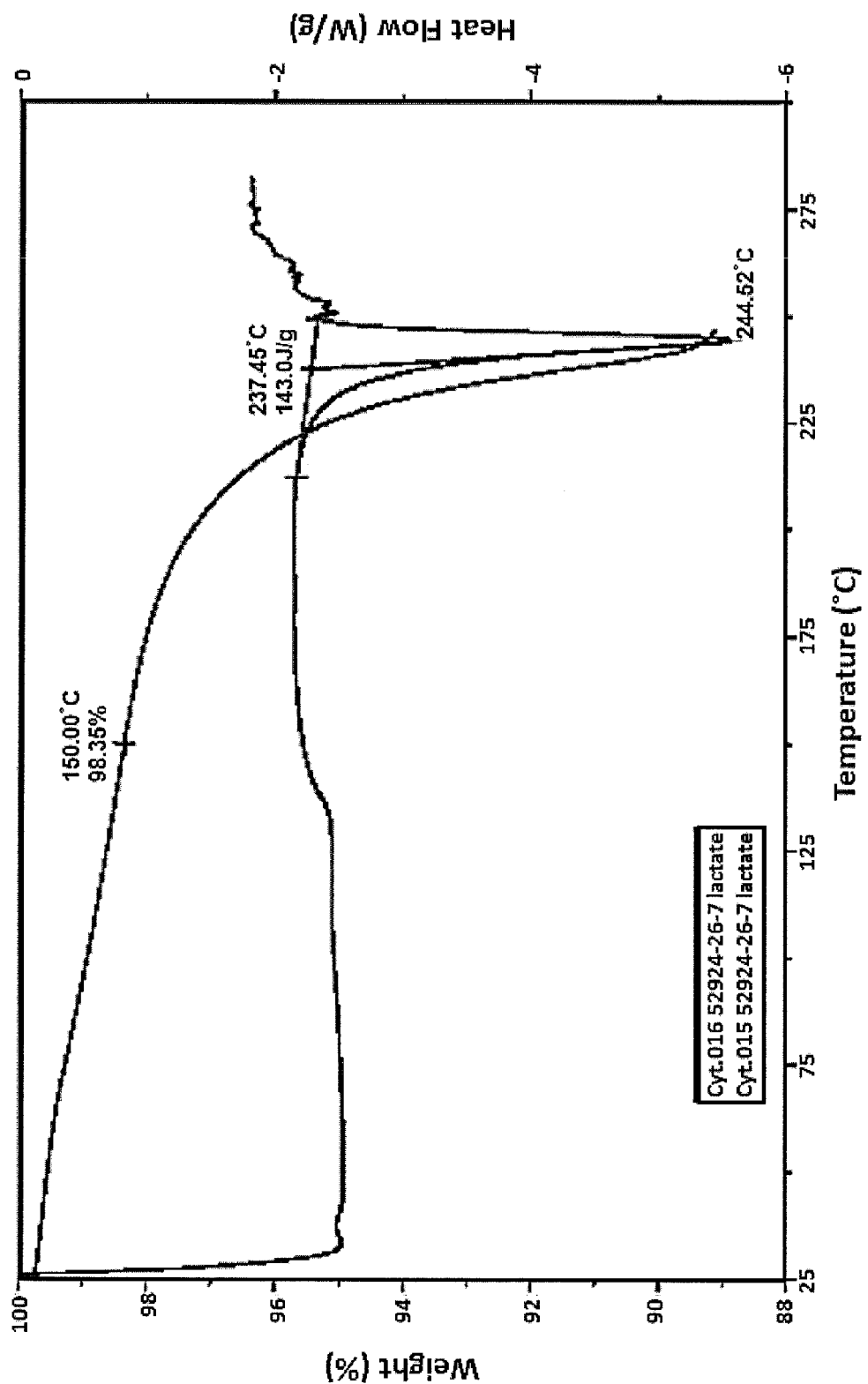
FIG. 29 shows DSC/TGA overlay of the lactate scaled-up sample.
Figure 30:
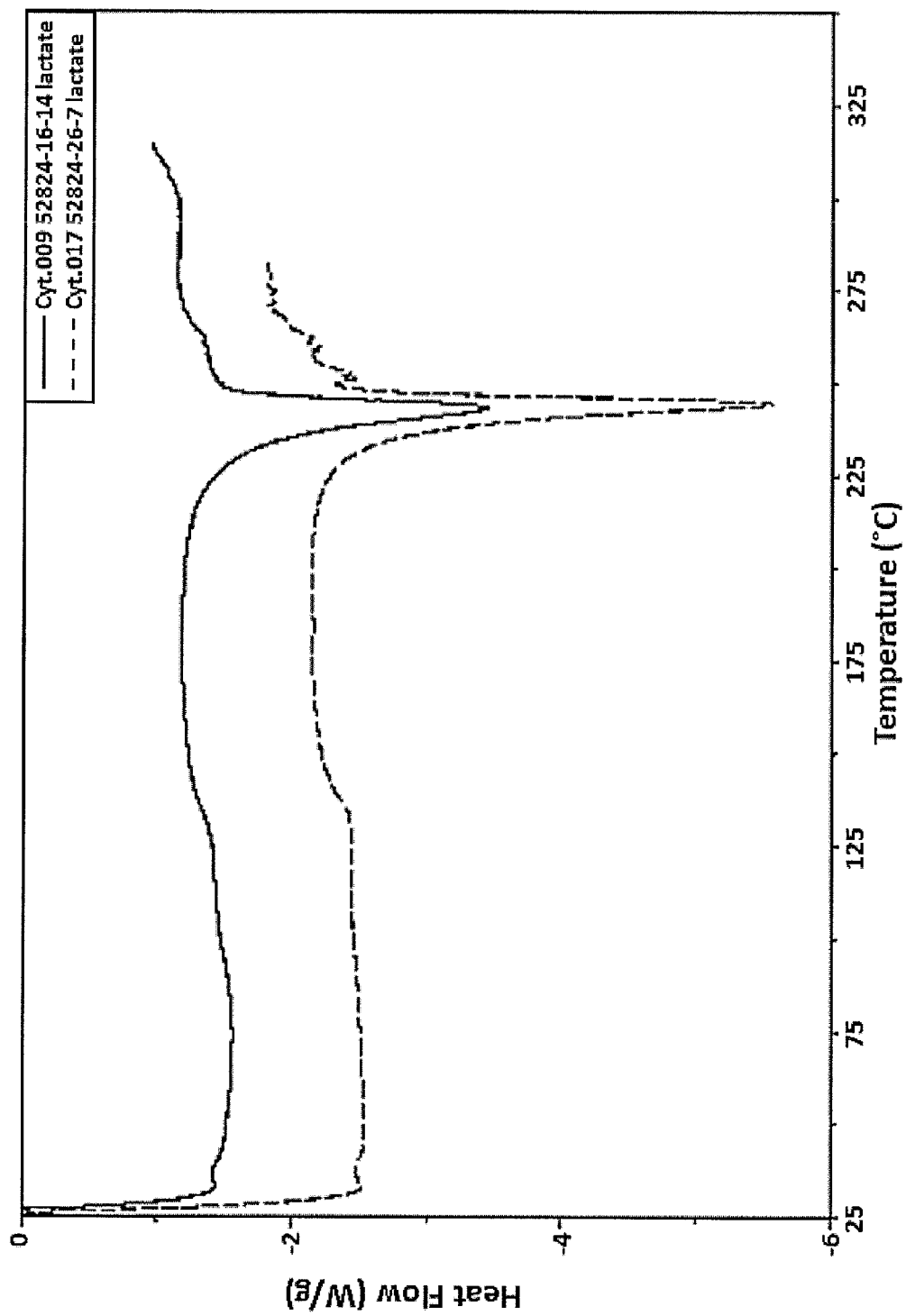
FIG. 30 shows DSC overlay of the primary screen sample (upper trace) and the scaled-up sample (lower trace) of the lactate salt.

The scaled-up sample of the lactate salt was crystalline and had the same XRD pattern as in the initial evaluation. Thermal profiles were also similar (see XRD plots overlay for the two samples in FIG. 28 and DSC/TGA data for the scaled-up sample in FIG. 29). DSC thermogram of the scaled-up sample had a melting endotherm with an onset temperature of approximately 237.5° C. and an enthalpy value of 143 J/g. The total volatiles by TGA were 1.7 wt % at 150° C. A comparison of DSC thermograms of the primary and scaled-up samples is shown in FIG. 30.

The stoichiometry of the monosalt was evaluated using ion chromatography (IC). The sample contained approximately 9.8 wt % lactic acid which is lower than the theoretical expected result (12.6 wt %). To determine why it was lower, a lactic acid solution used for the preparation of salts (Fisher, assay 88.3%) was analyzed by IC and assay value was determined to be only 76.8 wt % as opposed to the label claim of 88.3 wt %.

Figure 31:
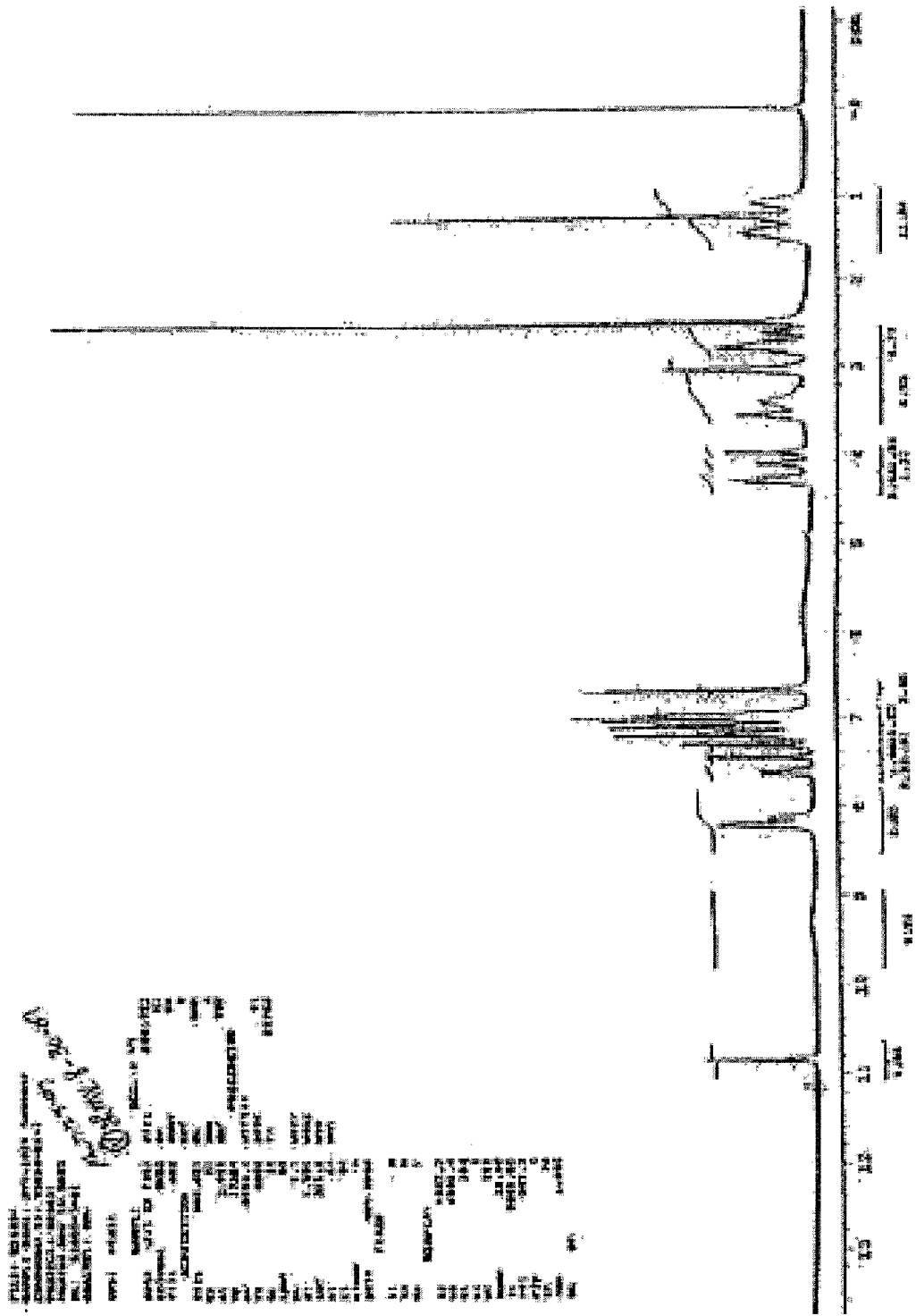
FIG. 31 shows H-NMR spectra of the scaled-up lactate.
Figure 32:
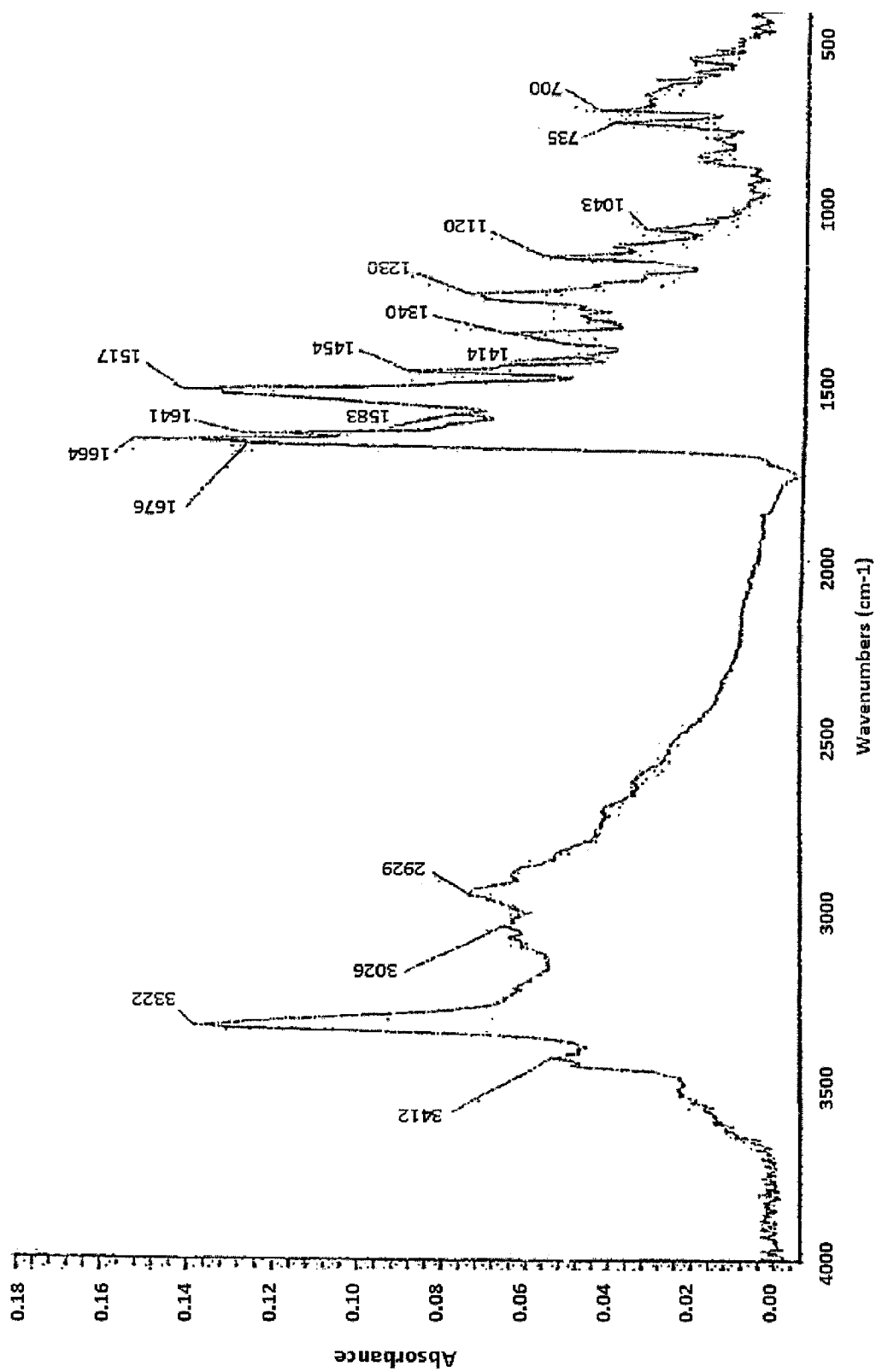
FIG. 32 shows FTIR spectrum the scaled-up lactate.

MNR and FTIR spectra of the scaled-up lactate are in FIG. 31, and FIG. 32, respectively. The methine peak at ~4.0 ppm integrated to 1.23. This would indicate that the mole ratio is approximately 1 to 1 (a monosalt).

Figure 33:
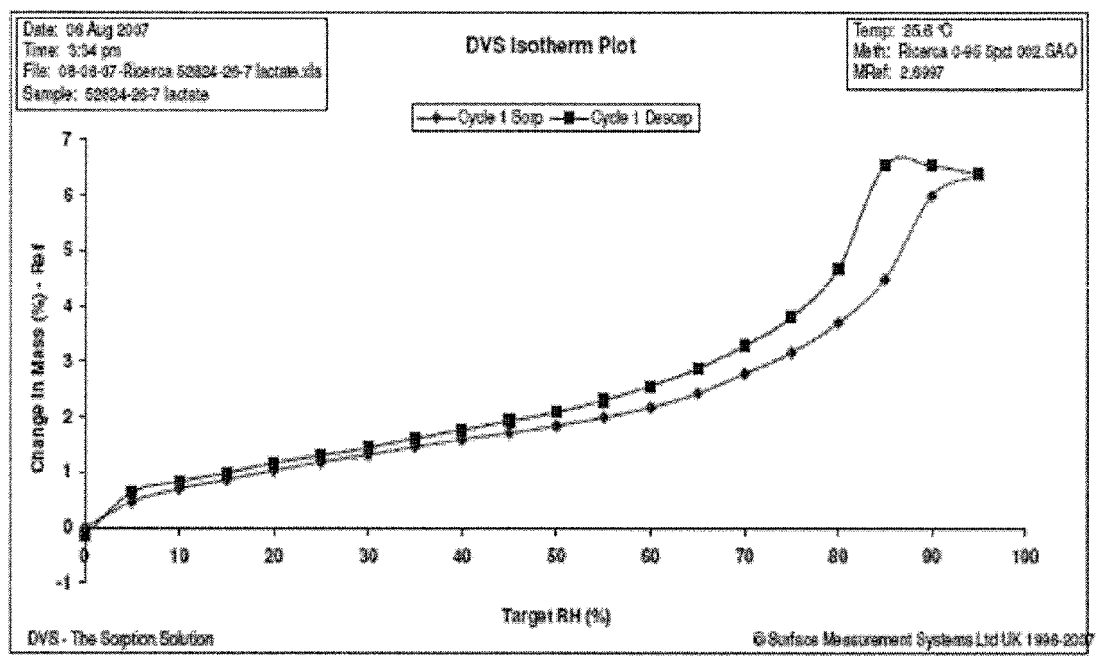
FIG. 33 shows DVS moisture isotherm of the scaled-up lactate salt.
Figure 33:
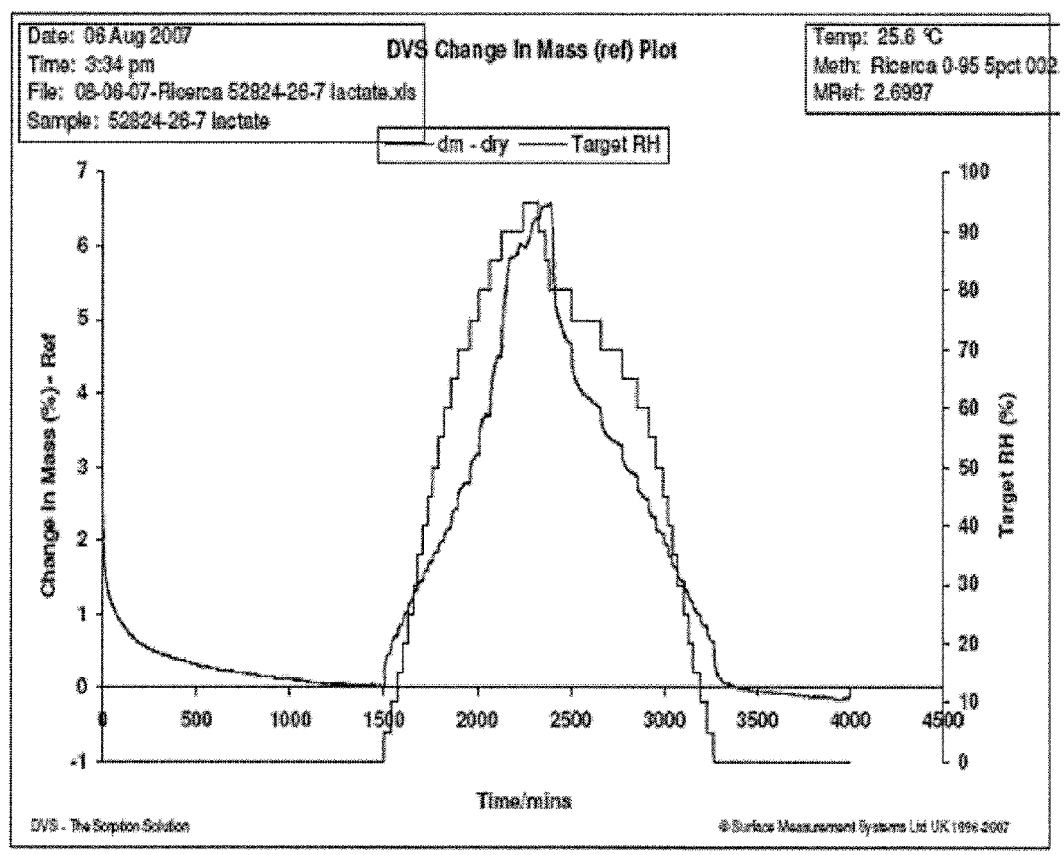

DVS analysis indicated non-stoichiometric water update of 1-3 wt % in 0-70% RH range and up to 6 wt % by 90% RH (FIG. 33). Given the smooth shape of the curve it was not possible to deduce whether this uptake represents hydrate formation or not.

The aqueous solubility results at pH 4, pH 7, and pH 10 are shown in Table 10.

Maleate

Figure 34:
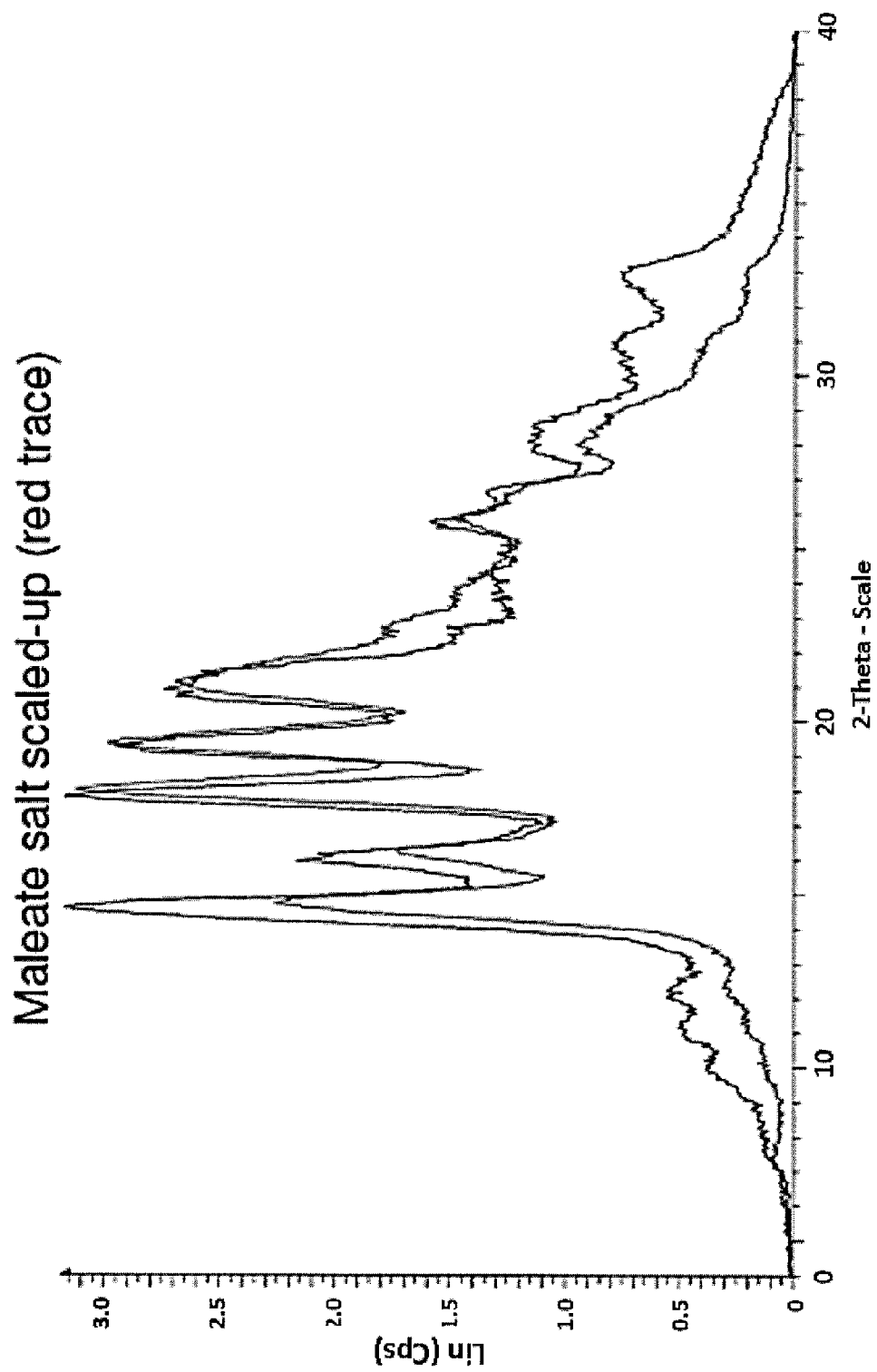
FIG. 34 shows x-ray diffractograms of the maleate: primary screen sample (black trace), scaled-up sample (red trace)

The scaled-up sample of the maleate salt was crystalline. XRD patterns of the primary screen and scale-up malate salts were very similar as can be seen in FIG. 34.

Figure 35:
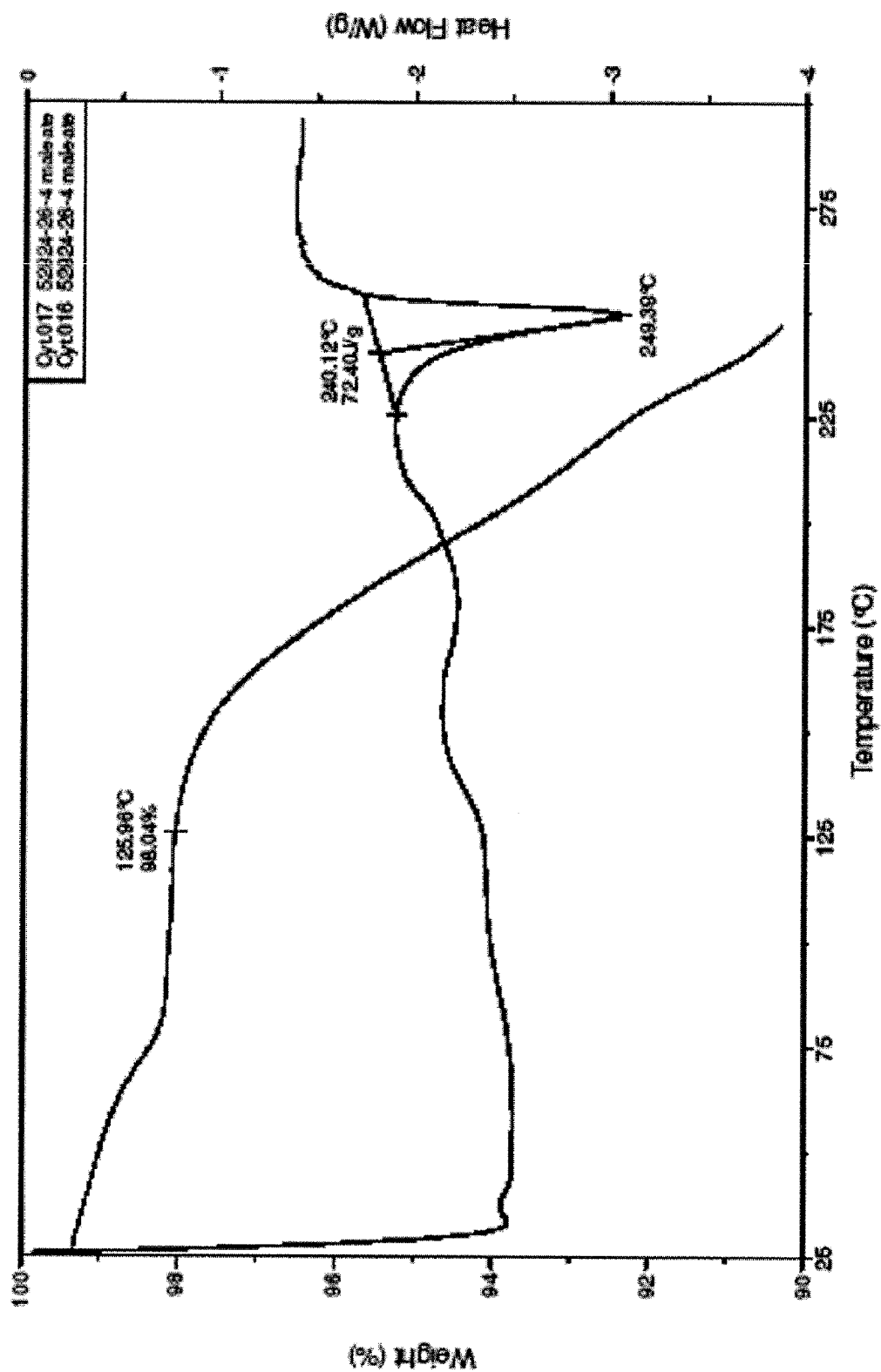
FIG. 35 shows DSC/TGA overlay of the maleate scaled-up sample.
Figure 36:
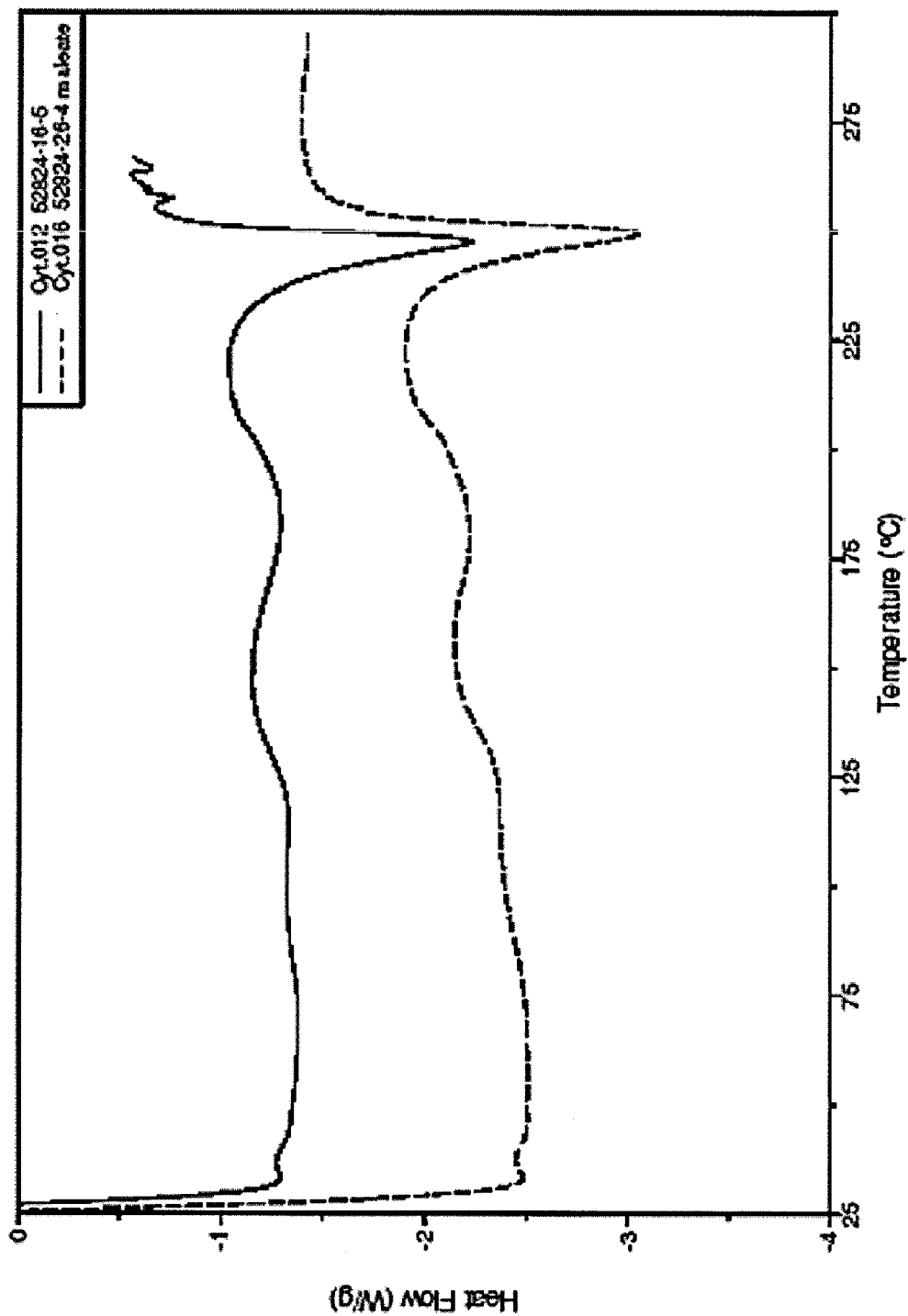
FIG. 36 shows DSC overlay of the primary screen sample (upper trace) and the scaled-up sample (lower trace) of the maleate salt.

The DSC thermogram exhibited the same thermal behavior as in the initial evaluation. The weight loss observed at 125° C. was ~2 wt %. After additional drying, the volatile content was 1.5 wt %. The DSC/TGA overlay plot of the scaled-up maleate is shown in FIG. 35. A comparison of DSC thermograms of the primary and scaled-up samples is shown in FIG. 36. The thermograms show good repeatability.

The stoichiometry of the monosalt was evaluated using ion chromatography (IC). The sample contained approximately 14.0 wt % maleic acid which is close to the theoretical value of 15.7 wt %.

Figure 37:
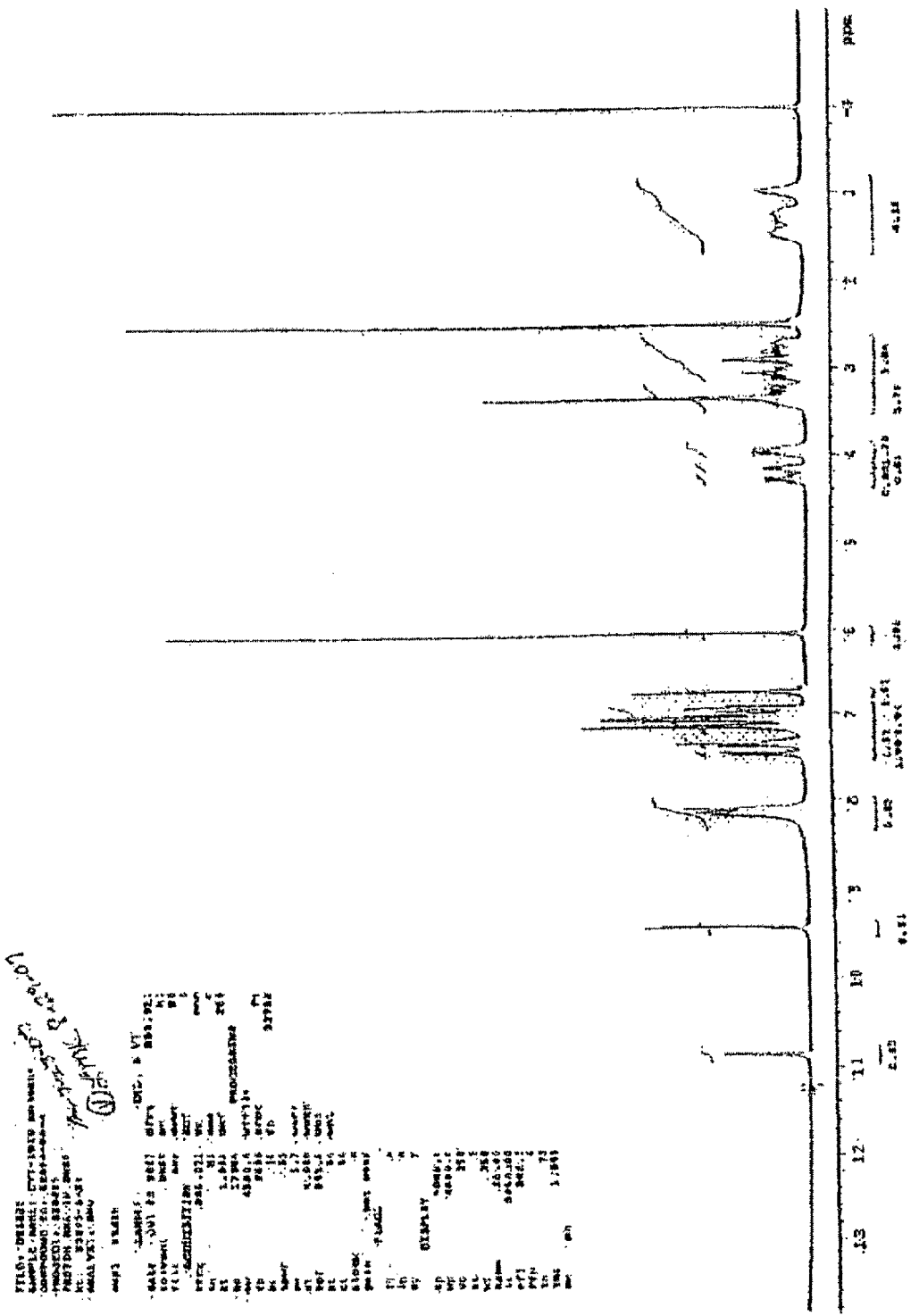
FIG. 37 shows H-NMR spectrum of the scaled-up sample of the maleate salt.
Figure 38:
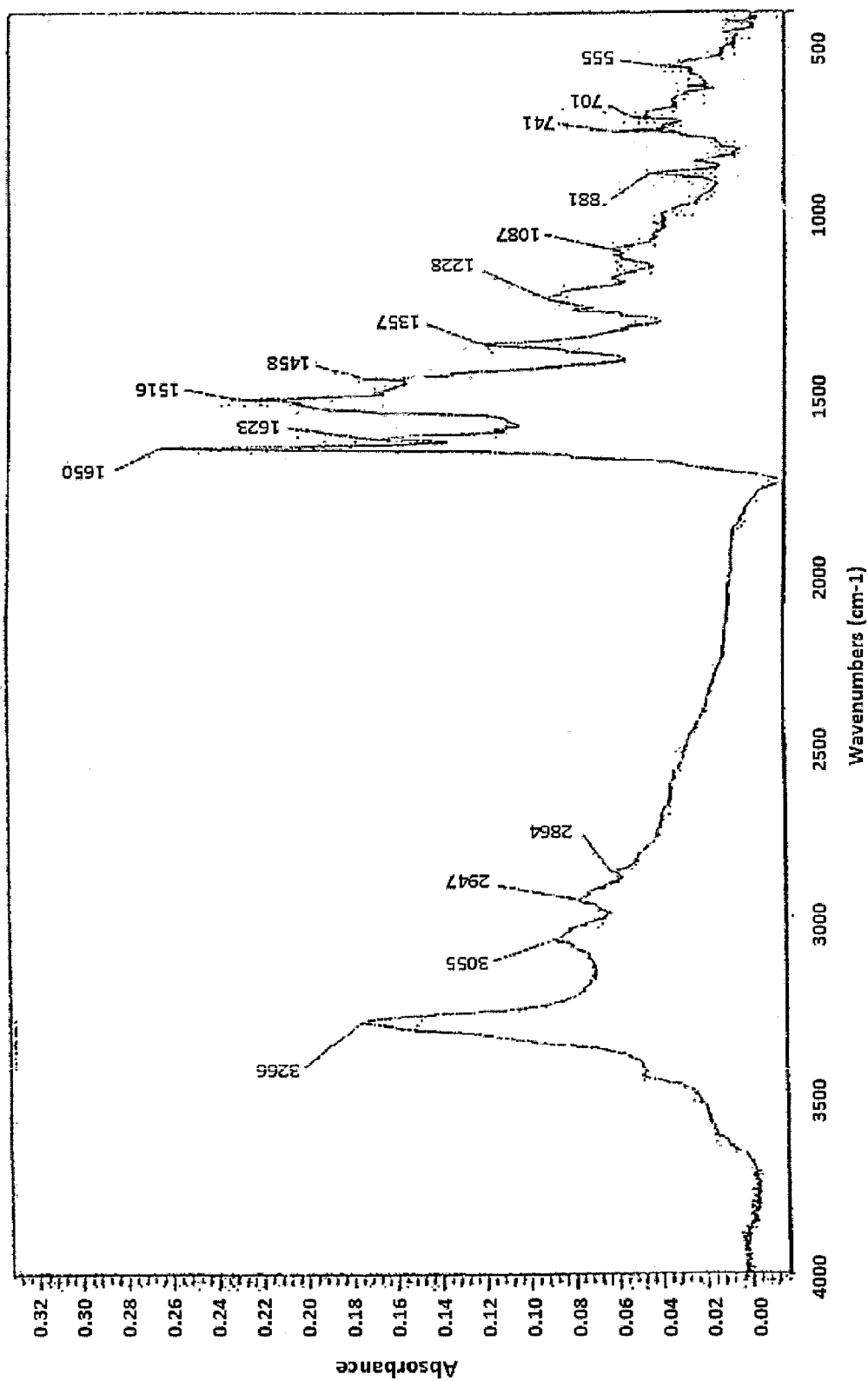
FIG. 38 shows spectrum of the scaled-up sample of the maleate salt.

The H-NMR spectrum of the maleate is shown in FIG. 37. The FTIR spectrum of the scaled-up maleate salt is in FIG. 38.

Figure 39:
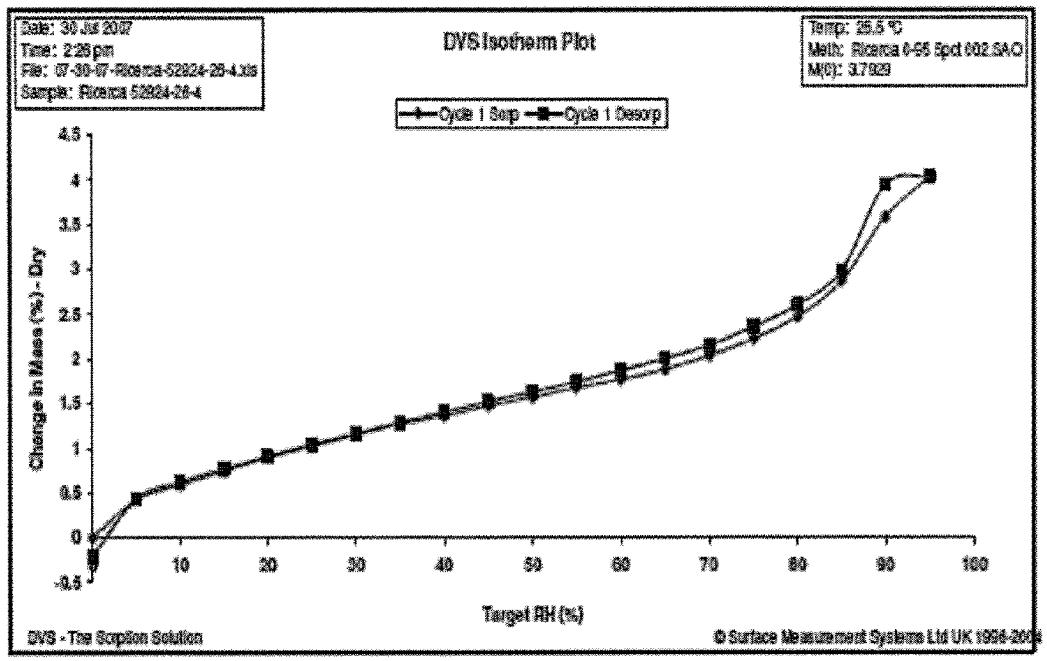
FIG. 39 shows DVS moisture isotherm of the scaled-up maleate salt.
Figure 39:
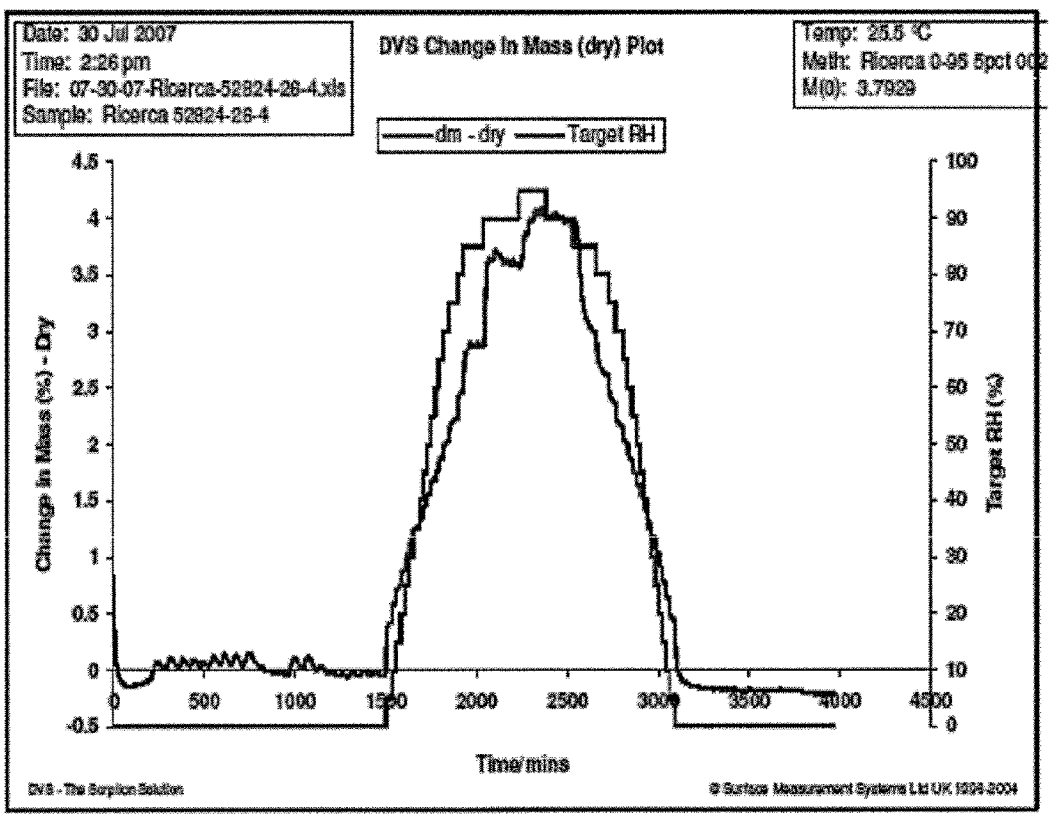

DVS analysis (FIG. 39) indicated non-stoichiometric water uptake of approximately 3.5 wt % over the 0-95% RH range. Whether a hydrate formed or not could not really be deduced from this data.

The aqueous solubility results at pH 4, pH 7, and pH 10 are shown in Table 10.

Example 5

Stability of Scaled-Up Salts

The scaled-up aspartate, hydrochloride, lactate, and maleate salts together with the free base were analyzed in duplicate by total area normalization (TAN) to determine their impurity profiles. The salts were stressed in solid state using heat, light, and a pure oxygen atmosphere to determine if the salt forms exhibited different chemical stability characteristics. The salts were also stressed in solution using heat.

Samples were prepared at a free base concentration of 0.3 mg/mL. The diluent for all sample preparations was 90:10 acetronitrile:water with 0.1% TFA. All solutions were sonicated for at least five minutes prior to analysis. Analysis was done over four days. The impurity profile of the free base, as shown in the table below, was consistent over this time.

| CYT-1010 Free Base Impurity Profile[1] | | | | | | | |
|---|---|---|---|---|---|---|---|
| Form | 0.89 | 0.92 | 0.95 | 1.02 | 1.03 | 1.14 | 1.18 |
| Free Base Day 1 | 0.09 | 0.05 | ND | 0.53 | 0.16 | ND | ND |
| Free Base Day 2 | 0.12 | 0.06 | ND | 0.51 | 0.13 | ND | ND |
| Free Base Day 3 | 0.13 | 0.07 | ND | 0.53 | 0.18 | ND | ND |

[1]Impurity profile an average of the first three injections of the WI Free Base Injections.

Solution Stability

The solution stability characteristics were evaluated by collecting HPLC data on solutions stored in sealed vials for two weeks at approximately 25 and 40° C. The storage solution consisted of 90:10 acetronitrile:water with 0.1% TFA which is the diluent for the HPLC assay. Table 6 summarizes the results of the HPLC analyses of these experiments.

TABLE 6

Solution Stability Results

| Salt | Time Zero (area %) | 2 weeks at 25° C. (area %) | 2 weeks at 40° C. (area %) |
|---|---|---|---|
| Free Base | 99.2 | 98.6 | 98.7 |
| L-aspartate | 99.1 | 98.6 | 98.6 |
| Maleate | 96.2 | 96.7 | 97.2 |
| Lactate | 99.2 | 98.5 | 98.5 |
| Hydrochloride | 99.1 | 98.5 | 98.5 |

The solution stability data for the free base and three of four salts, L-aspartate, lactate, and hydrochloride, showed a decrease between 0.6 and 0.7 area % at 25° C. These compounds exhibited almost the same decrease in area percent at 40° C. This behavior suggests that the changes for these compounds were due to exposure to the diluent and not the heat. On the other hand, the maleate salt showed a 0.5 area % increase at 25° C. and an additional 0.5 area % increase at 40° C.

Solid State Stability

The solid state stability characteristics were evaluated by collecting HPLC data on salt samples stored in sealed vials at 25 and 60° C. for two weeks. Results of the HPLC analyses are summarized in the Table 7.

TABLE 7

Solid State Stability Results

| Salt | Time Zero (area %) | 2 weeks at 25° C. (area %) | 2 weeks at 60° C. (area %) |
|---|---|---|---|
| Free Base | 99.2 | 98.8 | 98.7 |
| L-aspartate | 99.1 | 99.1 | 98.9 |
| Maleate | 96.2 | 96.2 | 89.1 |
| Lactate | 99.2 | 99.0 | 98.5 |
| Hydrochloride | 99.1 | 98.9 | 98.9 |

The thermal stability data for the L-asparate and maleate salts did not exhibit significant changes in assay values upon exposure at 25° C. The lactate and hydrochloride salts only decreased slightly, a decrease of 0.2 area %, while the free base decreased 0.4 area % at 25° C. The hydrochloride salt did not exhibit further decrease in area % at 60° C. The free base decreased slightly in area % and the lactate salt decreased 0.5 area % at 60° C. as compared to 25° C. data. The maleate salt showed significant decrease, 7.1 area %.

Photostability

Samples of the four salt candidates were exposed to ICH compliant option 2 UV sources to examine their stability with respect to light at approximately 25° C. Dark controls were also analyzed for comparison. Table 8 summarizes the results of the HPLC data on the photostability samples.

TABLE 8

Photostability Stress Results

| Salt | Time Zero (area %) | 2 weeks Dark Control (area %) | 2 weeks UV Exposed (area %) |
|---|---|---|---|
| Free Base | 99.2 | 99.0 | 98.9 |
| L-aspartate | 99.1 | 99.1 | 98.8 |
| Maleate | 96.2 | 96.3 | 96.3 |
| Lactate | 99.2 | 99.0 | 98.6 |
| Hydrochloride | 99.1 | 99.1 | 99.0 |

The photostability data for the two of the four salts did not exhibit significant changes in assay values upon exposure. The lactate salt showed the greatest change in area %, a decrease of 0.6 area % from time zero to exposed, while the free base and L-asparate salt both decreased 0.3 area % from time zero to exposed.

Oxidation Stability

Samples of the four salts were exposed to a pure oxygen atmosphere to examine their stability with respect to oxidation at 25° C. Table 9 summarizes the results of the HPLC data on the photostability.

TABLE 9

Oxidation Stability Results

| Salt | Time Zero (area %) | 2 weeks Oxidation (area %) |
|---|---|---|
| Free Base | 99.2 | 97.7 |
| L-aspartate | 99.1 | 98.8 |
| Maleate | 96.2 | 95.8 |
| Lactate | 99.2 | 98.8 |
| Hydrochloride | 99.1 | 98.7 |

The oxidative stability data for the free base had the greatest change with 1.5 area % decrease. The four salts showed a decrease between 0.3 and 0.4 area %.

Example 6

Solubility of Scaled-Up Salts

Solubility measurements were made at ambient temperature in pH 4 buffer (potassium biphthalate buffer 0.05 molar), pH 7 buffer (potassium phosphate mono basic-sodium hydroxide buffer 0.05 molar) and pH 10 buffer (potassium carbonate-potassium hydroxide buffer 0.05 molar). Two approaches were tried. A visual technique and HPLC analysis were used to determine the solubilities.

By visual technique, solubilities of all four salts and the free base in pH 4, 7 and 10 buffers were less than 0.05 mg/ml.

The results of the solubility determinations by HPLC are shown in Table 10. HPLC data were collected on solutions stored in sealed vials for approximately one week at 25° C. at pH 4, pH 7, and pH 10. Portions of these solutions were filtered with a Teflon 0.45 micro filter prior to HPLC analysis. The results were calibrated with a six point calibration curve ranging from 0.12 to 0.003 mg/ml. The same HPLC conditions were used as listed previously except the injection volume was increased to 10 µL.

TABLE 10

Solubility of Salts in Aqueous Buffers

| | pH Results - mg/ml | | |
|---|---|---|---|
| Salt | pH 4 | pH 7 | pH 10 |
| Free Base | ND | <0.003 | 0.006 |
| L-aspartate | ND | <0.003 | 0.007 |
| Maleate | ND | 0.003 | 0.007 |
| Lactate | ND | <0.003 | 0.007 |
| Hydrochloride | ND | <0.003 | 0.006 |

The solubility behavior was similar for all five compounds in that the solubility increased with increasing pH.

Example 7

HPLC Impurity Profiles

Time Zero. Some observations were made concerning the HPLC impurity profile of the free base and salt samples. First, impurities at 0.89, 0.92, 1.02, and 1.03 RRT (relative retention time) are detected in the time zero sample preparations of the free base and all four salts. The largest of these four impurities is the 1.02 RRT impurity which is between 0.4 and 0.5 area % in all five compounds. The maleate salt also has a very large impurity peak at time zero (2.7 area %) at 1.14 RRT. Thus the maleate salt has a relatively low area % purity of 96 area %. Time zero impurity profile data is shown in Table 11.

TABLE 11

| | Impurity Profile at Time Zero Impurity by RRT | | | | | | | |
|---|---|---|---|---|---|---|---|---|
| Salt | 0.87 | 0.89 | 0.92 | 0.95 | 1.02 | 1.03 | 1.14 | 1.18 |
| Free Base | ND | 0.09 | 0.05 | ND | 0.53 | 0.16 | ND | ND |
| L-aspartate | ND | 0.05 | 0.09 | 0.07 | 0.46 | 0.10 | 0.12 | <0.03 |
| Maleate | ND | 0.11 | 0.13 | 0.16 | 0.40 | 0.18 | 2.67 | 0.11 |
| Lactate | ND | 0.04 | 0.08 | 0.10 | 0.49 | 0.13 | ND | <0.03 |
| Hydrochloride | <0.03 | 0.04 | 0.08 | 0.19 | 0.49 | 0.09 | ND | ND |

Example 8

Stability

Solution Stability

The solution stability data for the free base and three out of four salts, L-asparate, lactate, and hydrochloride, showed a decrease between 0.6 and 0.7 area % at 25° C. and 60° C. In all the stability solutions, including the maleate, a new impurity peak appears at 0.21 RRT that is 0.5 to 0.6 area % in size. This peak is unique to the solution stability samples. Another difference is seen with the maleate salt. The peak at 1.14 RRT decreases from a time zero value of 2.7 area % to 1.7 area % at 25° C. in solution and to 1.1 area % at 40° C. in solution. This is the same impurity peak that increases to 10 area % in the 60° C. solid state maleate sample. The solution stability impurity profile data is shown in Tables 12 and 13.

TABLE 12

| | Solution Stability 25° C. Impurity Profile Impurity by RRT | | | | | | | | |
|---|---|---|---|---|---|---|---|---|---|
| Salt | 0.21 | 0.89 | 0.92 | 0.95 | 0.98 | 1.02 | 1.03 | 1.14 | 1.18 |
| Free Base | 0.50 | 0.06 | 0.04 | 0.06 | ND | 0.53 | 0.18 | ND | ND |
| L-aspartate | 0.52 | ND | 0.08 | 0.12 | ND | 0.48 | 0.16 | 0.07 | ND |
| Maleate | 0.62 | 0.04 | 0.09 | 0.18 | ND | 0.42 | 0.16 | 1.71 | 0.07 |
| Lactate | 0.59 | 0.05 | 0.11 | 0.14 | ND | 0.49 | 0.15 | ND | ND |
| Hydrochloride | 0.59 | ND | 0.04 | 0.21 | | 0.50 | 0.14 | ND | ND |

TABLE 13

| | Solution Stability 40° C. Impurity Profile Impurity by RRT | | | | | | | | | | |
|---|---|---|---|---|---|---|---|---|---|---|---|
| Salt | 0.21 | 0.89 | 0.92 | 0.95 | 0.98 | 1.02 | 1.03 | 1.14 | 1.18 | 1.32 | 2.39 |
| Free Base | 0.50 | 0.04 | ND | 0.03 | ND | 0.51 | 0.18 | ND | ND | ND | ND |
| L-aspartate | 0.58 | <0.03 | 0.07 | 0.13 | <0.03 | 0.47 | 0.15 | ND | ND | ND | ND |
| Maleate | 0.57 | 0.06 | 0.07 | 0.27 | <0.03 | 0.43 | 0.15 | 1.14 | 0.05 | ND | 0.03 |
| Lactate | 0.62 | 0.04 | 0.04 | 0.14 | <0.03 | 0.50 | 0.16 | ND | ND | <0.03 | <0.03 |
| Hydrochloride | 0.57 | ND | ND | 0.23 | 0.03 | 0.51 | 0.15 | ND | ND | ND | 0.03 |

Solid State Stability

For the solid state stability samples, the free base at 25° C. and the maleate at 60° C. showed the greatest change in the impurity profile as shown in the tables below. For the free base at 25° C., the 0.89 and 0.92 RRT impurities showed the largest increase as compared to time zero data. For the maleate salt at 60° C., the 1.14 RRT peak increase from 2.7 to 10 area % and while the impurity at 1.02 RRT decreased from 0.5 area % to a nondetectable level.

Photostability

For the photostability samples, the lactate salt showed the greatest change in the impurity profile. In the dark control, the 0.89 and 0.92 RRT impurities increased as compared to time zero data while in the photoexposed, the 0.92 and 0.95 RRT impurities increased significantly.

Oxidative Stability

For the oxidation samples, the free base showed the greatest change in the impurity profile as shown in Table 14. The 0.89 and 0.92 RRT impurities showed the largest increase as compared to time zero data. These two impurities increased for all of the salts as well.

TABLE 14

Oxiation Impurity Profile
Impurity by RRT

| Salt | 0.87 | 0.89 | 0.92 | 0.95 | 0.98 | 1.02 | 1.03 | 1.14 | 1.18 |
|---|---|---|---|---|---|---|---|---|---|
| Free Base[1] | 0.04 | 0.30 | 0.20 | 0.04 | ND | 0.53 | 0.20 | ND | ND |
| L-aspartate | ND | 0.12 | 0.14 | 0.09 | ND | 0.48 | 0.16 | 0.09 | <0.03 |
| Maleate | 0.04 | 0.36 | 0.27 | 0.21 | ND | 0.38 | 0.15 | 2.70 | 0.12 |
| Lactate | <0.03 | 0.24 | 0.20 | 0.13 | ND | 0.49 | 0.15 | ND | <0.03 |
| Hydrochloride | 0.05 | 0.18 | 0.16 | 0.22 | ND | 0.52 | 0.18 | ND | ND |

[1]Different impurity profiles for the two sample preparations.

Morphology of Scaled-Up Salts

Figure 40:
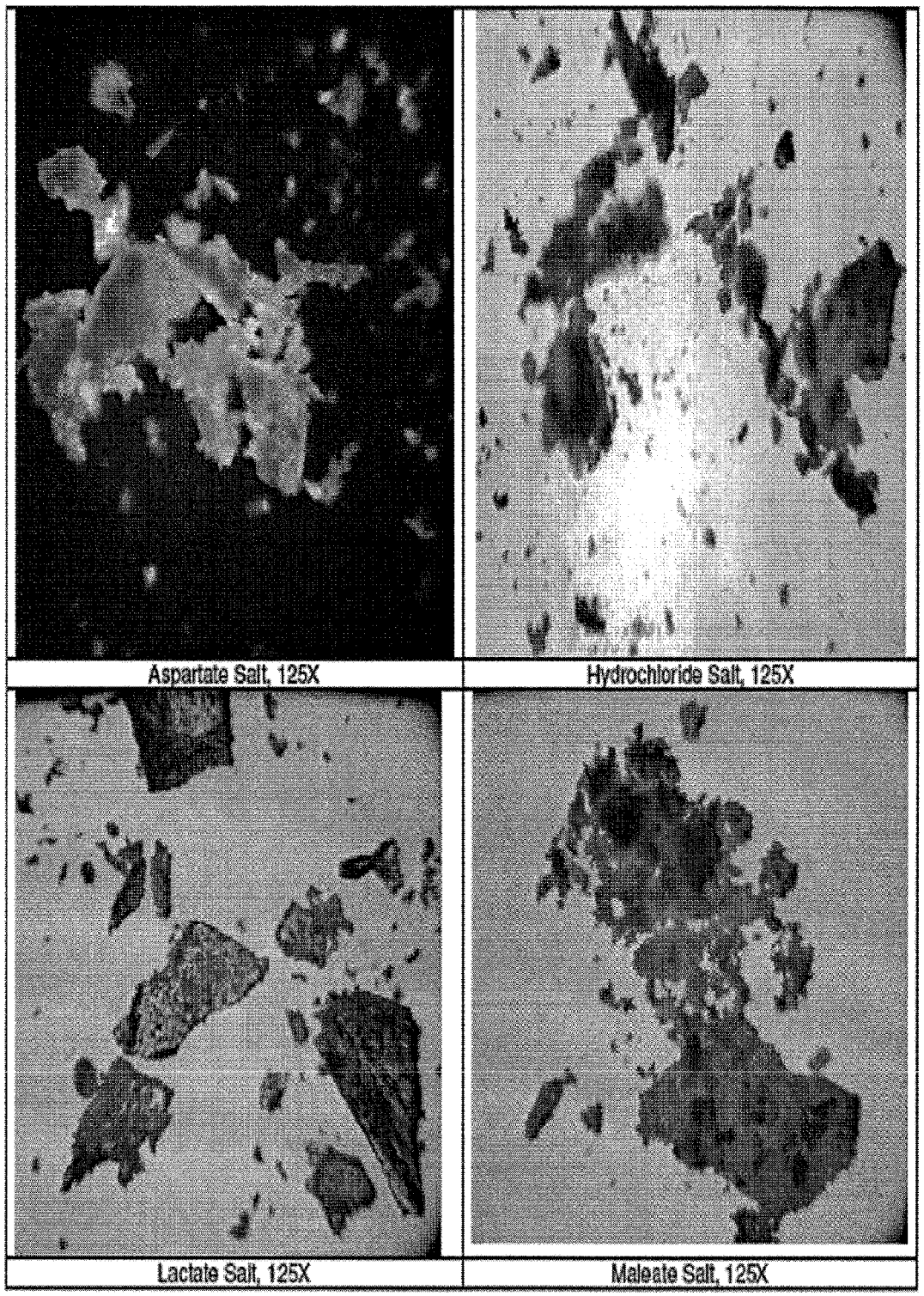
FIG. 40 shows particle morphology of four scaled-up salts.

The particle morphology of the four scaled-up salts was evaluated. Aspartate, hydrochloride and maleate particles were irregularly shaped, platy and did not appear birefringent. The lactate particles appeared larger and not as thin as other salts (see FIG. 40).

Example 9

Properties of Scaled-Up Salts

Scale-up (on a 300 mg scale) of four salts was done: aspartate, maleate lactate, and hydrochloride. HCl and aspartate salts were analyzed by XRD, DSC, TGA.

Figure 41:
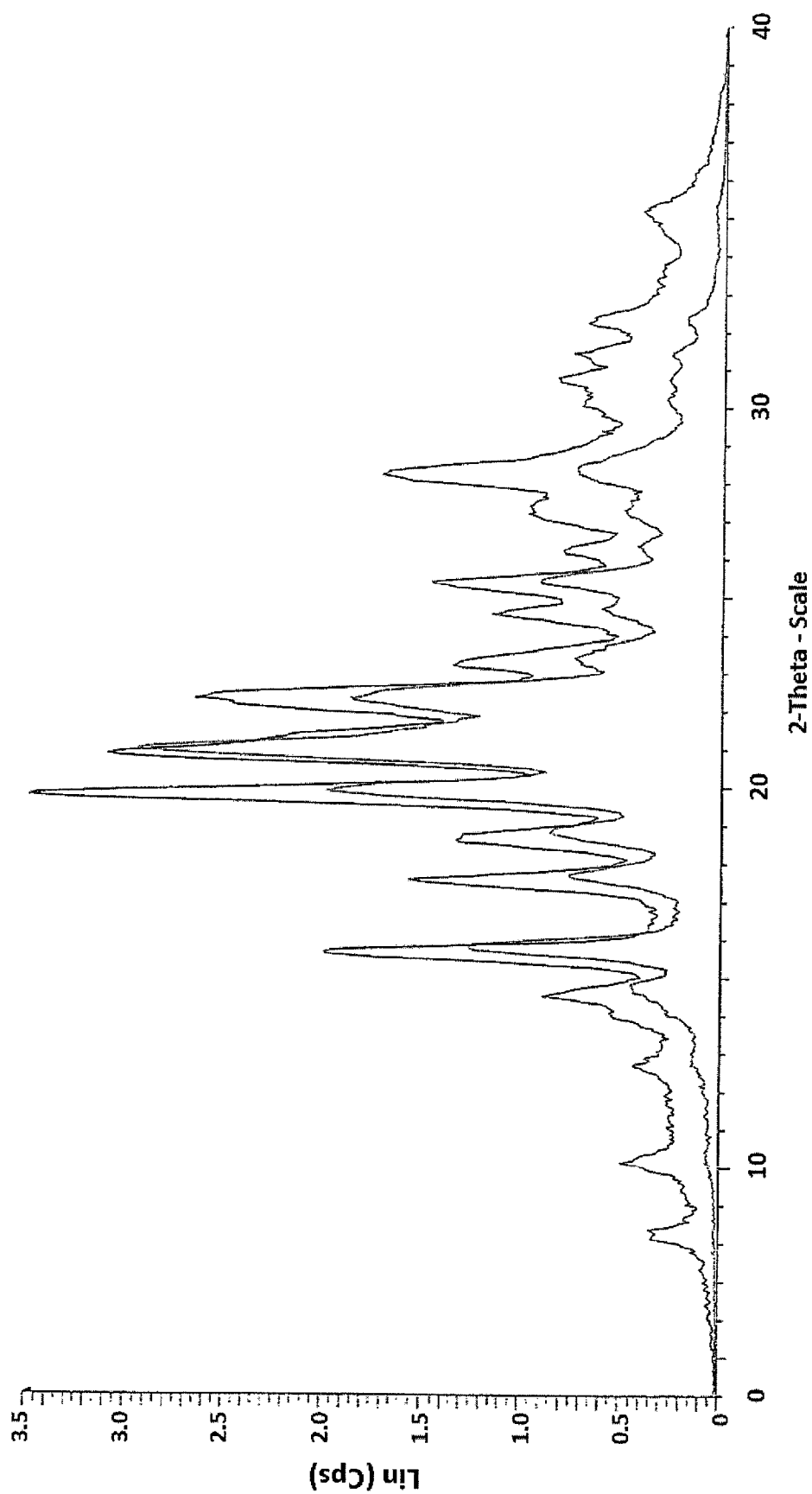
FIG. 41 shows XRD data for HCl salt.
Figure 42:
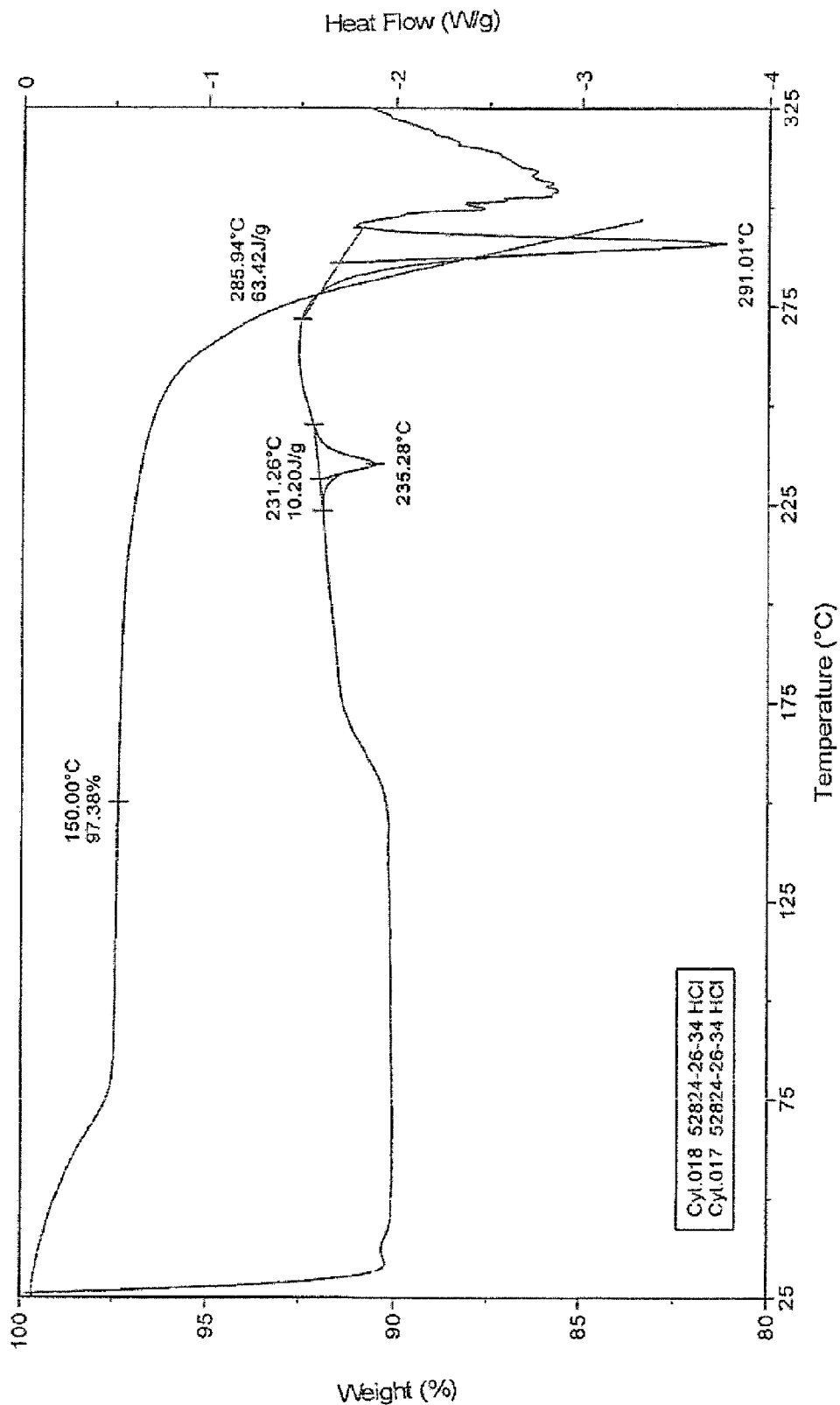
FIG. 42 shows DSC/TGA data for HCl salt.
Figure 43:
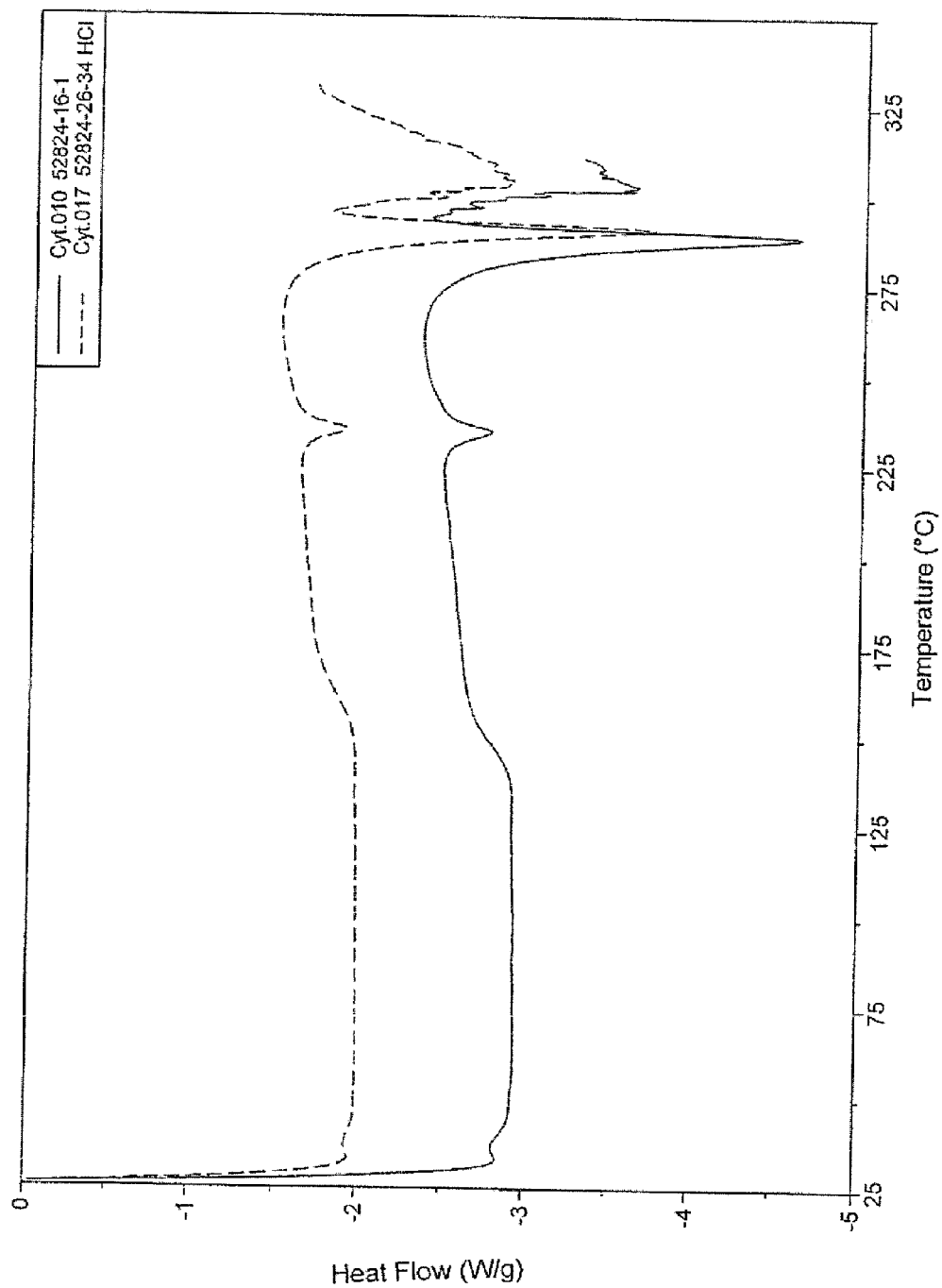
FIG. 43 shows DSC comparison of the scaled-up sample (upper trace) and a small scale sample (lower trace).

XRD overlay of the scaled-up salt (red) with a small scale batch (black) is in FIG. 41. DSC/TGA data for the scaled-up HCl is in FIG. 42, FIG. 43 shows the DSC overlay with a small scale sample. Both XRD and DSC data were good matches to the small scale sample. The salt was relatively dry: amount of volatiles detected for HCl was 2.6%.

Figure 44:
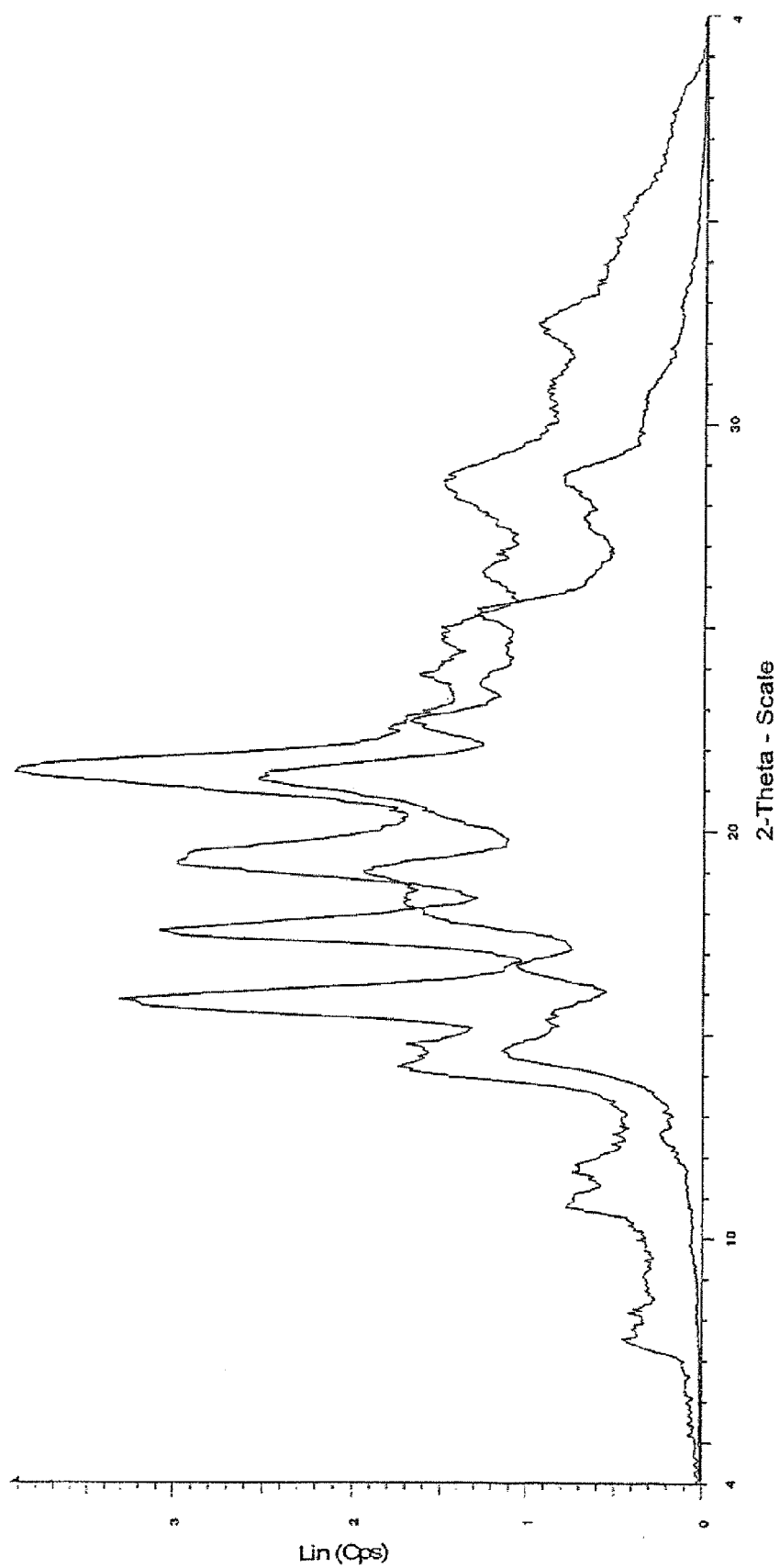
FIG. 44 shows XRD data for aspartate salt.
Figure 45:
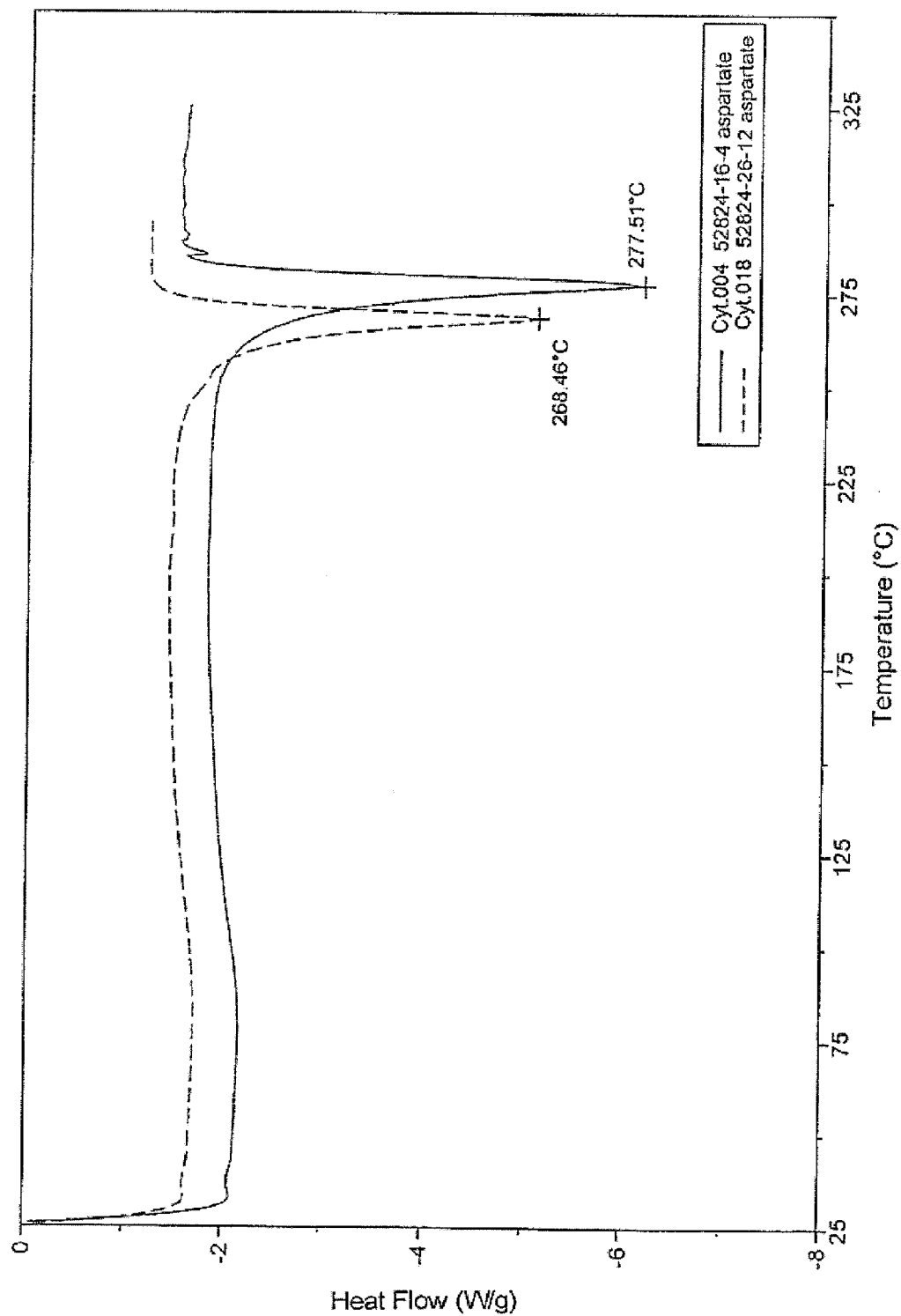
FIG. 45 shows DSC/TGA data for aspartate salt.
Figure 46:
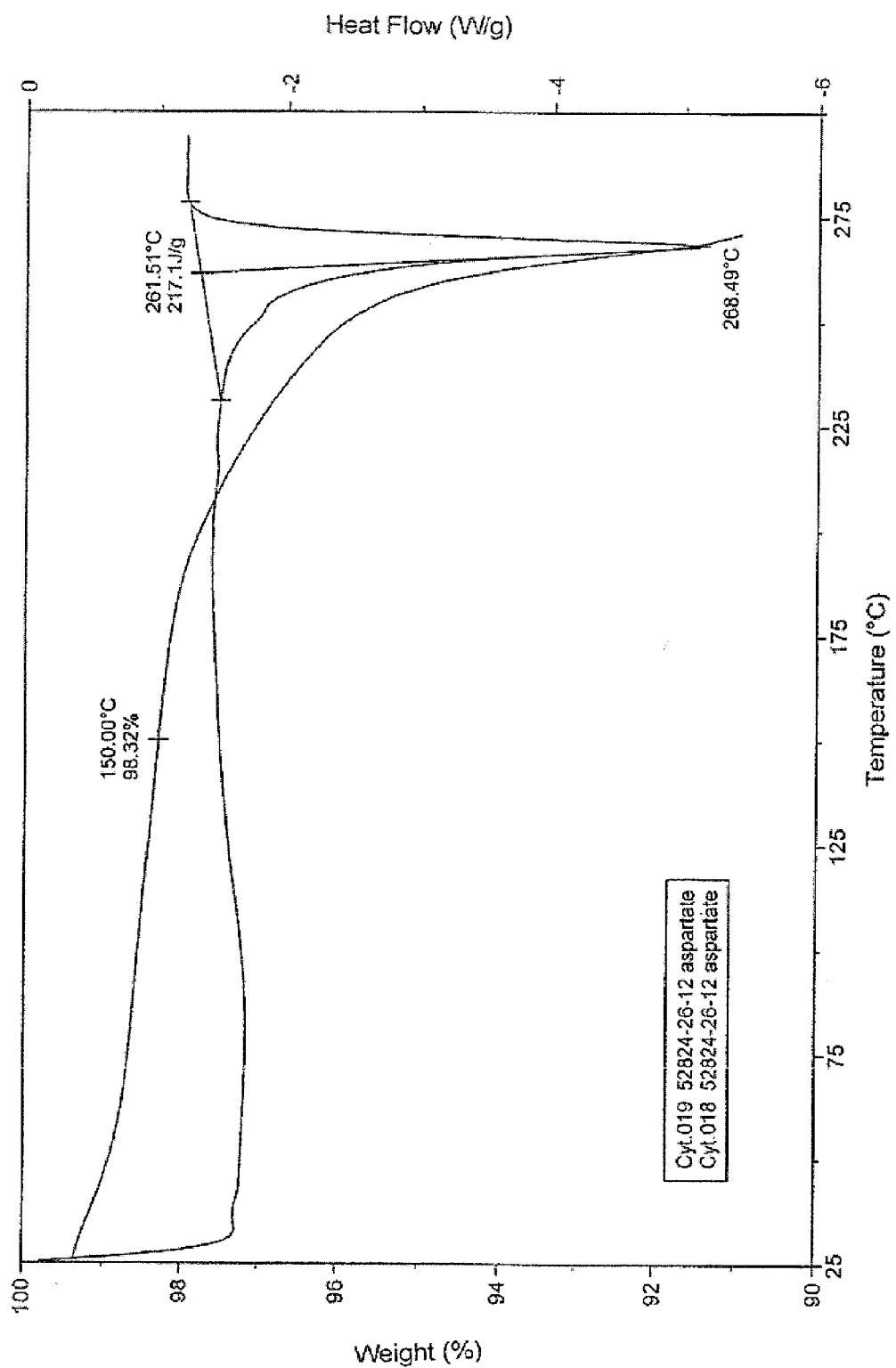
FIG. 46 shows DSC data. Scaled-up aspartate (upper trace), small scale sample (lower trace.

XRD overlay of the scaled-up salt (black) with a small scale batch (blue) is in FIG. 44. DSC/TGA data for the scaled-up aspartate is in FIG. 45, FIG. 46 shows the DSC overlay with a small scale sample. Scaled-up sample appears to be less crystalline than the small scale sample despite the fact that the additional ripening in water was done to improve crystallinity. DSC shows a single melt with an earlier melting onset than the small scale sample, probably due to reduction in crystallinity. The sample had 1.7 wt % volatiles.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed:

1. A peptide salt wherein the peptide has a sequence selected from SEQ ID NOs: 1-26 and the salt is aspartate.

2. The peptide salt, according to claim 1, wherein the peptide is SEQ ID NO:13.

3. A pharmaceutical composition comprising a peptide salt wherein the peptide has a sequence selected from SEQ ID NOs: 1-26 and the salt is aspartate.

4. The pharmaceutical composition, according to claim 3, wherein the peptide is SEQ ID NO:13.

5. A method for treating a condition that is modulated by μ-opiate receptor activity, wherein said method comprises administering, to a patient in need of such treatment a peptide salt wherein the peptide has a sequence selected from SEQ ID NOs: 1-26 and the salt is aspartate.

6. The method, according to claim 5, wherein the peptide is SEQ ID NO:13.

7. The method, according to claim 5, which is used to provide analgesia or to treat a condition selected from the group consisting of gastrointestinal disorders, inflammation, and drug dependence.

* * * * *

UNITED STATES PATENT AND TRADEMARK OFFICE
CERTIFICATE OF CORRECTION

| | | |
|---|---|---|
| PATENT NO. | : 8,940,704 B2 | Page 1 of 1 |
| APPLICATION NO. | : 14/056496 | |
| DATED | : January 27, 2015 | |
| INVENTOR(S) | : Theodore E. Maione | |

It is certified that error appears in the above-identified patent and that said Letters Patent is hereby corrected as shown below:

In the Specification

Column 1,
Line 44, "at the receptor" should read --at the µ receptor--.

Column 10,
Line 44, "RE" should read --RH--.

Column 18,
Table 10, Line 47, "0.003" should read --<0.003--.

Signed and Sealed this
Fifteenth Day of December, 2015

Michelle K. Lee
*Director of the United States Patent and Trademark Office*

SEQUENCE LISTING

```
<160> NUMBER OF SEQ ID NOS: 26

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Amidated Phenylalanine

<400> SEQUENCE: 1

Tyr Pro Trp Phe
1

<210> SEQ ID NO 2
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Amidated Phenylalanine

<400> SEQUENCE: 2

Tyr Pro Phe Phe
1

<210> SEQ ID NO 3
<211> LENGTH: 4
<212> TYPE: PRT
```

```
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Hydroxylated Phenylalanine

<400> SEQUENCE: 3

Tyr Pro Trp Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Hydroxylated Phenylalanine

<400> SEQUENCE: 4

Tyr Pro Phe Phe
1

<210> SEQ ID NO 5
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Amidated Phenylalanine

<400> SEQUENCE: 5

Tyr Pro Trp Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic mu-opiate receptor peptides

<400> SEQUENCE: 6

Tyr Pro Phe Phe
1

<210> SEQ ID NO 7
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Nitrosylated Tryptophan
<220> FEATURE:
<221> NAME/KEY: MISC_FEATURE
<222> LOCATION: (4)..(4)
<223> OTHER INFORMATION: Amidated Phenylalanine

<400> SEQUENCE: 7

Tyr Pro Trp Phe
```

```
<210> SEQ ID NO 8
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Nitrosylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 8

Tyr Pro Phe Phe
1

<210> SEQ ID NO 9
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 9

Tyr Pro Phe Phe
1

<210> SEQ ID NO 10
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 10

Tyr Pro Phe Phe
1

<210> SEQ ID NO 11
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
```

```
<223> OTHER INFORMATION: Amidated Phenylalanine

<400> SEQUENCE: 11

Tyr Pro Phe Phe
1

<210> SEQ ID NO 12
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 12

Tyr Pro Phe Phe
1

<210> SEQ ID NO 13
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide

<400> SEQUENCE: 13

Tyr Lys Trp Phe
1

<210> SEQ ID NO 14
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide

<400> SEQUENCE: 14

Tyr Lys Phe Phe
1

<210> SEQ ID NO 15
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine

<400> SEQUENCE: 15
```

Tyr Xaa Trp Phe
1

<210> SEQ ID NO 16
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine

<400> SEQUENCE: 16

Tyr Xaa Phe Phe
1

<210> SEQ ID NO 17
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Nitrosylated Tryptophan

<400> SEQUENCE: 17

Tyr Lys Trp Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Nitrosylated Phenylalanine

<400> SEQUENCE: 18

Tyr Lys Phe Phe
1

<210> SEQ ID NO 19
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:

```
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Nitrosylated Tryptophan

<400> SEQUENCE: 19

Tyr Xaa Trp Phe
1

<210> SEQ ID NO 20
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Nitrosylated Phenylalanine

<400> SEQUENCE: 20

Tyr Xaa Phe Phe
1

<210> SEQ ID NO 21
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 21

Tyr Lys Phe Phe
1

<210> SEQ ID NO 22
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Alkylated Phenylalanine
```

```
<400> SEQUENCE: 22

Tyr Xaa Phe Phe
1

<210> SEQ ID NO 23
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 23

Tyr Lys Phe Phe
1

<210> SEQ ID NO 24
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Alkylated Phenylalanine

<400> SEQUENCE: 24

Tyr Xaa Phe Phe
1

<210> SEQ ID NO 25
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 25

Tyr Lys Phe Phe
1

<210> SEQ ID NO 26
<211> LENGTH: 4
<212> TYPE: PRT
<213> ORGANISM: Artificial Sequence
<220> FEATURE:
<223> OTHER INFORMATION: Synthetic mu-opiate receptor peptides
```

```
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 26

Tyr Lys Phe Phe
1
```